United States Patent
Lee et al.

(10) Patent No.: US 9,422,298 B2
(45) Date of Patent: *Aug. 23, 2016

(54) PYRIDOPYRIMIDINE DERIVATIVES AND USE THEREOF

(71) Applicant: CMG Pharmaceutical Co., Ltd., Seoul (KR)

(72) Inventors: Gilnam Lee, Gyeonggi-Do (KR); Chul Soo Lim, Seoul (KR); Han Won Cho, Seoul (KR); Jeongbeob Seo, Gyeonggi-Do (KR); Albert C. Gyorkos, Westminster, CO (US); Suk Young Cho, Kyunggi-Do (KR); Eun Kyung Choi, Seoul (KR); Choung Soo Kim, Kyunggi-Do (KR); Jung Jin Hwang, Seoul (KR); Jin Sung Kim, Seoul (KR); Hee Jung An, Gyeonggi-do (KR); Yong Wha Moon, Gyeonggi-do (KR)

(73) Assignees: CMG Pharmaceutical Co., Ltd., Seoul (KR); Sung Kwang Medical Foundation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/622,447

(22) Filed: Feb. 13, 2015

(65) Prior Publication Data

US 2015/0158874 A1    Jun. 11, 2015

Related U.S. Application Data

(60) Continuation-in-part of application No. 14/137,158, filed on Dec. 20, 2013, which is a division of application No. 13/423,950, filed on Mar. 19, 2012, now Pat. No. 8,664,230.

(60) Provisional application No. 61/453,850, filed on Mar. 17, 2011.

(51) Int. Cl.
| | |
|---|---|
| *A61K 31/519* | (2006.01) |
| *C07D 471/02* | (2006.01) |
| *C07D 487/04* | (2006.01) |
| *C07D 471/04* | (2006.01) |

(52) U.S. Cl.
CPC ............ *C07D 487/04* (2013.01); *C07D 471/04* (2013.01)

(58) Field of Classification Search
CPC ............................. A61K 31/519; C07D 471/02
USPC ........................ 544/253, 279; 514/256, 258.1
See application file for complete search history.

(56) References Cited

U.S. PATENT DOCUMENTS

| 8,338,435 B2 * | 12/2012 | Herdewijn et al. ......... 514/258.1 |
| 8,536,187 B2 * | 9/2013 | Canales et al. ............ 514/264.11 |
| 8,664,230 B2 * | 3/2014 | Lee et al. ................... 514/258.1 |

FOREIGN PATENT DOCUMENTS

WO    2009/039140 A1    3/2009

OTHER PUBLICATIONS

Chinese Office Action for Chinese Patent Application No. 201380026067.6, English translation, Issued Jun. 17, 2015, 10 pages.

* cited by examiner

*Primary Examiner* — Golam M M Shameem
(74) *Attorney, Agent, or Firm* — Mintz Levin Cohn Ferris Glovsky and Popeo, P.C.; Kongsik Kim; Elaine V. Morlock

(57) ABSTRACT

The invention provides novel substituted pyridopyrimidines represented by Formula I or a pharmaceutically acceptable salt, solvate, polymorph, ester, tautomer or prodrug thereof, and a composition comprising these compounds. The compounds provided can be used as inhibitors of the phosphoinositide 3' OH kinase family (PI3K) for the treatment of inflammatory diseases, cancer, cardiovascular diseases, allergy, asthma and autoimmune disorders.

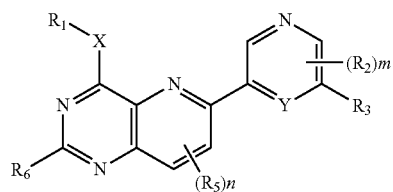

Formula I

2 Claims, No Drawings

PYRIDOPYRIMIDINE DERIVATIVES AND USE THEREOF

CROSS-REFERENCE TO RELATED APPLICATIONS

This application is a continuation-in-part application of U.S. patent application Ser. No. 14/137,158 filed on Dec. 20, 2013, which is a divisional application of U.S. patent application Ser. No. 13/423,950 filed Mar. 19, 2012, now U.S. Pat. No. 8,664,230, which claims priority to U.S. Provisional Patent Application No. 61/453,850 filed on Mar. 17, 2011. The foregoing applications are incorporated herein by reference.

TECHNICAL FIELD

This invention relates to a series of substituted pyridopyrimidine which are kinase inhibitors, especially inhibitors of the phosphoinositide 3' OH kinase family (hereinafter PI3 Kinase; PI3Kα, PI3Kβ, PI3Kγ and/or PI3δ) for treatment of inflammatory diseases, cancer, cardiovascular diseases, allergy, asthma and autoimmune disorders. This invention also relates to a pharmaceutical composition comprising the compound of the invention, use of the compound in the preparation of a medicament, and method of treatment for hyperproliferative diseases in mammals, especially humans by administering the compound thereof.

BACKGROUND ART

The phosphoinositide 3-kinases (PI3Ks) are a family of enzymes involved in cellular function such as cell growth, proliferation, differentiation, motility, survival and intracellular trafficking, which in turn are involved in cancer. And the PI3Ks utilize both lipid and protein kinase activity to regulate numerous intracellular signal transduction pathway, which in turn coordinate a range of downstream cellular processes.

The PI3K family is divided into three classes (I, II, and III). The classifications are based on primary structure, regulation, and in vitro lipid substrate specificity. Class I PI3Ks have received the most attention from the scientific community and are further broken down into two subclasses, 1A and 1B, which are responsible for the production of Phosphatidylinositol 3-phosphate (PI(3)P), Phosphatidylinositol (3,4)-bisphosphate (PI(3,4)P2), and Phosphatidylinositol (3,4,5)-trisphosphate (PI(3,4,5)P3) (Vanhaesebroeck et al., Trends Biochem. Sci., 1997, 22(7), 267-272; Leslie et al., Chem. Rev., 2001, 101(8), 2365-2380) (FIG. 1).

FIG. 1 Conversion of PIP2 to PIP3 by PI3K

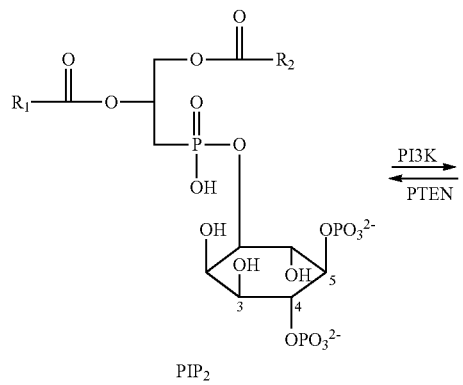

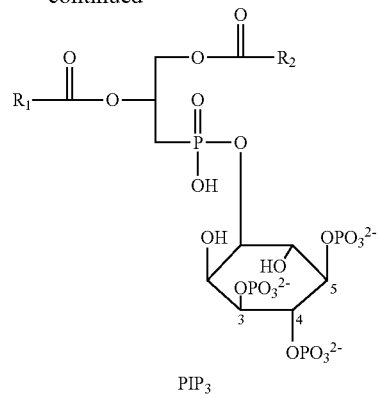

The class IA isoforms, PI3Kα, PI3Kβ, and PI3Kδ, are primarily activated by protein tyrosine kinase-coupled receptors, whereas the sole class IB member, PI3Kγ is activated by G-protein coupled receptors (GPCRs), such as chemokine receptors (Leevers S J et al., Current Opinion in Cell Biology 1999, 11(2) 219-225). Class IA PI3K is composed of a heterodimer between a p110 catalytic subunit and a p85 regulatory subunit (Carpenter C L et al., J. Biol. Chem. 1990, 265(32), 19704-19711). There are five variants of the p85 regulatory subunit, designated p85α, p55α, p50α, p85β, or p55γ. There are also three variants of the p110 catalytic subunit designated p110α, β, or δ catalytic subunit. The first three regulatory subunits are all splice variants of the same gene (Pik3r1), the other two being expressed by other genes (Pik3r2 and Pik3r3, p85β, and p55γ, respectively). The most highly expressed regulatory subunit is p85α; all three catalytic subunits are expressed by separate genes (Pik3ca, Pik3cb, and Pik3cd for p110α, p110β, and p110δ, respectively). The first two p110 isoforms (α and β) are expressed in all cells, but p110δ is expressed primarily in leukocytes, and it has been suggested that it evolved in parallel with the adaptive immune system. The regulatory p101 and unique catalytic p110γ subunits comprise the type IB PI3K and are encoded by a single gene each. Each isoforms have unfolded the close connections between PI3Kα with oncogenesis, PI3Kβ, with thrombosis, PI3Kδ, with immune function and PI3Kγ with inflammation by pathophysiologic studies. Class II PI3Ks include PI3K C2a, C2p and C2y subtypes, which are characterized by containing C2 domains at the C terminus. The substrate for class III PI3Ks is PI only.

Wortmannin and LY294002 are well known and studied as a first generation PI3K inhibitor. Wortmannin was first isolated from *Penicillium wortmanni* in 1957 (Brian, P. W. et al., Bri. Mycol. Soc., 1957, 40, 365-368), but the structure was recognized in 1974 (Wiesinger, D. et al., Cell Mol. Life. Sci., 1974, 30, 135-136). It was reported for the anti-inflammatory activity (Wiesinger, D. et al, Experintia, 1974, 30, 135-136) and identified as a PI3K inhibitor (Powis, G. et al., Cancer Res., 1994, 54, 2419-2423). LY294002 is the first synthetic PI3K inhibitor with a quercetin modified chemical structure. LY294002 wa first described as a competitive PI3K inhibitor in 1994 (Vlahos, C. J. et al., J. Biol. Chem., 1994, 269, 5241-5248).

Compounds suitable as PI3K inhibitors are also disclosed in WO 07/044,729; WO 08/152,390; WO 08/070,740; WO 09/039,140; WO 09/052,145; WO 09/143,317; WO 10/002, 954; WO 10/037,765; WO 10/091,996; WO 10/100,144; WO 10/135,014; WO 10/144,513; WO 10/102,958; WO 10/133, 318 and WO 10/007,099.

SUMMARY

This invention provides for novel heterocyclic a compound of formula I or a pharmaceutically acceptable salt, solvate, polymorph, ester, tautomer or prodrug thereof:

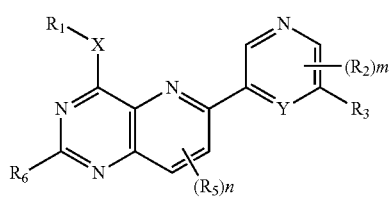

wherein
X is C or O or N or S;
Y is C or N;
R1 is selected from the group consisting of: acyl, amino, substituted amino, C1-C6alkyl, substituted C1-C6alkyl, C3-C7cycloalkyl, substituted C3-C7cycloalkyl, C3-C7heterocycloalkyl, substituted C3-C7 heterocycloalkyl, alkylcarboxy, arylamino, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, nitro;
R2 is selected from the group consisting of: hydrogen, halogen, acyl, amino, substituted amino, C1-C6alkyl, substituted C1-C6alkyl, C3-C7cycloalkyl, substituted C3-7Ccycloalkyl, C3-7Cheterocycloalkyl, substituted C3-C7heterocycloalkyl, alkylcarboxy, arylamino, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, nitro, alkoxy, C3-C7cycloalkyloxy, substituted C3-C7cycloalkyloxy, C3-C7heterocycloalkyloxy, substituted C3-7Cheterocycloalkyloxy, acyloxy, aryloxy;
R3=NR4'SO2R4, SO2NR4'R4, NR4'COR4, CONR4'R4, NR4'CONHR4;
R4 is selected from the group consisting of: alkyl, substituted alkyl, amino, halo, C3-C7cycloalkyl, substituted C3-C7cycloalkyl, C3-C7heterocycloalkyl, substituted C3-C7heterocycloalkyl, aryl, substituted aryl, heteroaryl and substituted heteroaryl;
R4' is H or C1-C6 alkyl;
R5 is selected from the group consisting of: hydrogen, halogen, C1-C6alkyl;
R6 is selected from the group consisting of: hydrogen, halogen, acyl, alkoxy, amino, substituted amino, arylamino, C1-C6alkyl, substituted C1-C6 alkyl, C3-C7cycloalkyl, substituted C3-C7cycloalkyl, C3-C7heterocycloalkyl, substituted C3-C7heterocycloalkyl, aryl, substituted aryl, heteroaryl, and substituted heteroaryl;
n is 0 or 1; m is 0 or 1;
and/or a pharmaceutically acceptable salt thereof.

In other embodiments, the present invention provides compounds represented by the following Formulae:

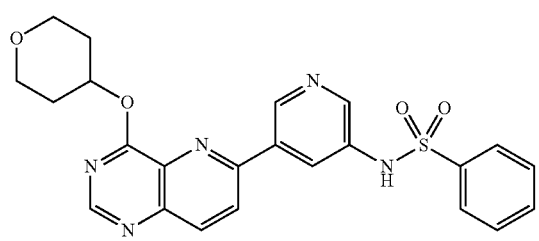

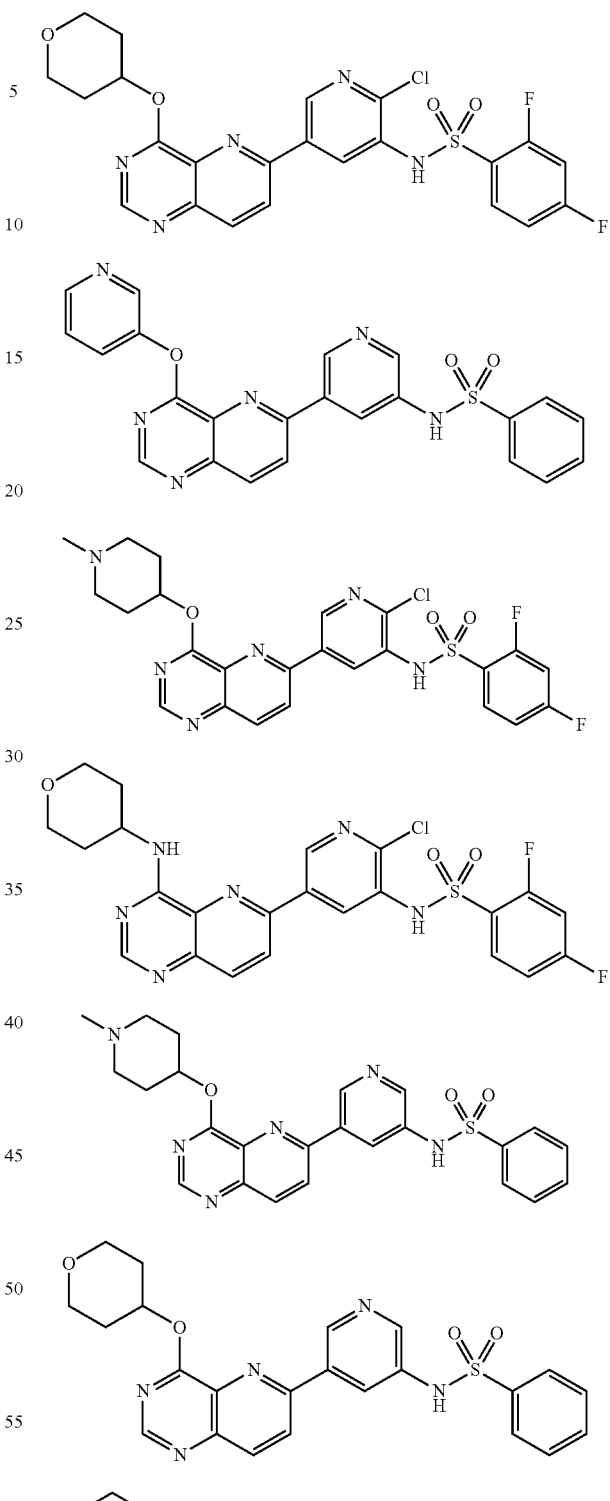

-continued

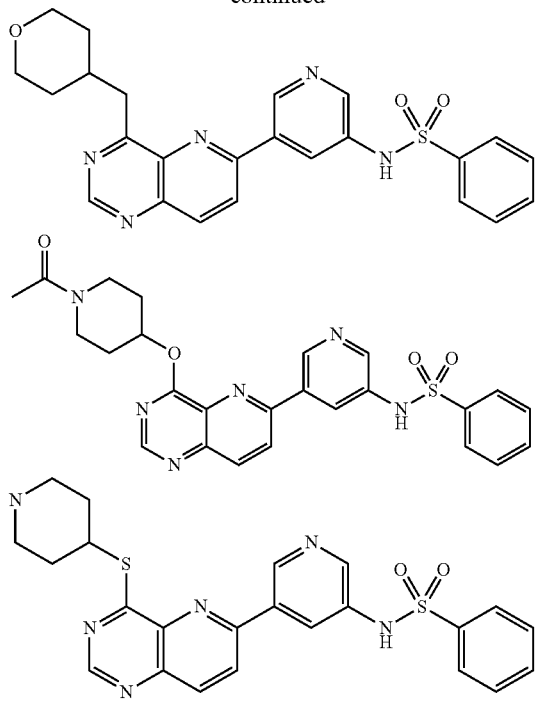

or a pharmaceutically acceptable salt, solvate, polymorph, ester, tautomer or prodrug thereof.

This invention also provides for novel heterocyclic a compound of formula Ia a pharmaceutically acceptable salt, solvate, polymorph, ester, tautomer or prodrug thereof:

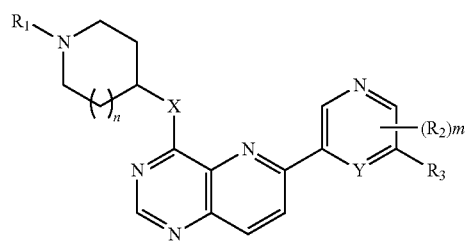

wherein X is NH;

Y is CH;

R$_1$ is H, C$_3$-C$_7$heterocycloalkyl, substituted C$_3$-C$_7$heterocycloalkyl, or COOR$_5$, SOOR$_5$, or CONR$_6$R$_7$;

R$_2$ is halogen;

R$_3$ is NHSO$_2$R$_4$;

R$_4$ is selected from the group consisting of aryl, substituted aryl, heteroaryl and substituted heteroaryl;

R$_5$ is selected from the group consisting of H, alkyl, cycloalkyl, aryl, substituted aryl, heteroaryl and substituted heteroaryl;

R$_6$ and R$_7$ are independently selected from the group consisting of H, alkyl, cycloalkyl, aryl, substituted aryl, heteroaryl and substituted heteroaryl; or R$_6$ and R$_7$ are taken together with the nitrogen atom to form C$_3$-C$_7$heterocycloalkyl or substituted C$_3$-C$_7$heterocycloalkyl;

n is 0, 1 or 2;

m is 0 or 1.

In certain embodiments, the present invention provides compounds represented by the following Formulae:

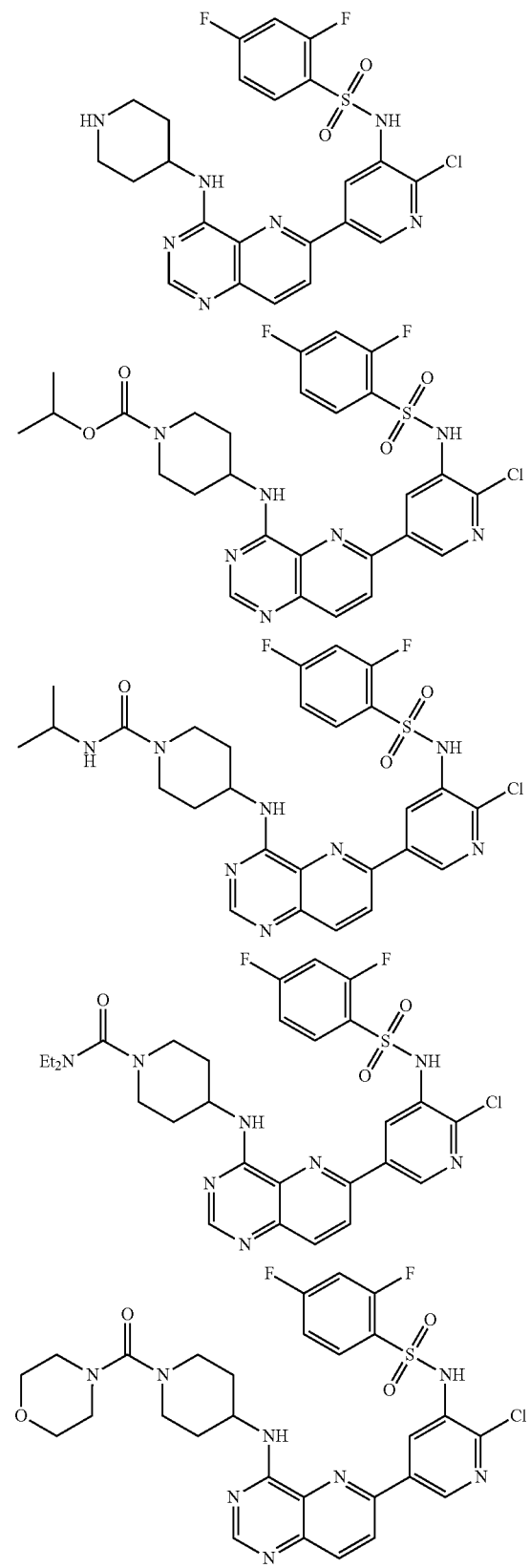

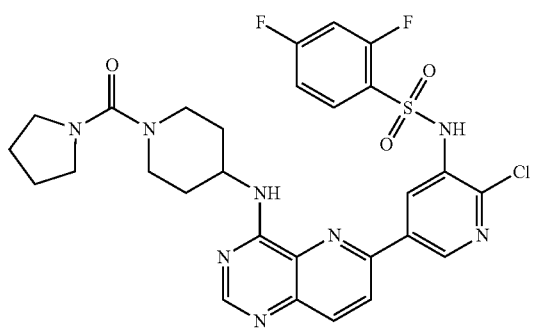

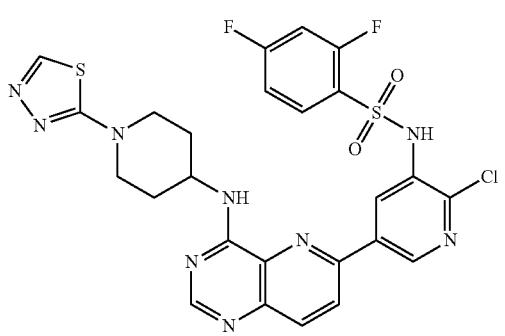

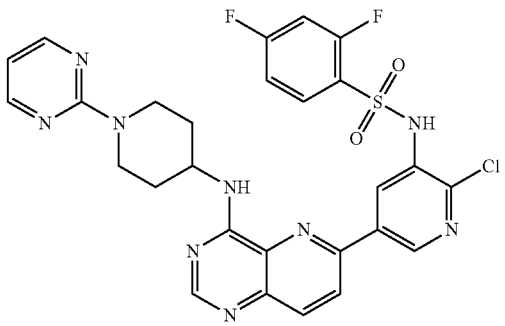

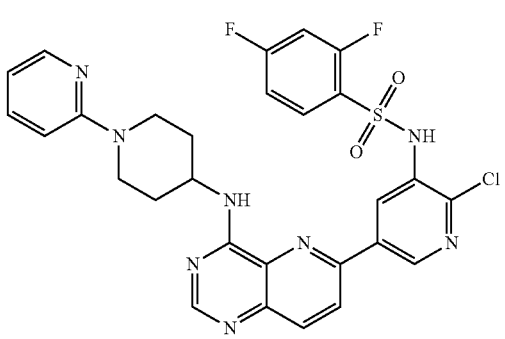

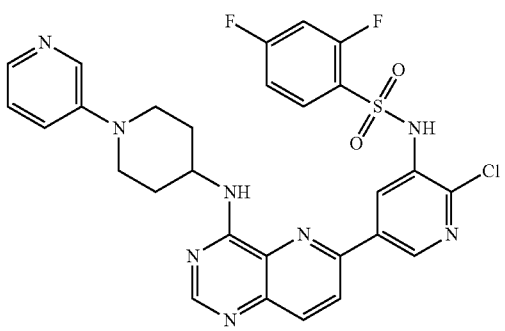

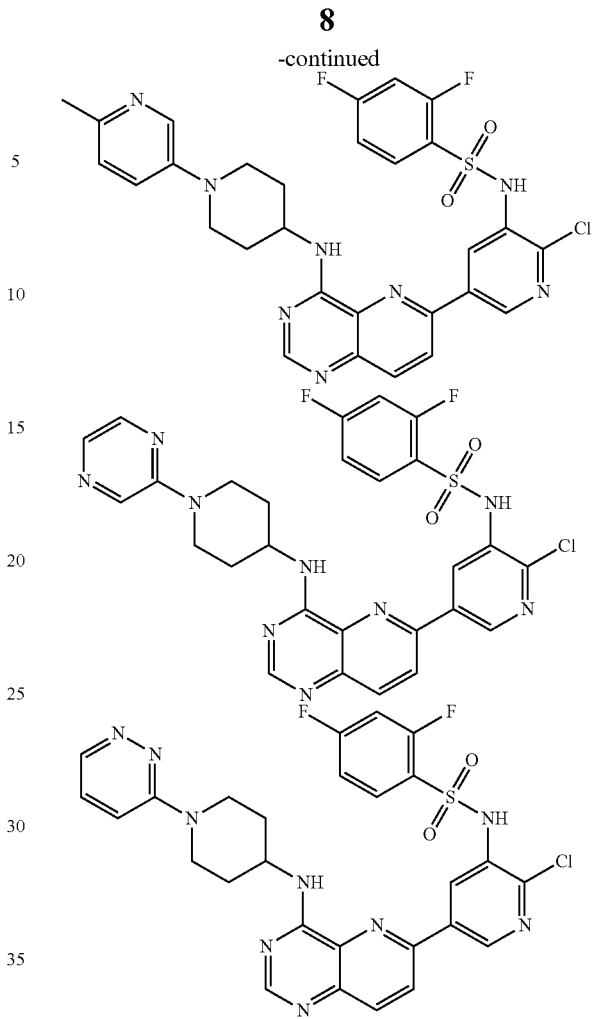

or a pharmaceutically acceptable salt, solvate, polymorph, ester, tautomer or prodrug thereof.

Compounds of present invention are inhibitors of PI3K and, consequently, are useful for treating cancers and other hyperproliferative diseases.

Compounds of present invention are inhibitors of PI3K and, consequently, are also related to a method of treating one or more disease states selected from: autoimmune disorders, inflammatory diseases, allergy, asthma, cardiovascular diseases, kidney diseases, pancreatitis, multiorgan failure and thrombosis.

In other aspects, the present invention is directed to a pharmaceutical composition comprising an effective amount of a compound of formula I or a pharmaceutically acceptable salt, solvate, polymorph, ester, tautomer or prodrug thereof. In some embodiments, the pharmaceutical composition further comprises a pharmaceutically acceptable carrier, adjuvants and/or excipients. In some embodiments, such a composition may contain at least one of preservatives, agents for delaying absorption, fillers, binders, adsorbents, buffers, disintegrating agents, solubilizing agents, and other carriers, adjuvants and/or excipients as inert ingredients. The composition may be formulated with a method well-known in the art.

In some aspects, the present invention is directed to a method of treating a disease in an individual suffering from said disease comprising administering to said individual a therapeutically effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of a compound of formula I or a pharmaceutically acceptable salt, solvate, polymorph, ester, tautomer or prodrug thereof.

In other aspects, the present invention is directed to a method of treating a disorder in a human, comprising administering to said human a therapeutically effective amount of a compound of formula I or a pharmaceutically acceptable salt, solvate, polymorph, ester, tautomer or prodrug thereof.

In other aspects, the present invention is directed to a method of treating an inflammatory disease, condition, or disorder in a mammal, including a human, comprising administering to said mammal a therapeutically effective amount of a compound of formula I or a pharmaceutically acceptable salt, ester, prodrug, solvate, such as hydrate, polymorph or tautomer thereof.

In other aspects, the present invention is directed to a method of treating a disorder or condition which is modulated by the PI3K cascade in a mammal, including a human, comprising administering to said mammal an amount of the compound of formula I or a pharmaceutically acceptable salt, ester, prodrug, solvate, such as hydrate, polymorph or tautomer thereof, effective to modulate said cascade. The appropriate dosage for a particular patient can be determined, according to known methods, by those skilled in the art.

In other aspects, the present invention is directed to use of compound of formula I or a pharmaceutically acceptable salt, ester, prodrug, solvate, such as hydrate, polymorph or tautomer thereof in the preparation of a pharmaceutical composition. The pharmaceutical composition can be used for treating a disorder or condition which is modulated by the PI3K cascade in a mammal, including a human. The pharmaceutical composition is useful for treating cancer, inflammatory disease and other hyperproliferative diseases.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension. In some embodiments, the pharmaceutical composition is in a form suitable for parenteral injection, such as a sterile solution, suspension or emulsion; for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent In further or additional embodiments, the therapeutic agent is selected from the group consisting of cytotoxic agents, anti-angiogenesis agents and anti-neoplastic agents. In further or additional embodiments, the anti-neoplastic agent is selected from the group consisting of alkylating agents, anti-metabolites, epidophyllotoxins; antineopiastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy or a combination of both. In further or additional embodiments, the pharmaceutical composition comprises a pharmaceutically acceptable salt of a compound of formula I.

In other aspects, the present invention is directed to a method for inhibiting a PI3K enzyme. The method comprises contacting said PI3K enzyme with an amount of a composition comprising a compound of formula I or a pharmaceutically acceptable salt, solvate, polymorph, ester, tautomer or prodrug thereof, sufficient to inhibit said enzyme, wherein said enzyme is inhibited. In some embodiments, the present invention is directed to a method for selectively inhibiting a PI3K enzyme.

In other aspects, the present invention is directed to use of a compound of formula I or a pharmaceutically acceptable salt, solvate, polymorph, ester, tautomer or prodrug thereof in the preparation of a pharmaceutical composition for inhibiting a PI3K enzyme.

In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited.

In other aspects, the present invention is directed to a method of treatment of a PI3K mediated disorder in an individual suffering from said disorder comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for treating a PI3K mediated disorder.

In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution and suspension for oral administration, for parenteral injection as a sterile solution, suspension or emulsion, for topical administration as an ointment or cream, or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the PI3K mediated disorder is a mammal. In further or additional embodiments, the individual is a human. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the PI3K mediated disorder is selected from the group consisting of inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the PI3K mediated disorder is an inflammatory disease. In further or additional embodiments, the PI3K mediated disorder is a hyperproliferative disease. In further or additional embodiments, the PI3K mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I is administered.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for degrading and/or inhibiting the growth of or killing a cancer cell.

In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded. In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed. In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of formula I is used.

In other aspects, the present invention is directed to a method for the treatment or prophylaxis of a proliferative disease in an individual comprising administering to said individual an effective amount of a composition comprising a compound of formula I or a pharmaceutically acceptable salt, solvate, polymorph, ester, tautomer or pro-drug thereof.

In other aspects, the present invention is directed to use of a compound of formula I or a pharmaceutically acceptable salt, solvate, polymorph, ester, tautomer or prodrug thereof in the preparation of a pharmaceutical composition for the treatment or prophylaxis of a proliferative disease.

In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of an inflammatory disease in an individual comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for the treatment or prophylaxis of an inflammatory disease.

In further or additional embodiments, the inflammatory disease is selected from chronic inflammatory diseases, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma. In some embodiments, the composition comprising a compound of formula I is administered in combination with an additional therapy. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of cancer in an individual comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for the treatment or prophylaxis of a cancer.

In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the antineoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method of reducing the size of a tumor, inhibiting tumor size increase, reducing tumor proliferation or preventing tumor proliferation in an individual, comprising administering to said individual an effective amount of a composition comprising a compound of formula I or a pharmaceutically acceptable salt, solvate, polymorph, ester, tautomer or prodrug thereof.

In other aspects, the present invention is directed to use of a compound of formula I or a pharmaceutically acceptable salt, solvate, polymorph, ester, tautomer or prodrug thereof in the preparation of a pharmaceutical composition for reducing the size of a tumor, inhibiting tumor size increase, reducing tumor proliferation or preventing tumor proliferation.

In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase. In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method for achieving an effect in a patient comprising the administration of an effective amount of a composition comprising a compound of formula I or a pharmaceutically acceptable salt, solvate, polymorph, ester, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases.

In other aspects, the present invention is directed to use of a compound of formula I or a pharmaceutically acceptable salt, solvate, polymorph, ester, tautomer or prodrug thereof in the preparation of a pharmaceutical composition for the inhibiting various cancers, immunological diseases, and/or inflammatory diseases.

In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a process for preparing a compound of formula I or a pharmaceutically acceptable salt, solvate, polymorph, ester, tautomer or prodrug thereof.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting. Definition of standard chemistry terms may be found in reference works, including Carey and Sundberg "ADVANCED ORGANIC CHEMISTRY 4TH ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, CH2O is equivalent to OCH2.

Unless otherwise noted, the use of general chemical terms, such as though not limited to "alkyl," "amine," "aryl," are equivalent to their optionally substituted forms. For example, "alkyl," as used herein, includes optionally substituted alkyl.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "catalytic group" refers to a chemical functional group that assists catalysis by acting to lower the activation barrier to reaction.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., CH2CH3), fully substituted (e.g., CF2CF3), mono-substituted (e.g., CH2CH2F) or substituted at a level anywhere in-between fully substituted and mono-substituted (e.g., CH2CHF2, CF2CH3, CFHCHF2, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, C1-Cn, includes C1-C2, C1-C3 . . . C1-Cn. By way of example only, a group designated as "C1-C4" indicates that there are one to four carbon atoms in the moiety, i.e. groups containing 1 carbon atom, 2 carbon atoms, 3 carbon atoms or 4 carbon atoms, as well as the ranges C1-C2 and C1-C3. Thus, by way of example only, "C1-C4 alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "C1-C6 alkyl" or "C1-6 alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

A non-limiting example of "cycloalkyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized $\pi$-electron system containing $4n+2$ $\pi$ electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic mono-radicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl) Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "heterocycle" as used herein, alone or in combination, refers collectively to heteroalicyclyl and heteroaryl groups. Herein, whenever the number of carbon atoms in a heterocycle is indicated (e.g., C1-C6 heterocycle), at least one non-carbon atom (the heteroatom) must be present in the ring. Designations such as "C1-C6 heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom.

The terms "halogen", "halo" or "halide" as used herein, alone or in combination refer to fluoro, chloro, bromo and iodo.

The term "alkoxy" as used herein, alone or in combination, refers to an alkyl ether radical, O-alkyl, including the groups O-aliphatic and O-carbocycle, wherein the alkyl, aliphatic and carbocycle groups may be optionally substituted, and wherein the terms alkyl, aliphatic and carbocycle are as defined herein. Non-limiting examples of alkoxy radicals include methoxy, ethoxy, n-propoxy, isopropoxy, n-butoxy, iso-butoxy, sec-butoxy, tertbutoxy and the like.

The term "sulfonyl" as used herein, alone or in combination, refers to the diradical —S(—O)2.

The terms "sulfonamide", "sulfonamido" and "sulfonamidyl" as used herein, alone or in combination, refer to the diradical groups —S(—O)2-NH— and —NH—S(=O)2

The terms "sulfamide", "sulfamido" and "sulfamidyl" as used herein, alone or in combination, refer to the diradical group NHS(—O)2NH.

Certain Pharmaceutical Terminology

The term "PI3K inhibitor" as used herein refers to a compound that exhibits an IC50, with respect to PI3K activity, of no more than about 100 µM or not more than about 50 µM, as measured in the PI3 kinase assay described generally herein. "IC50" is that concentration of inhibitor which reduces the activity of an enzyme (e.g., PI3K) to half-maximal level. Compounds described herein have been discovered to exhibit inhibition against PI3K. Compounds of the present invention preferably exhibit an IC50 with respect to PI3K of no more than about 10 µM, more preferably, no more than about 5 µM, even more preferably not more than about 1 µM, and most preferably, not more than about 200 nM, as measured in the PI3 kinase assay described herein.

The term "subject", "patient" or "individual" as used herein in reference to individuals suffering from a disorder, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon;

and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, y-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., J. Pharm. Sci. 1977, 66, 1-19). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, IV' (C1-4 alkyl)4, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

SYNTHETIC PROCEDURES AND EXAMPLES

Synthetic Procedure 1-Formula I

The Preparation of Compounds of Formula I is Outlined Below:

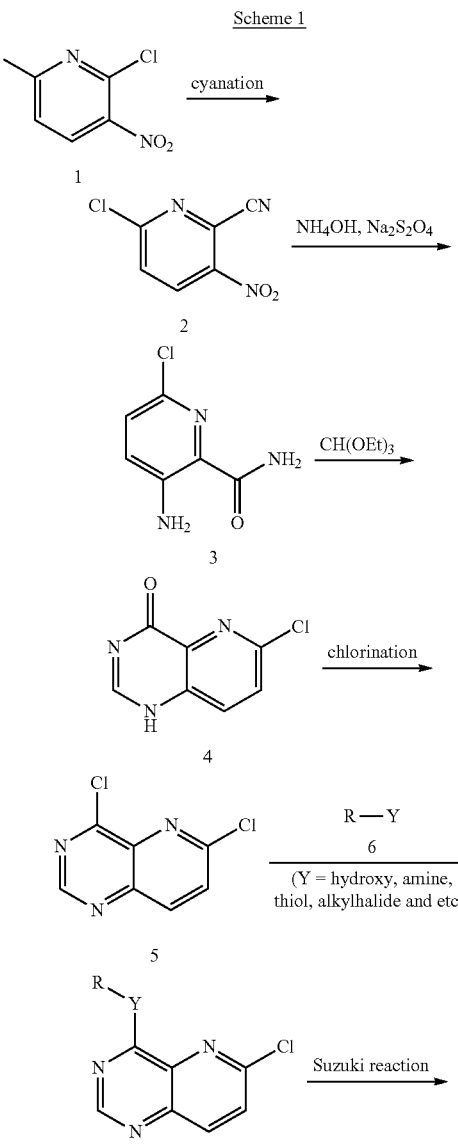

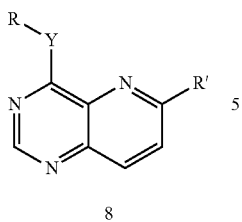

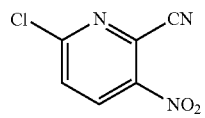

Scheme 1 above illustrates the preparation of pyridopyrimidine intermediates (8).

Cyanopyridine derivative (2) can be prepared via cyanation of dichloropyridine (1). Cyanopyridine (2) was treated with ammonium hydroxide and sodium hydrosulfite to give aminopyridine (3). The pyridopyrimidone (4) was obtained by cyclization using triethoxymethane. Subsequent chlorination of pyrimidone (4) gave dichloropyridopyrimidine (5). The pyridopyrimidine (5) was substituted by a compound (6) to provide compound (7), which was coupled with synthesized Suzuki reagent to give the desired pyridopyrimidines (8).

Scheme 2

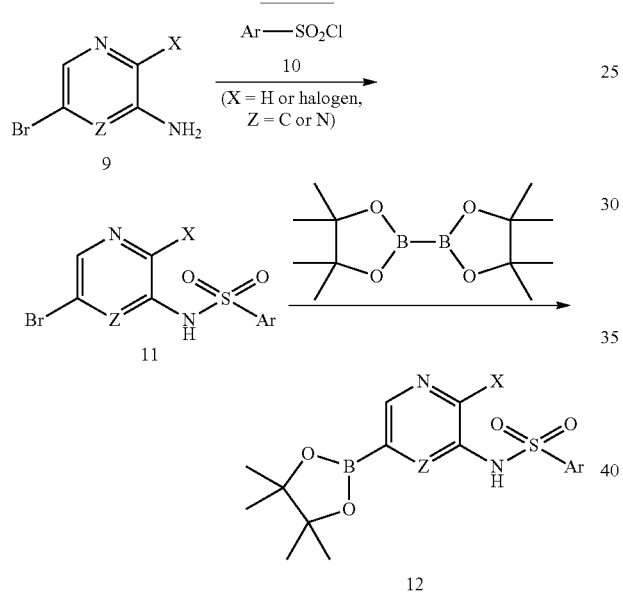

Scheme 2 illustrates the preparation of arylsulfonamide derivatives (12). Aminopyridine or pyrimidine (11) was reacted with arylsulfonylchloride (10) to provide sulfonamide (11). The sulfonamide (11) was reacted with pinacol borane to give the desired borate (12) utilized in the Suzuki reaction described in Scheme 1.

Intermediate 1

6-chloro-4-(tetrahydro-2H-pyran-4-yloxy)pyrido[3,2-d]pyrimidine

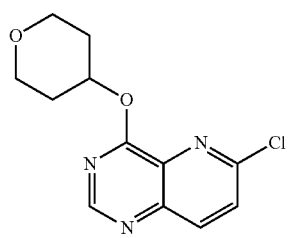 [SMILES: Clc1ccc2ncnc(OC3CCOCC3)c2n1]

Step A: 6-chloro-3-nitropicolinonitrile

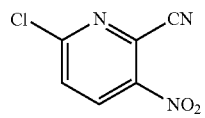

To a solution of 2,6-dichloro-3-nitropyridine (6.00 g, 31.1 mmol) in NMP (23.0 mL) was added copper(I) cyanide (3.06 g, 34.2 mmol) at room temperature. After stirred for 40 min at 180° C., the reaction mixture was cooled to room temperature, and then poured into ice water. After stirring for 10 min, the mixture was extracted with EtOAc, washed with brine, dried over anhydrous Na2SO4, filtered and concentrated in vacuo. The residue was purified by column chromatography on SiO2 (Hex:EtOAc=10:1) to give 6-chloro-3-nitropicolinonitrile (2.54 g, 44%) as a yellow solid. 1H-NMR (CDCl3, Varian 400 MHz) δ 7.79 (1H, d, J=8.4 Hz), 8.58 (1H, d, J=8.4 Hz).

Step B: 3-amino-6-chloropicolinamide

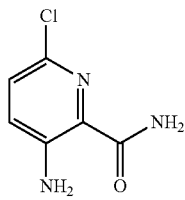 [SMILES: NC(=O)c1nc(Cl)ccc1N]

To a suspension of 6-chloro-3-nitropicolinonitrile (2.54 g, 13.8 mmol) in water (27.0 mL) was added NH4OH (5.61 mL, 36.0 mmol) at room temperature. After stirring for 20 min at room temperature, Na2S2O4 (13.7 g, 79.0 mmol) was added to the mixture. After stirring for 3 hours at room temperature, the reaction mixture was filtered, and washed with water. The filtercake was dried under vacuum to give 3-amino-6-chloropicolinamide (1.67 g, 70%) as a yellow solid. 1H-NMR (CDCl3, Varian 400 MHz) δ 5.36 (1H, brs), 6.00 (2H, brs), 7.00 (1H, d, J=8.8 Hz), 7.18 (1H, d, J=8.8 Hz), 7.63 (1H, brs).

Step C: 6-chloropyrido[3,2-d]pyrimidin-4(1H)-one

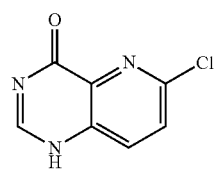 [SMILES: O=c1nc[nH]c2ccc(Cl)nc12]

A suspension of 3-amino-6-chloropicolinamide (1.67 g, 9.74 mmol) in triethyl orthoformate (73.0 mL) was refluxed for 3 hours. The reaction mixture was cooled to room temperature, and then filtered. The filtercake was dried under vacuum to give 6-chloropyrido[3,2-d]pyrimidin-4(1H)-one (1.45 g, 82%) as a brown solid. 1H-NMR (CDCl3, Varian 400 MHz) δ 7.66 (1H, d, J=8.4 Hz), 8.00 (1H, s), 8.03 (1H, d, J=1.2 Hz), 12.57 (1H, brs).

Step D: 4,6-dichloropyrido[3,2-d]pyrimidine

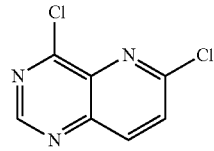 [SMILES: Clc1ccc2ncnc(Cl)c2n1]

To a solution of 6-chloropyrido[3,2-d]pyrimidin-4(1H)-one (150 mg, 0.83 mmol) in POCl3 (2.0 mL) was added DIPEA (0.22 mL, 1.24 mmol) at room temperature. After stirring for 1 hour at 110° C., the reaction mixture was cooled to room temperature. The reaction mixture was concentrated in vacuo, and then diluted with water and extracted with dichlormethane. The combined organic layers were washed brine, dried over anhydrous Na2SO4, filtered and concentrated in vacuo. The residue was purified by column chromatography on SiO2 (Hex:EtOAc=10:1) to give 4,6-dichloropyrido[3,2-d]pyrimidine (120 mg, 73%) as a yellow solid. 1H-NMR (CDCl3, Varian 400 MHz) δ 7.87 (1H, d, J=8.8 Hz), 8.35 (1H, d, J=8.8 Hz), 9.14 (1H, s).

Step E: 6-chloro-4-(tetrahydro-2H-pyran-4-yloxy)pyrido[3,2-d]pyrimidine

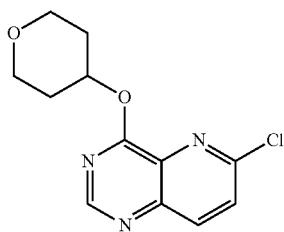 [SMILES: Clc1ccc2ncnc(OC3CCOCC3)c2n1]

To a solution of tetrahydro-2H-pyran-4-ol (0.042 mL, 0.440 mmol) in DMF (1.60 mL) was added NaH (21.0 mg, 55% dispersion in mineral oil, 0.480 mmol) at 0° C. After stirring for 30 min at room temperature, 4,6-dichloropyrido[3,2-d]pyrimidine (80.0 mg, 0.400 mmol) was added to the mixture at 0° C. After stirring for 2 hours at room temperature, the reaction mixture was quenched with saturated aq. NH4Cl, and then extracted with EtOAc. The combined organic layers were washed with brine, dried over anhydrous Na2SO4, filtered and concentrated in vacuo. The residue was purified by column chromatography on SiO2 (Hex:EtOAc=3:1) to give 6-chloro-4-(tetrahydro-2H-pyran-4-yloxy)pyrido[3,2-d]pyrimidine (60.0 mg, 57%) as a yellow solid. 1H-NMR (CDCl3, Varian 400 MHz) δ 2.02-2.11 (2H, m), 2.18-2.23 (2H, m), 3.62-3.68 (2H, m), 4.08-4.13 (2H, m), 5.59-5.63 (1H, m), 7.74 (1H, d, J=8.8 Hz), 8.19 (2H, d, J=8.8 Hz), 8.81 (1H, s).

Intermediate 2

N-(5-(4,4,5,5-tetramethyl-1,3,2-dioxaborolan-2-yl)pyridin-3-yl)benzenesulfonamide

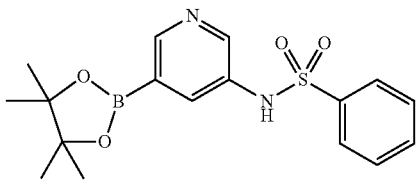 [SMILES: CC1(C)OB(c2cncc(NS(=O)(=O)c3ccccc3)c2)OC1(C)C]

Step A:
N-(5-bromopyridin-3-yl)benzenesulfonamide

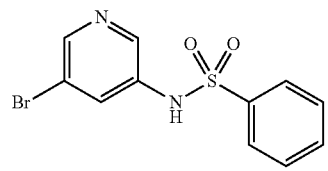 [SMILES: O=S(=O)(Nc1cncc(Br)c1)c1ccccc1]

To a solution of 5-bromopyridin-3-amine (1.00 g, 5.78 mmol) in pyridine (3.00 mL) was added benzenesulfonyl chloride (0.75 mL, 5.78 mmol) dropwise at 0° C. The mixture was stirred for 40 min at room temperature. The resulting solid was filtered, washed with water, and dried under vacuum to give N-(5-bromopyridin-3-yl)benzenesulfonamide (1.39 g, 77%) as a brown solid. 1H-NMR (DMSO-d6, Varian 400 MHz) δ 7.58-7.68 (4H, m), 7.79-7.81 (2H, m), 8.27 (1H, d, J=2.4 Hz), 8.37 (1H, d, J=2.0 Hz), 10.91 (1H, brs).

Step B: N-(5-(4,4,5,5-tetramethyl-1,3,2-dioxaborolan-2-yl)pyridin-3-yl)benzene-sulfonamide

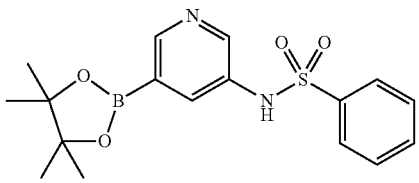 [SMILES: CC1(C)OB(c2cncc(NS(=O)(=O)c3ccccc3)c2)OC1(C)C]

A mixture of N-(5-bromopyridin-3-yl)benzenesulfonamide (1.00 g, 3.19 mmol), bis(pinacolato)diboron (0.89 g, 3.51 mmol), PdCl2(dppf)2CH2Cl2 (0.13 g, 0.16 mmol) and potassium acetate (0.94 g, 9.58 mmol) in 1,4-dioxane (7.51 mL) was stirred at 100° C. for 3 hours in a sealed tube. The reaction mixture was cooled to room temperature, filtered through a Celite pad and washed with EtOAc. The filtrate was concentrated in vacuo. The residue was triturated with dichloromethane and the resulting solid was filtered. The filtercake was dried under vacuum to give N-(5-(4,4,5,5-tetramethyl-1,3,2-dioxaborolan-2-yl)pyridin-3-yl)benzenesulfonamide (1.50 g, quent) as a brown solid. 1H-NMR (CDCl3, Varian 400 MHz) δ1.34 (12H, s), 7.46 (2H, t, J=7.6 Hz), 7.57 (1H, t, J=7.6 Hz), 7.76 (2H, d, J=7.2 Hz), 7.84 (1H, d, J=1.2 Hz), 8.35 (1H, d, J=2.4 Hz), 8.71 (1H, d, J=1.2 Hz); NH peak was not detected.

Intermediate 3

N-(2-chloro-5-(4,4,5,5-tetramethyl-1,3,2-dioxaborolan-2-yl)pyridin-3-yl)-2,4-difluorobenzenesulfonamide

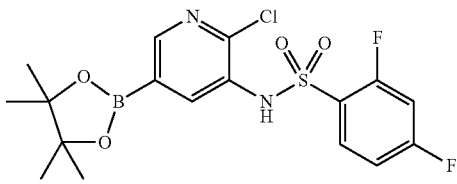 [SMILES: CC1(C)OB(c2cnc(Cl)c(NS(=O)(=O)c3ccc(F)cc3F)c2)OC1(C)C]

Step A: 5-bromo-2-chloro-3-nitropyridine

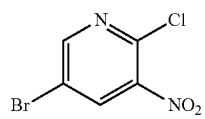 [SMILES: O=[N+]([O-])c1cc(Br)cnc1Cl]

To a solution of 5-bromo-3-nitropyridin-2(1H)-one (4.62 g, 21.10 mmol) in POCl3 (46.2 ml) was added DMF (4.62 ml, 59.7 mmol) at room temperature. The mixture was refluxed for 2 hours, and then cooled to room temperature and concentrated in vacuo. The residue was treated with saturated aq. NaHCO3 and extracted with EtOAc. The combined organic layers were washed with brine, dried over anhydrous Na2SO4, filtered and concentrated in vacuo. The residue was purified by column chromatography on SiO2 (Hex:EtOAc=3:1) to give 5-bromo-2-chloro-3-nitropyridine (4.24 g, 85%) as a yellow solid. 1H-NMR (CDCl3, Varian 400 MHz) δ 8.37 (1H, d, J=2.4 Hz), 8.70 (1H, d, J=2.0 Hz).

Step B: 5-bromo-2-chloropyridin-3-amine

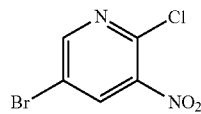 [SMILES: O=[N+]([O-])c1cc(Br)cnc1Cl]

To a solution of 5-bromo-2-chloro-3-nitropyridine (4.24 g, 17.86 mmol) in EtOH (89 ml) was added Tin(II) chloride (16.9 g, 89.0 mmol) at room temperature. The mixture was refluxed for 1 hour, and then cooled to room temperature, filtered through a Celite pad and washed with EtOAc. The filtrate was concentrated in vacuo. The residue was treated with saturated aq. NaHCO3, and extracted with EtOAc. The combined organic layers were washed brine, dried over anhydrous Na2SO4, filtered and concentrated in vacuo. The residue was purified by column chromatography on SiO2 (Hex:EtOAc=3:1) to give 5-bromo-2-chloropyridin-3-amine (2.7 g, 73%) as a white solid. 1H-NMR (CDCl3, Varian 400 MHz) δ 5.89 (2H, brs), 7.30 (1H, d, J=2.0 Hz), 7.66 (1H, d, J=2.4 Hz).

Step C: N-(5-bromo-2-chloropyridin-3-yl)-2,4-difluorobenzenesulfonamide

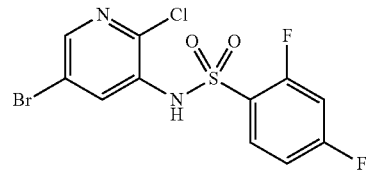 [SMILES: O=S(=O)(Nc1cc(Br)cnc1Cl)c1ccc(F)cc1F]

To a solution of 5-bromo-2-chloropyridin-3-amine (0.900 g, 4.34 mmol) in DCM (8.68 ml) was added pyridine (0.541 ml, 6.69 mmol) and 2,4-difluorobenzene-1-sulfonyl chloride (0.851 ml, 6.33 mmol) at 0° C. After stirring overnight at room temperature, the reaction mixture was diluted with DCM and treated with saturated aq. NaHCO3. The resulting solid was collected by filtration and washed with water to give N-(5-bromo-2-chloropyridin-3-yl)-N-(2,4-difluorophenylsulfonyl)-2,4-difluorobenzenesulfonamide (0.65 g, 27%) as a white solid. The filtrate was extracted with DCM (2×50 mL), the combined organic layers were washed brine, dried over anhydrous Na2SO4, filtered and concentrated in vacuo. The residue was purified by column chromatography on SiO2 (Hex:EtOAc=5:1) to give N-(5-bromo-2-chloropyridin-3-yl)-2,4-difluorobenzenesulfonamide (0.20 g, 12%) as a white solid. 1H-NMR (CDCl3, Varian 400 MHz) δ 7.26 (1H, t, J=8.4 Hz), 7.59 (1H, t, J=10.0 Hz), 7.81 (1H, dd, J=16.0, 7.6 Hz), 8.04 (1H, d, J=2.4 Hz), 8.46 (1H, d, J=2.4 Hz), 11.1 (1H, brs).

Step D: N-(2-chloro-5-(4,4,5,5-tetramethyl-1,3,2-dioxaborolan-2-yl)pyridin-3-yl)-2,4-difluorobenzenesulfonamide

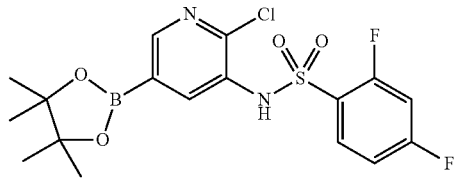 [SMILES: CC1(C)OB(c2cnc(Cl)c(NS(=O)(=O)c3ccc(F)cc3F)c2)OC1(C)C]

A mixture of N-(5-bromo-2-chloropyridin-3-yl)-2,4-difluorobenzenesulfonamide (1.12 g, 2.92 mmol), potassium acetate (1.14 g, 11.6 mmol), BISPIN (0.890 g, 3.50 mmol) and PdCl2(dppf)-CH2Cl2Adduct (0.119 g, 0.146 mmol) in dioxane (6.87 ml) was refluxed for 3 hours. After cooling to room temperature, the reaction mixture was filtered through a Celite pad and washed with CH2Cl2. The filtrate was diluted with water and extracted with CH2Cl2 (2×100 mL). The combined organic layers were washed with brine, dried over anhydrous Na2SO4, filtered and concentrated in vacuo. The residue was purified by column chromatography on SiO2 (Hex:EtOAc=5:1) to give N-(2-chloro-5-(4,4,5,5-tetramethyl-1,3,2-dioxaborolan-2-yl)pyridin-3-yl)-2,4-difluorobenzenesulfonamide (0.835 g, 66%) as a brown oil. 1H-NMR (CDCl3, Varian 400 MHz) δ 1.30 (12H, s), 6.88-

6.95 (2H, m), 7.79-7.85 (1H, m), 8.20 (1H, d, J=1.6 Hz), 8.40 (1H, d, J=1.6 Hz), 7.63 (1H, brs); NH peak was not observed.

Intermediate 4

N-(5-(4,4,5,5-tetramethyl-1,3,2-dioxaborolan-2-yl) pyridin-3-yl)-2,4-difluoro Benzenesulfonamide

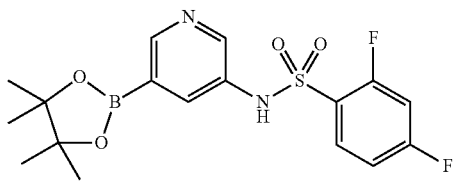 [SMILES: CC1(C)OB(c2cncc(NS(=O)(=O)c3ccc(F)cc3F)c2)OC1(C)C]

Step A: N-(5-bromopyridin-3-yl)-2,4-difluorobenzenesulfonamide

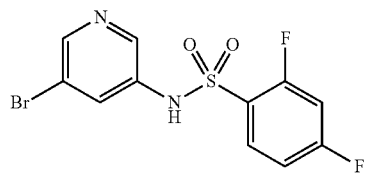 [SMILES: O=S(=O)(Nc1cncc(Br)c1)c1ccc(F)cc1F]

To a solution of 5-bromo-2-chloropyridin-3-amine (0.500 g, 2.89 mmol) in pyridine (1.45 ml) was dropwise added 2,4-difluorobenzene-1-sulfonyl chloride (0.614 ml, 2.89 mmol) at 0° C. The mixture was stirred for 40 min at room temperature and acidified with 1 N HCl. The residue was extracted with EtOAc and the combined organic layers were washed with brine, dried over anhydrous Na2SO4, filtered and concentrated in vacuo to give N-(5-bromopyridin-3-yl)-2,4-difluorobenzenesulfonamide (0.70 g, 70% yield) as a white solid. 1H-NMR (CDCl3, Varian 400 MHz) δ 6.92-7.04 (2H, m), 7.76-7.84 (1H, m), 7.86-7.95 (1H, m), 8.27 (1H, d, J=2.4 Hz), 8.44 (1H, d, J=2.4 Hz); NH peak was not observed.

Step B: N-(5-(4,4,5,5-tetramethyl-1,3,2-dioxaborolan-2-yl)pyridin-3-yl)-2,4-difluorobenzene sulfonamide

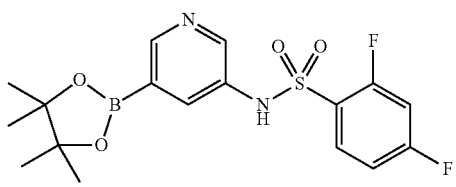 [SMILES: CC1(C)OB(c2cncc(NS(=O)(=O)c3ccc(F)cc3F)c2)OC1(C)C]

A mixture of N-(5-bromo-2-chloropyridin-3-yl)-2,4-difluorobenzenesulfonamide (0.70 g, 2.01 mmol), Potassium acetate (0.590 g, 6.01 mmol), BISPIN (0.611 g, 2.41 mmol) and PdCl2(dppf)-CH2Cl2Adduct (0.164 g, 0.200 mmol) in dioxane (7.51 ml) was refluxed for 3 hours. After cooling to room temperature, the reaction mixture was filtered through a Celite pad and washed with CH2Cl2. The filtrate was diluted with water and extracted with CH2Cl2 (2×100 mL). The combined organic layers were washed with brine, dried over anhydrous Na2SO4, filtered and concentrated in vacuo. The residue was purified by column chromatography on SiO2 (Hex:EtOAc=5:1) to give N-(5-(4,4,5,5-tetramethyl-1,3,2-dioxaborolan-2-yl)pyridin-3-yl)-2,4-difluoro benzenesulfonamide (0.110 g, 14%) as a brown oil. 1H-NMR (CDCl3, Varian 400 MHz) δ 1.33 (12H, s), 6.86-6.95 (2H, m), 7.82-7.98 (2H, m), 8.46 (1H, d, J=2.8 Hz), 8.70 (1H, d, J=1.2 Hz); NH peak was not observed.

Intermediate 5

N-(2-chloro-5-(4,4,5,5-tetramethyl-1,3,2-dioxaborolan-2-yl)pyridin-3-yl)benzenesulfonamide

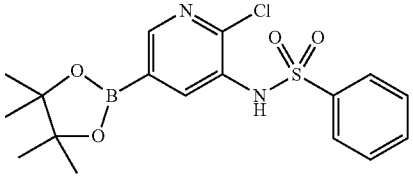 [SMILES: CC1(C)OB(c2cnc(Cl)c(NS(=O)(=O)c3ccccc3)c2)OC1(C)C]

Step A:
N-(5-bromo-2-chloropyridin-3-yl)benzenesulfonamide

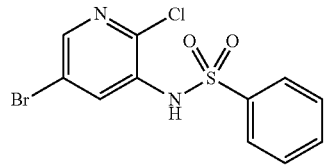 [SMILES: O=S(=O)(Nc1cc(Br)cnc1Cl)c1ccccc1]

To a solution of 5-bromo-2-chloropyridin-3-amine (1.00 g, 4.82 mmol) in pyridine (2.41 ml) was dropwise added benzenesulfonyl chloride (0.851 g, 4.82 mmol) at 0° C. The mixture was stirred for 40 min at room temperature and acidified with 1 N HCl. The residue was extracted with EtOAc and the combined organic layers were washed with brine, dried over anhydrous Na2SO4, filtered and concentrated in vacuo to give N-(5-bromo-2-chloropyridin-3-yl)-N-(phenylsulfonyl)benzenesulfonamide (0.606 g, 26% yield) as a white solid. 1H-NMR (CDCl3, Varian 400 MHz) δ 7.02 (1H, s), 7.47-7.56 (2H, m), 7.59-7.66 (1H, m), 7.78-7.86 (2H, m), 8.16 (2H, dd, J=2.4, 7.2 Hz).

Step B: N-(2-chloro-5-(4,4,5,5-tetramethyl-1,3,2-dioxaborolan-2-yl)pyridin-3-yl)benzene sulfon amide

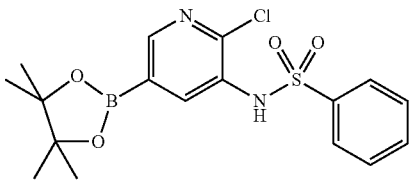 [SMILES: CC1(C)OB(c2cnc(Cl)c(NS(=O)(=O)c3ccccc3)c2)OC1(C)C]

A mixture of N-(5-bromo-2-chloropyridin-3-yl)benzenesulfonamide (0.100 g, 0.288 mmol), Potassium acetate (0.085 g, 0.863 mmol), BISPIN (0.080 g, 0.316 mmol) and PdCl2 (dppf)-CH2Cl2Adduct (0.023 g, 0.029 mmol) in dioxane (0.8 ml) was subjected to microwave irradiation for 1 hour at 110° C. After cooling to room temperature, the reaction mixture was filtered through a Celite pad and washed with CH2Cl2. The filtrate was diluted with water and extracted with CH2Cl2 (2×100 mL). The combined organic layers were washed with brine, dried over anhydrous Na2SO4, filtered and concentrated in vacuo to get N-(2-chloro-5-(4,4,5,5-tetramethyl-1,3,2-dioxaborolan-2-yl)pyridin-3-yl)benzenesulfonamide (quant.) as a brown solid, which was used for the next step without further purification.

Intermediate 6

6-chloro-4-(1-methylpiperidin-4-yloxy)pyrido[3,2-d]pyrimidine

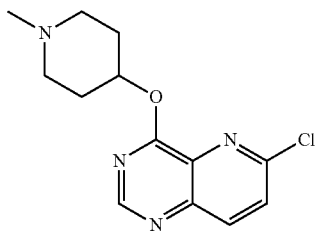 [SMILES: CN1CCC(Oc2ncnc3ccc(Cl)nc23)CC1]

To a solution of 1-methylpiperidin-4-ol (0.095 g, 0.825 mmol) in DMF (2.500 ml) was added NaH (0.041 g, 55% dispersion in mineral oil, 0.945 mmol) at 0° C. After stirring for 30 min at room temperature, the reaction mixture was cooled to 0° C., followed by the addition of 4,6-dichloropyrido[3,2-d]pyrimidine (Intermediate 1, step D) (0.15 g, 0.750 mmol). After stirring for 2 hours at room temperature, the reaction mixture was diluted with water, and extracted with EtOAc. The organic layers were dried over MgSO4, filtered and concentrated in vacuo. The residue was purified by column chromatography on SiO2 (Hex:EtOAc=5:1) to give 6-chloro-4-(1-methylpiperidin-4-yloxy)pyrido[3,2-d]pyrimidine (0.09 g, 43%) as a yellow solid. 1H-NMR (CDCl3, Varian 400 MHz) δ 2.03-2.12 (2H, m), 2.17-2.21 (2H, m), 2.22-2.32 (2H, m), 2.34 (3H, s), 2.84-2.89 (2H, m), 5.38-5.45 (1H, m), 7.73 (1H, d, J=8.8 Hz), 8.18 (1H, d, J=8.8 Hz), 8.81 (1H, s).

Intermediate 7 tert-butyl 4-(6-chloropyrido[3,2-d]pyrimidin-4-yloxy)piperidine-1-carboxylate

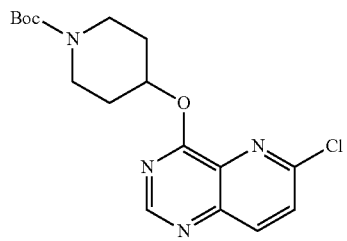 [SMILES: CC(C)(C)OC(=O)N1CCC(Oc2ncnc3ccc(Cl)nc23)CC1]

To a solution of tert-butyl 4-hydroxypiperidine-1-carboxylate (0.201 g, 1.000 mmol) in DMF (5.00 ml) was added NaH (0.052 g, 55% dispersion in mineral oil, 1.20 mmol) at 0° C. After stirring for 30 min at room temperature, the reaction mixture was cooled to 0° C. and 4,6-dichloropyrido[3,2-d]pyrimidine (Intermediate 1, step D) (0.2 g, 1.000 mmol) was added to the mixture. After stirring for 3 hours at room temperature, the reaction mixture was diluted with water, and extracted with EtOAc. The organic layers were dried over MgSO4, filtered and concentrated in vacuo. The residue was purified by column chromatography on SiO2 (Hex:EtOAc=5:1) to give tert-butyl 4-(6-chloropyrido[3,2-d]pyrimidin-4-yloxy)piperidine-1-carboxylate (0.236 g, 65%) as a white solid. 1H-NMR (CDCl3, Varian 400 MHz) δ 1.49 (9H, s), 1.91-1.99 (2H, m), 2.10-2.13 (2H, m), 3.21-3.27 (2H, m), 3.83-3.97 (2H, m), 5.55-5.62 (1H, m), 7.74 (1H, d, J=8.8 Hz), 8.19 (1H, d, J=8.8 Hz), 8.41 (1H, s).

Intermediate 8

6-chloro-4-(pyridin-3-yloxy)pyrido[3,2-d]pyrimidine

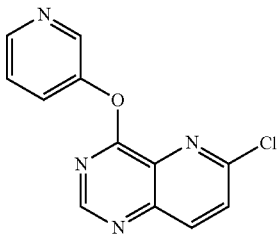 [SMILES: Clc1ccc2ncnc(Oc3cccnc3)c2n1]

To a solution of pyridin-3-ol (0.048 g, 0.500 mmol) in DMF (1.67 ml) was added NaH (0.027 g, 55% dispersion in mineral oil, 0.630 mmol) at 0° C. After stirring for 30 min at room temperature, the reaction mixture was cooled to 0° C. and 4,6-dichloropyrido[3,2-d]pyrimidine (Intermediate 1, step D) (0.1 g, 0.500 mmol) was added to the mixture. After stirring for 2 hours at room temperature, the reaction mixture was diluted with water, and extracted with EtOAc. The organic layers were dried over MgSO4, filtered and concentrated in vacuo. The residue was purified by column chromatography on SiO2 (Hex:EtOAc=5:1) to give 6-chloro-4-(pyridin-3-yloxy)pyrido[3,2-d]pyrimidine (0.090 g, 70%) as a white solid. 1H-NMR (CDCl3, Varian 400 MHz) δ 7.46 (1H, dd, J=8.0 and 4.8 Hz), 7.66-7.69 (1H, m), 7.86 (1H, d, J=8.8 Hz), 8.31 (1H, d, J=8.8 Hz), 8.61 (1H, d, J=4.4 Hz), 8.65 (1H, d, J=2.8 Hz), 8.80 (1H, s).

Intermediate 9

6-(4,4,5,5-tetramethyl-1,3,2-dioxaborolanyl)-2-(N,N-bis(boc-amino))pyrazine

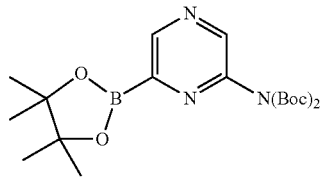

Step A: 6-chloro-2-(N,N-bis(boc-amino)pyrazine

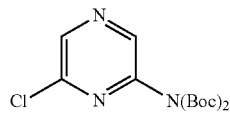

To a solution of 6-chloropyrazin-2-amine (0.3 g, 2.31 mmol) in THF (11.5 ml) was added (Boc)2O (1.34 ml, 5.79 mmol) and DMAP (0.141 g, 1.16 mmol) at room temperature. After stirring for 2 hours at room temperature, the reaction mixture was concentrated in vacuo. The residue was purified by column chromatography on SiO2 (Hex:EtOAc=4:1) to give 6-chloro-2-(N,N-bis(boc-amino)pyrazine (0.747 g, 98%) as a white solid. 1H-NMR (CDCl3, Varian 400 MHz) δ 1.47 (18H, s), 8.48 (1H, d, J=0.8 Hz), 8.53 (1H, d, J=0.8 Hz).

Step B: 6-(4,4,5,5-tetramethyl-1,3,2-dioxaborolanyl)-2-(N,N-Bis(Boc-amino))-pyrazine

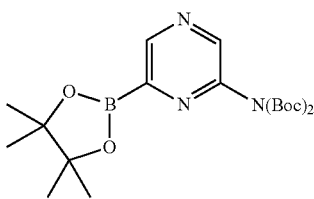

A mixture of 6-chloro-2-(N,N-bis(boc-amino)pyrazine (0.10 g, 0.303 mmol), bis(pinacolato) diboron (0.085 g, 0.334 mmol), potassium acetate (0.089 g, 0.910 mmol) and PdCl2(dppf)-CH2Cl2Adduct (0.012 g, 0.015 mmol) in dioxane (1.52 ml) was subjected to microwave irradiation for 1 hour at 110° C., and cooled to room temperature. The reaction mixture was filtered through a Celite pad and washed with CH2Cl2. The filtrate was concentrated in vacuo to give 6-(4,4,5,5-tetramethyl-1,3,2-dioxaborolanyl)-2-(N,N-Bis(Boc-amino))pyrazine (0.128 g, quant) as a brown oil, which was used for the next step without further purification. 1H-NMR (CDCl3, Varian 400 MHz) δ 1.39 (12H, s), 1.42 (12H, s), 8.52 (1H, s), 8.86 (1H, s).

Intermediate 10

6-(4-(tetrahydro-2H-pyran-4-yloxy)pyrido[3,2-d]pyrimidin-6-yl)-2-(N,N-Bis(Boc-amino))-pyrazine

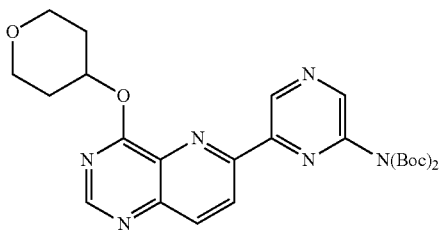

A mixture of 6-(4,4,5,5-tetramethyl-1,3,2-dioxaborolanyl)-2-(N,N-bis(boc-amino))pyrazine (0.872 g, 2.070 mmol) (Intermediate 9), 6-chloro-4-(tetrahydro-2H-pyran-4-yloxy) pyrido[3,2-d]pyrimidine (0.5 g, 1.882 mmol) (Intermediate 1), PdCl2(dppf)-CH2Cl2Adduct (0.154 g, 0.188 mmol) and 1N aq. sodium bicarbonate (3.76 ml, 3.76 mmol) in dioxane (9.41 ml) was refluxed for 1 hour. The reaction mixture was cooled to room temperature, and the reaction mixture was filtered through a pad of Celite and washed with CH2Cl2. The filtrate was diluted with water and extracted with CH2Cl2 (2×100 mL). The combined organic layers were washed with brine, dried over anhydrous Na2SO4, filtered and concentrated in vacuo. The residue was purified by column chromatography on SiO2 (Hex:EtOAc=1:1) to give 6-(4-(tetrahydro-2H-pyran-4-yloxy)pyrido[3,2-d]pyrimidin-6-yl)-2-(N,N-bis(boc-amino))pyrazine (0.845 g, 86%) as a yellow solid. 1H-NMR (CDCl3, Varian 400 MHz) δ 1.27 (18H, s), 2.05-2.13 (2H, m), 2.17-2.19 (2H, m), 3.71-3.77 (2H, m), 4.12-4.17 (2H, m), 5.67-5.71 (1H, m), 8.39 (1H, d, J=8.8 Hz), 8.69 (1H, s), 8.78 (1H, d, J=8.8 Hz), 8.85 (1H, s), 9.77 (1H, s).

Intermediate 11

4-bromo-2-chloro-N-(5-(4,4,5,5-tetramethyl-1,3,2-dioxaborolan-2-yl)pyridin-3-yl)benzene sulfonamide

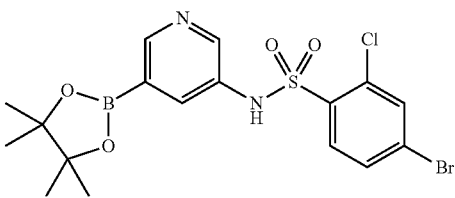 [SMILES: CC1(C)OB(c2cncc(NS(=O)(=O)c3ccc(Br)cc3Cl)c2)OC1(C)C]

Step A: 4-bromo-N-(5-bromopyridin-3-yl)-2-chlorobenzenesulfonamide

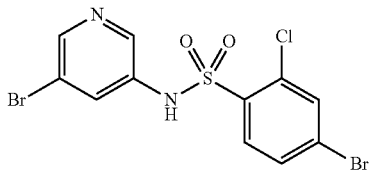 [SMILES: O=S(=O)(Nc1cncc(Br)c1)c1ccc(Br)cc1Cl]

To a solution of 5-bromopyridin-3-amine (0.300 g, 1.73 mmol) in pyridine (8.67 ml) was slowly added 4-bromo-2-chlorobenzene-1-sulfonyl chloride (0.600 g, 2.08 mmol) at 0° C. The reaction mixture was stirred for 2 hours at room temperature. The reaction mixture was quenched with 1 N aq. HCl, and then extracted with DCM (2×50 mL). The combined organic layers were washed brine, dried over anhydrous MgSO4, filtered and concentrated in vacuo. The resulting residue was recrystallized from EtOAc-hexanes to give 4-bromo-N-(5-bromopyridin-3-yl)-2-chlorobenzenesulfonamide (0.530 g, 72%) as a red solid. 1H-NMR (CDCl3, Varian 400 MHz) δ 7.53-7.55 (1H, m), 7.71 (1H, d, J=1.6 Hz), 7.78 (1H, t, J=2.2 Hz), 7.89 (1H, d, J=8.4 Hz), 8.26 (1H, d, J=2.0 Hz). 8.44 (1H, d, J=2.4 Hz).

Step B: 4-bromo-2-chloro-N-(5-(4,4,5,5-tetramethyl-1,3,2-dioxaborolan-2-yl)pyridin-3-yl)benzenesulfonamide

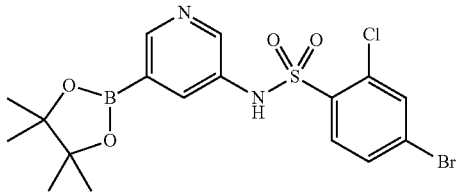 [SMILES: CC1(C)OB(c2cncc(NS(=O)(=O)c3ccc(Br)cc3Cl)c2)OC1(C)C]

A mixture of 4-bromo-N-(5-bromopyridin-3-yl)-2-chlorobenzenesulfonamide (0.330 g, 0.774 mmol), bis(pinacolato)diboron (0.216 g, 0.851 mmol), potassium acetate (0.228 g, 2.32 mmol) and PdCl2(dppf)-CH2Cl2 (0.0320 g, 0.039 mmol) in dioxane (3.87 ml) was refluxed for 4 hours, and cooled to room temperature. The reaction mixture was filtered through a Celite pad and washed with DCM. The combined organic layers were washed brine, dried over anhydrous MgSO4, filtered and concentrated in vacuo. The residue was purified by column chromatography on SiO2 (Hex: EtOAc=10:1) to give 4-bromo-2-chloro-N-(5-(4,4,5,5-tetramethyl-1,3,2-dioxaborolan-2-yl)pyridin-3-yl)benzenesulfonamide (0.145 g, 40%) as a yellow solid. 1H-NMR (CDCl3, Varian 400 MHz): δ 1.34 (12H, s), 7.35 (1H, s), 7.76-7.78 (2H, m), 7.92 (1H, s), 8.00 (1H, d, J=8.0 Hz), 8.24 (1H, d, J=2.4 Hz), 8.40 (1H, d, J=2.0 Hz).

Intermediate 12

5-(4-(tetrahydro-2H-pyran-4-yloxy)pyrido[3,2-d]pyrimidin-6-yl)pyridin-3-amine

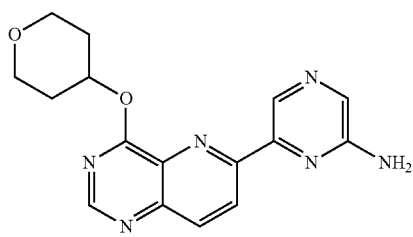 [SMILES: Nc1cncc(-c2ccc3ncnc(OC4CCOCC4)c3n2)n1]

Step A: 5-bromo-3-(N,N-bis(boc-amino)pyridine

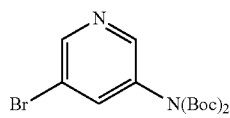

To a solution of 5-bromopyridin-3-amine (2.00 g, 11.6 mmol) in THF (57.8 ml) were added (Boc)2O (6.44 ml, 27.7 mmol) and DMAP (0.706 g, 5.78 mmol) at room temperature. After stirred for 2 hours at room temperature, the reaction mixture was concentrated in vacuo. The residue was purified by column chromatography on SiO2 (Hex:EtOAc=30:1) to give 5-bromo-3-(N,N-bis(boc-amino)pyridine (3.00 g, 70%) as a yellow solid. 1H-NMR (CDCl3, Varian 400 MHz) δ 1.44 (18H, s), 7.68 (1H, t, J=2.2 Hz), 8.36 (1H, d, J=2.4 Hz), 8.60 (1H, d, J=2.0 Hz)

Step B: 5-(4,4,5,5-tetramethyl-1,3,2-dioxaborolan-2-yl)-3-(N,N-bis(boc-amino)pyridine

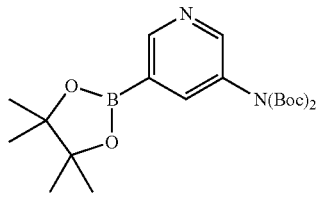

A mixture of 5-bromo-3-(N,N-bis(boc-amino)pyridine (0.100 g, 0.268 mmol), BISPIN (0.075 g, 0.295 mmol), potassium acetate (0.079 g, 0.804 mmol) and PdCl2(dppf)-CH2Cl2 (10.9 mg, 0.013 mmol) in dioxane (1.340 ml) was subjected to microwave irradiation for 1 hour at 110° C., and cooled to room temperature. The reaction mixture was filtered through a Celite pad and washed with DCM. The filtrate was concentrated in vacuo to give 5-(4,4,5,5-tetramethyl-1,3,2-dioxaborolan-2-yl)-3-(N,N-bis(boc-amino)pyridine (0.113 g, quant) as a yellow solid, which was used for the next step without further purification. 1H-NMR (CDCl3, Varian 400 MHz) δ 1.27 (9H, s), 1.36 (9H, s), 1.43 (12H, s), 7.85-7.86 (1H, m), 8.47 (1H, d, J=2.8 Hz), 8.84 (1H, d, J=1.6 Hz).

Step C: 5-(4-(tetrahydro-2H-pyran-4-yloxy)pyrido[3,2-d]pyrimidin-6-yl)-3-(N,N-bis(boc-amino)pyridine

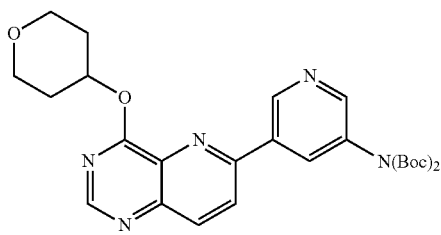

A mixture of 5-(4,4,5,5-tetramethyl-1,3,2-dioxaborolan-2-yl)-3-(N,N-bis(boc-amino)pyridine (0.1 g, 0.238 mmol), BISPIN (0.070 g, 0.262 mmol), 1N aq. sodium bicarbonate (0.476 ml, 0.476 mmol) and PdCl2(dppf)-CH2Cl2 (0.019 g, 0.024 mmol) in dioxane (1.20 ml) was subjected to microwave irradiation for 1 hour at 110° C., and cooled to room temperature. The reaction mixture was filtered through a Celite pad and washed with DCM. The residue was purified by column chromatography on SiO2 (Hex:EtOAc=1:1) to give 5-(4-(tetrahydro-2H-pyran-4-yloxy)pyrido[3,2-d]pyrimidin-6-yl)-3-(N,N-bis(boc-amino)pyridine (0.09 g, 89%) as a brown solid. 1H-NMR (CDCl3, Varian 400 MHz) δ 1.55 (9H, s), 2.03-2.11 (2H, m), 2.22-2.26 (2H, m), 3.64-3.79 (2H, m), 4.10-4.16 (2H, m), 5.64-5.69 (1H, m), 7.16 (1H, s), 8.27 (1H, d, J=8.8 Hz), 8.34 (1H, d, J=8.8 Hz), 8.65 (1H, s), 8.80-8.72 (2H, m), 9.09 (1H, s).

Step D: 5-(4-(tetrahydro-2H-pyran-4-yloxy)pyrido[3,2-d]pyrimidin-6-yl)pyridin-3-amine

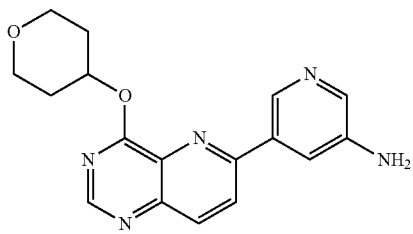 [SMILES: Nc1cncc(-c2ccc3ncnc(OC4CCOCC4)c3n2)c1]

To a solution of 5-(4-(tetrahydro-2H-pyran-4-yloxy)pyrido[3,2-d]pyrimidin-6-yl)-3-(N,N-bis(boc-amino)pyridine (0.500 g, 0.955 mmol) in DCM (4.77 ml) was slowly added TFA (2.207 ml, 28.6 mmol) at 0° C. After stirred for 4 hours at room temperature, the reaction mixture was quenched with 1N aq. NaOH, extracted with DCM. The organic layers was dried over MgSO4, filtered and concentrated in vacuo to give 5-(4-(tetrahydro-2H-pyran-4-yloxy)pyrido[3,2-d]pyrimidin-6-yl)pyridin-3-amine (0.309 g, quant) as a yellow solid, which was used for the next step without further purification. 1H-NMR (CDCl3, Varian 400 MHz) δ 2.04-2.12 (2H, m), 2.23-2.28 (2H, m), 3.67-3.74 (2H, m), 3.91 (2H, s), 4.10-4.15 (2H, m), 5.63-5.70 (1H, m), 7.85-7.86 (1H, s), 8.21-8.24 (2H, m), 8.32 (1H, d, J=8.8 Hz), 8.73 (1H, d, J=2.0 Hz), 8.81 (1H, s).

Intermediate 13

N-(5-(4,4,5,5-tetramethyl-1,3,2-dioxaborolan-2-yl)pyridin-3-yl)benzamide

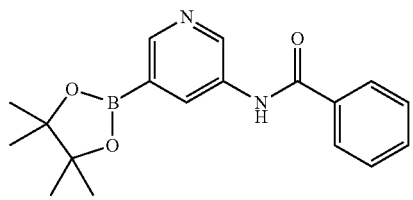 [SMILES: CC1(C)OB(c2cncc(NC(=O)c3ccccc3)c2)OC1(C)C]

Step A: N-(5-bromopyridin-3-yl)benzamide

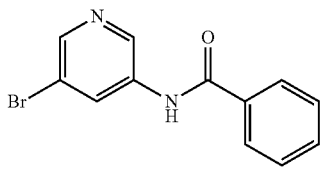 [SMILES: O=C(Nc1cncc(Br)c1)c1ccccc1]

To a solution of 5-bromopyridin-3-amine (0.3 g, 1.734 mmol) in THF (8.67 ml) was added TEA (0.363 ml, 2.60 mmol), and then benzoyl chloride (0.292 g, 2.081 mmol) was added to the mixture at 0° C. After stirred for 2 hours at room temperature, the reaction mixture was quenched with saturated aq. NaHCO3 (50 mL) and extracted with EtOAc (2×50 mL). The combined organic layers were washed with water and brine, dried over anhydrous Na2SO4, filtered and concentrated in vacuo. The residue was purified by column chromatography on SiO2 (Hex:EtOAc=10:1) to give N-(5-bromopyridin-3-yl)benzamide (0.435 g, 91%) as a yellow solid. 1H-NMR (CDCl3, Varian 400 MHz) δ 7.48 (2H, t, J=7.6 Hz), 7.58 (1H, t, J=7.4 Hz), 7.85-7.88 (2H, m), 8.38 (1H, brs), 8.40 (1H, d, J=1.6 Hz), 8.56-8.58 (2H, m).

Step B: N-(5-(4,4,5,5-tetramethyl-1,3,2-dioxaborolan-2-yl)pyridin-3-yl)benzamide

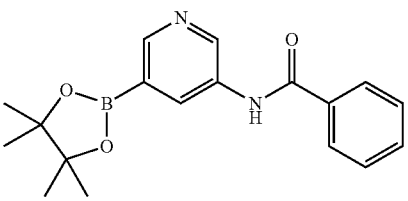 [SMILES: CC1(C)OB(c2cncc(NC(=O)c3ccccc3)c2)OC1(C)C]

A mixture of N-(5-bromopyridin-3-yl)benzamide (0.435 g, 1.57 mmol), BISPIN (0.438 g, 1.73 mmol), potassium acetate (0.462 g, 4.71 mmol) and PdCl2(dppf)-CH2Cl2 (0.064 g, 0.078 mmol) in dioxane (7.85 ml) was refluxed for 2 hours, and cooled to room temperature. The reaction mixture was filtered through a Celite pad and washed with DCM. The combined organic layers were washed brine, dried over anhydrous MgSO4, filtered and concentrated in vacuo. The residue was purified by column chromatography on SiO2 (Hex:EtOAc=1:1) to give N-(5-(4,4,5,5-tetramethyl-1,3,2-dioxaborolan-2-yl)pyridin-3-yl)benzamide (0.247 g, 49%) as a yellow oil. 1H-NMR (CDCl3, Varian 400 MHz) δ 1.36 (12H, s), 7.38-7.58 (4H, m), 7.90 (2H, d, J=7.2 Hz), 8.45 (1H, s), 8.72 (1H, s), 8.95 (1H, s).

Intermediate 14

N-(2-chloro-5-(4,4,5,5-tetramethyl-1,3,2-dioxaborolan-2-yl)pyridin-3-yl)-2,4-difluoro benzamide

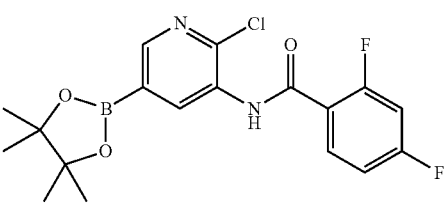 [SMILES: CC1(C)OB(c2cnc(Cl)c(NC(=O)c3ccc(F)cc3F)c2)OC1(C)C]

Step A: 2,4-difluorobenzoyl chloride

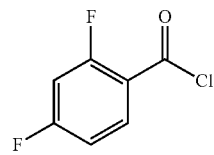

To a solution of 2,4-difluorobenzoic acid (0.100 g, 0.633 mmol) in DCM (3.16 ml) were added oxalyl chloride (0.066 ml, 0.759 mmol) and DMF (0.490 µl, 6.33 µmol) at 0° C. The reaction mixture was stirred for overnight at room temperature. The reaction mixture was concentrated in vacuo, which was used for the next step without further purification. 1H-NMR (CDCl3, Varian 400 MHz) δ 6.92-9.98 (1H, m), 7.01-7.06 (1H, m), 8.16-8.22 (1H, m).

Step B: N-(5-bromo-2-chloropyridin-3-yl)-2,4-difluorobenzamide

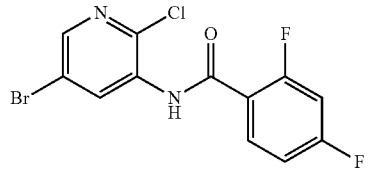 [SMILES: O=C(Nc1cc(Br)cnc1Cl)c1ccc(F)cc1F]

To a solution of 2,4-difluorobenzoyl chloride (0.33 g, 1.591 mmol) in CHCl3 (15.9 ml) were slowly added TEA (0.443 ml, 3.18 mmol) and 5-bromo-2-chloropyridin-3-amine (0.337 g, 1.91 mmol) at 0° C. The reaction mixture was stirred for 5 hours at room temperature. The reaction mixture was quenched with saturated aq. NaHCO3, and extracted with DCM (2×50 mL). The combined organic layers were washed brine, dried over anhydrous MgSO4, filtered and concentrated in vacuo. The residue was purified by column chromatography on SiO2 (Hex:EtOAc=30:1) to give N-(5-bromo-2-chloropyridin-3-yl)-2,4-difluorobenzamide (0.185 g, 34%) as a white solid. 1H-NMR (CDCl3, Varian 400 MHz) δ 6.93-7.26 (2H, m), 8.21-8.27 (2H, m), 9.08-9.12 (1H, m), 9.16-9.16 (1H, m).

Step C: N-(2-chloro-5-(4,4,5,5-tetramethyl-1,3,2-dioxaborolan-2-yl)pyridin-3-yl)-2,4-difluorobenzamide

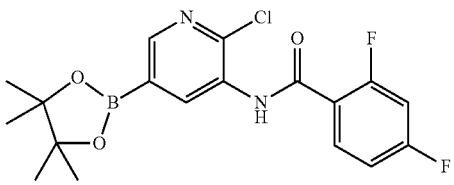 [SMILES: CC1(C)OB(c2cnc(Cl)c(NC(=O)c3ccc(F)cc3F)c2)OC1(C)C]

A mixture of N-(5-bromo-2-chloropyridin-3-yl)-2,4-difluorobenzamide (0.127 g, 0.365 mmol), BISPIN (0.102 g, 0.402 mmol), potassium acetate (0.108 g, 1.10 mmol) and PdCl2(dppf)-CH2Cl2 (0.015 g, 0.018 mmol) in dioxane (1.83 ml) was refluxed for 2 hours, and cooled to room temperature. The reaction mixture was filtered through a Celite pad and washed with DCM. The combined organic layers were washed brine, dried over anhydrous MgSO4, filtered and concentrated in vacuo. The residue was purified by column chromatography on SiO2 (only EtOAc) to give N-(2-chloro-5-(4,4,5,5-tetramethyl-1,3,2-dioxaborolan-2-yl)pyridin-3-yl)-2,4-difluorobenzamide (0.127 g, 88%) as a white solid. 1H-NMR (CDCl3, Varian 400 MHz) δ 1.36 (12H, s), 6.96-7.02 (1H, m), 7.07-7.12 (1H, m), 8.22-8.28 (1H, m), 8.48 (1H, s), 9.03-9.07 (1H, m), 9.17 (1H, s).

Intermediate 15

6-chloro-4-(cyclohexylthio)pyrido[3,2-d]pyrimidine

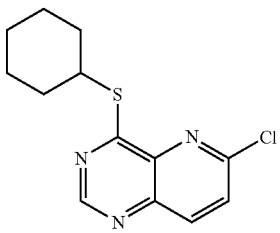 [SMILES: Clc1ccc2ncnc(SC3CCCCC3)c2n1]

To a solution of 4,6-dichloropyrido[3,2-d]pyrimidine (Intermediate 1, step D) (0.1 g, 0.500 mmol) in ACN (2.500 ml) were added cyclohexanethiol (0.058 g, 0.500 mmol) and K2CO3 (0.069 g, 0.500 mmol) at room temperature. After stirring overnight at room temperature, the reaction mixture was diluted with water and extracted with EtOAc (2×50 mL). The combined organic layers were washed with 1N aq. NaOH and then washed with 1N aq. HCl. The organic layers were dried over anhydrous MgSO4, filtered and concentrated in vacuo. The residue was purified by column chromatography on SiO2 (Hex:EtOAc=5:1) to give 6-chloro-4-(cyclo hexylthio)pyrido[3,2-d]pyrimidine (0.129 g, 92%) as a yellow solid. 1H-NMR (CDCl3, Varian 400 MHz) δ 1.36-1.42 (1H, m), 1.48-1.69 (5H, m), 1.80-1.86 (2H, m), 2.14-2.20 (2H, m), 4.10-4.16 (1H, m), 7.73 (1H, d, J=8.8 Hz), 8.19 (1H, d, J=8.8 Hz), 8.98 (1H, s).

Intermediate 16

6-chloro-4-(cyclopentyloxy)pyrido[3,2-d]pyrimidine

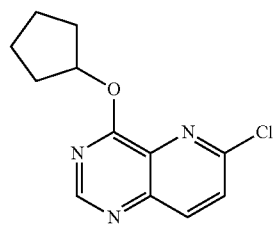 [SMILES: Clc1ccc2ncnc(OC3CCCC3)c2n1]

To a solution of cyclopentanol (0.050 ml, 0.550 mmol) in DMF (2.500 ml) was added NaH (0.026 g, 55% dispersion in mineral oil, 0.600 mmol) at 0° C. The reaction mixture was stirred for 30 min. at room temperature, 4,6-dichloropyrido[3,2-d]pyrimidine (Intermediate 1, step D) (0.1 g, 0.500 mmol) was added to the mixture at 0° C. After being stirred for 2 hours at room temperature, the reaction mixture was diluted with water, and extracted with EtOAc. The organic layers were dried over MgSO4 filtered and concentrated in vacuo. The residue was purified by column chromatography on SiO2 (Hex:EtOAc=5:1) to give 6-chloro-4-(cyclopentyloxy)pyrido[3,2-d]pyrimidine (0.04 g, 32%) as a yellow solid. 1H-NMR (CDCl3, Varian 400 MHz): δ 1.63-1.74 (2H, m), 1.86-1.96 (2H, m), 1.99-2.07 (2H, m), 2.12-2.20 (2H, m), 5.72-5.77 (1H, m), 7.72 (1H, d, J=8.8 Hz), 8.18 (1H, d, J=8.8 Hz), 8.83 (1H, s).

Intermediate 17

6-chloro-N-(tetrahydro-2H-pyran-4-yl)pyrido[3,2-d]pyrimidin-4-amine

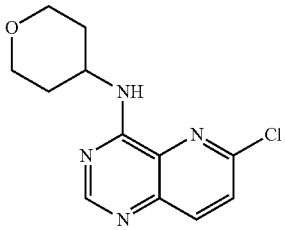 [SMILES: Clc1ccc2ncnc(NC3CCOCC3)c2n1]

A mixture of 4,6-dichloropyrido[3,2-d]pyrimidine (Intermediate 1, step D) (0.05 g, 0.250 mmol), tetrahydro-2H-pyran-4-amine (0.029 ml, 0.275 mmol), PdCl2(dppf)-CH2Cl2Adduct (2.041 mg, 2.500 μmol) and sodium tert-butoxide (0.048 g, 0.500 mmol) in dioxane (1.250 ml) was refluxed for 3 hours. After cooling to room temperature, the reaction mixture was filtered through a Celite pad and washed with CH2Cl2. The filtrate was concentrated in vacuo. The residue was purified by column chromatography on SiO2 (Hex:EtOAc=2:1) to give 6-chloro-N-(tetrahydro-2H-pyran-4-yl)pyrido[3,2-d]pyrimidin-4-amine (0.027 g, 41%) as a yellow solid.

1H-NMR (CDCl3, Varian 400 MHz) δ 1.68-1.78 (2H, m), 2.03-2.13 (2H, m), 3.58-3.67 (2H, m), 4.05-4.09 (2H, m), 4.36-4.46 (1H, m), 6.90 (1H, brs), 7.63 (1H, d, J=8.8 Hz), 8.05 (1H, d, J=8.8 Hz), 8.62 (1H, s).

Intermediate 18

6-chloro-N-cyclopentylpyrido[3,2-d]pyrimidin-4-amine

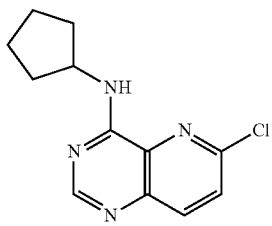 [SMILES: Clc1ccc2ncnc(NC3CCCC3)c2n1]

A mixture of 4,6-dichloropyrido[3,2-d]pyrimidine (Intermediate 1, step D) (0.100 g, 0.500 mmol), cyclopentanamine (0.054 ml, 0.550 mmol), PdCl2(dppf)-CH2Cl2Adduct (4.08 mg, 5.00 μmol) and sodium tert-butoxide (0.096 g, 1.00 mmol) in dioxane (2.50 ml) was refluxed for 3 hours. After cooling to room temperature, the reaction mixture was filtered through a Celite pad and washed with CH2Cl2. The filtrate was concentrated in vacuo. The residue was purified by column chromatography on SiO2 (Hex:EtOAc=1:1) to give 6-chloro-N-cyclopentylpyrido[3,2-d]pyrimidin-4-amine (0.043 g, 35%) as a yellow oil. 1H-NMR (CDCl3, Varian 400 MHz)): δ 1.60-1.83 (6H, m), 2.15-2.21 (2H, m), 4.55-4.60 (1H, m), 6.96 (1H, d, J=6.4 Hz), 7.59-7.62 (1H, m), 8.02-8.04 (1H, m), 8.63 (1H, s).

Intermediate 19

6-chloro-N-cyclobutylpyrido[3,2-d]pyrimidin-4-amine

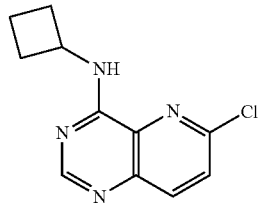 [SMILES: Clc1ccc2ncnc(NC3CCC3)c2n1]

A mixture of 4,6-dichloropyrido[3,2-d]pyrimidine (Intermediate 1, step D) (0.100 g, 0.500 mmol), cyclobutanamine (0.047 ml, 0.550 mmol), PdCl2(dppf)-CH2Cl2Adduct (4.08 mg, 5.00 μmol) and sodium tert-butoxide (0.096 g, 1.00 mmol) in dioxane (2.50 ml) was refluxed for 4 hours. After cooling to room temperature, the reaction mixture was filtered through a Celite pad and washed with CH2Cl2. The filtrate was concentrated in vacuo. The residue was purified by column chromatography on SiO2 (Hex:EtOAc=1:1) to give 6-chloro-N-cyclobutylpyrido[3,2-d]pyrimidin-4-amine (0.098 g, 84%) as a yellow solid. 1H-NMR (CDCl3, Varian 400 MHz) δ 1.79-1.89 (2H, m), 2.06-2.17 (2H, m), 2.48-2.56 (2H, m), 4.71-4.82 (1H, m), 7.11 (1H, brs), 7.61 (1H, d, J=8.8 Hz), 8.03 (1H, d, J=8.8 Hz), 8.61 (1H, s).

Intermediate 20

6-chloro-N-cyclopropylpyrido[3,2-d]pyrimidin-4-amine

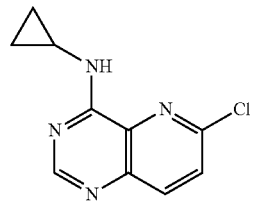 [SMILES: Clc1ccc2ncnc(NC3CC3)c2n1]

A mixture of 4,6-dichloropyrido[3,2-d]pyrimidine (Intermediate 1, step D) (0.100 g, 0.500 mmol), cyclopropanamine (0.038 ml, 0.550 mmol), PdCl2(dppf)-CH2Cl2Adduct (4.08 mg, 5.00 μmol) and sodium tert-butoxide (0.096 g, 1.00 mmol) in dioxane (2.50 ml) was refluxed for 4 hours. After cooling to room temperature, the reaction mixture was filtered through a Celite pad and washed with CH2Cl2. The filtrate was concentrated in vacuo. The residue was purified by column chromatography on SiO2 (Hex:EtOAc=1:1) to give 6-chloro-N-cyclopropylpyrido[3,2-d]pyrimidin-4-amine (0.060 g, 54%) as a yellow solid. 1H-NMR (CDCl3, Varian 400 MHz) δ 0.76-0.79 (2H, m), 0.99-1.03 (2H, m), 3.02-3.06 (1H, m), 7.12 (1H, brs), 7.61-7.63 (1H, m), 8.04-8.07 (1H, m), 8.73 (1H, s).

Intermediate 21

N-(6-chloropyrido[3,2-d]pyrimidin-4-yl)-3,5-dimethylisoxazol-4-amine

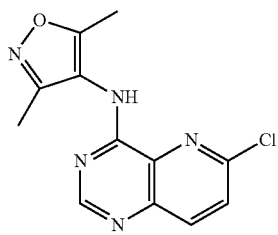 [SMILES: Cc1noc(C)c1Nc1ncnc2ccc(Cl)nc12]

A mixture of 4,6-dichloropyrido[3,2-d]pyrimidine (Intermediate 1, step D) (0.100 g, 0.500 mmol), 3,5-dimethylisoxazol-4-amine (0.140 g, 1.250 mmol) and sodium acetate (0.123 g, 1.50 mmol) in 5 ml of solvent (THF:H2O=1:1) was refluxed for 1 hour. The reaction mixture was diluted with EtOAc. The organics were washed with brine, dried over Na2SO4, filtered and concentrated. The crued was purified by column chromatography on SiO2 (Hex:EtOAc=1:1) to get N-(6-chloropyrido[3,2-d]pyrimidin-4-yl)-3,5-dimethylisoxazol-4-amine (0.082 g, 59%) as a yellow solid. 1H-NMR (CDCl3, Varian 400 MHz) δ 2.24 (3H, s), 2.40 (3H, s), 7.74 (1H, d, J=8.8 Hz), 7.93 (1H, brs), 8.16 ((1H, d, J=8.8 Hz), 8.69 (1H, s).

Intermediate 22

6-chloro-N-(6-methoxypyridin-3-yl)pyrido[3,2-d]pyrimidin-4-amine

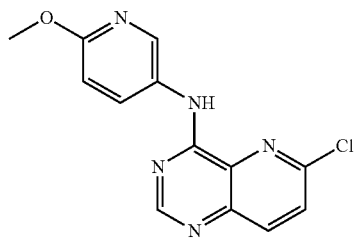 [SMILES: COc1ccc(Nc2ncnc3ccc(Cl)nc23)cn1]

A mixture of 4,6-dichloropyrido[3,2-d]pyrimidine (Intermediate 1, step D) (0.100 g, 0.500 mmol), 6-methoxypyridin-3-amine (0.155 g, 1.250 mmol) and sodium acetate (0.123 g, 1.50 mmol) in 5 ml of solvent (THF:H2O=1:1) was refluxed for 1 hour. The reaction mixture was diluted with EtOAc. The organics were washed with brine, dried over Na2SO4, filtered and concentrated. The crued was purified by column chromatography on SiO2 (Hex:EtOAc=1:1) to get 6-chloro-N-(6-methoxypyridin-3-yl)pyrido[3,2-d]pyrimidin-4-amine (0.085 g, 59%) as a yellow solid. 1H-NMR (CDCl3, Varian 400 MHz) δ 3.97 (3H, s), 6.85 (1H, d, J=8.8 Hz), 7.71 (1H, d, J=8.8 Hz), 8.14 (1H, d, J=8.8 Hz), 8.20 (1H, dd, J=2.8, 8.8 Hz), 8.55 (1H, d, J=2.8 Hz), 8.67 (1H, br s), 8.73 (1H, s).

Intermediate 23

6-chloro-N-(4-(trifluoromethoxy)phenyl)pyrido[3,2-d]pyrimidin-4-amine

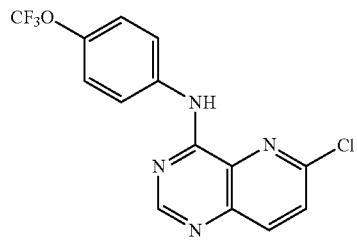

A mixture of 4,6-dichloropyrido[3,2-d]pyrimidine (Intermediate 1, step D) (0.200 g, 1.00 mmol), 4-(trifluoromethoxy)aniline (0.177 g, 1.00 mmol) and sodium acetate (0.246 g, 3.00 mmol) in 5 ml of solvent (THF:H2O=1:1) was refluxed for 1 hour. The reaction mixture was diluted with EtOAc. The organics were washed with brine, dried over Na2SO4, filtered and concentrated. The crued was purified by column chromatography on SiO2 (Hex:EtOAc=1:1) to get 6-chloro-N-(4-(trifluoromethoxy)phenyl)pyrido[3,2-d]pyrimidin-4-amine (0.32 g, 94%) as a yellow solid. 1H-NMR (CDCl3, Varian 400 MHz) δ 7.30 (1H, d, J=8.4 Hz), 7.72 (1H, d, J=8.8 Hz), 7.98 (1H, d, J=9.2 Hz), 8.15 (1H, dd, J=8.8 Hz), 8.80 (1H, s), 8.90 (1H, br s).

Intermediate 24 tert-butyl 4-(6-chloropyrido[3,2-d]pyrimidin-4-ylamino)piperidine-1-carboxylate

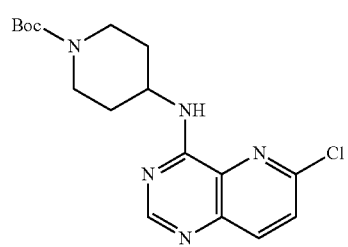 [SMILES: CC(C)(C)OC(=O)N1CCC(Nc2ncnc3ccc(Cl)nc23)CC1]

A mixture of 4,6-dichloropyrido[3,2-d]pyrimidine (Intermediate 1, step D) (0.100 g, 0.500 mmol), tert-butyl 4-aminopiperidine-1-carboxylate (0.110 g, 0.550 mmol), PdCl2(dppf)-CH2Cl2Adduct (4.08 mg, 5.00 μmol) and sodium tert-butoxide (0.096 g, 1.00 mmol) in dioxane (2.50 ml) was refluxed for 4 hours After cooling to room temperature, the reaction mixture was filtered through a Celite pad and washed with CH2Cl2. The filtrate was concentrated in vacuo. The residue was purified by column chromatography on SiO2 (Hex:EtOAc=1:1) to give tert-butyl 4-(6-chloropyrido[3,2-d]pyrimidin-4-ylamino)piperidine-1-carboxylate (0.089 g, 49%) as a yellow solid. 1H-NMR (CDCl3, Varian 400 MHz) δ 1.49 (9H, s), 1.52-1.75 (2H, m), 2.05-2.16 (2H, m), 2.92-3.10 (2H, m), 4.08-4.25 (2H, m), 4.35-4.42 (1H, m), 6.87 (1H, d, J=8.4 Hz), 7.63 (1H, d, J=8.8 Hz), 8.06 (1H, d, J=8.8 Hz), 8.62 (1H, s).

Synthetic Procedure 2-Formula Ia
The Preparation of Compounds of Formula Ia is Outlined Below:
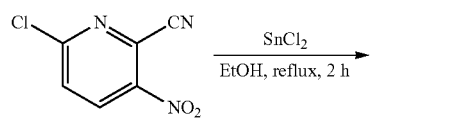
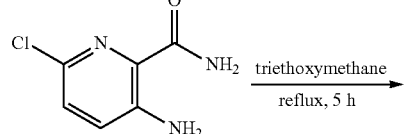
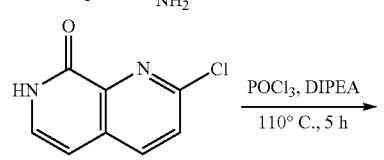
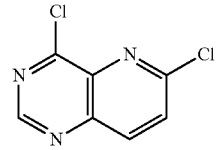
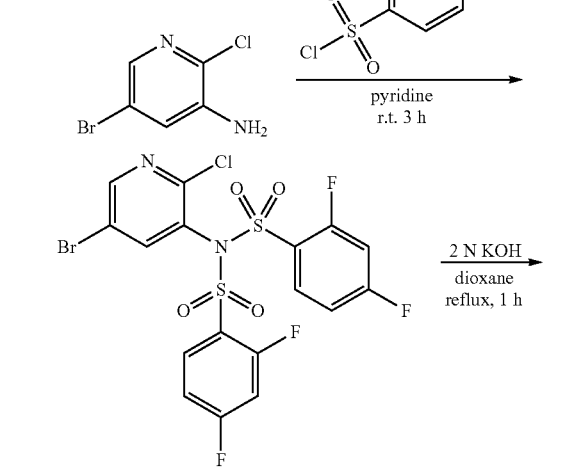
Scheme 2
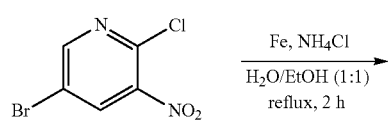
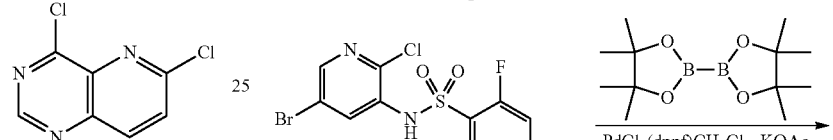
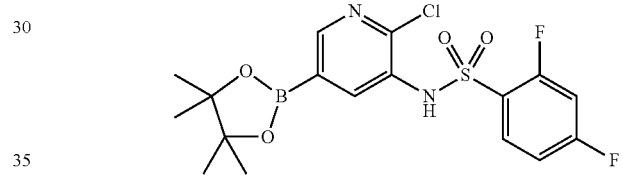
Scheme 3
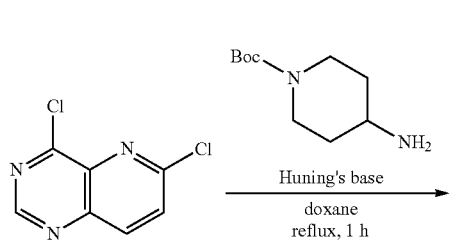
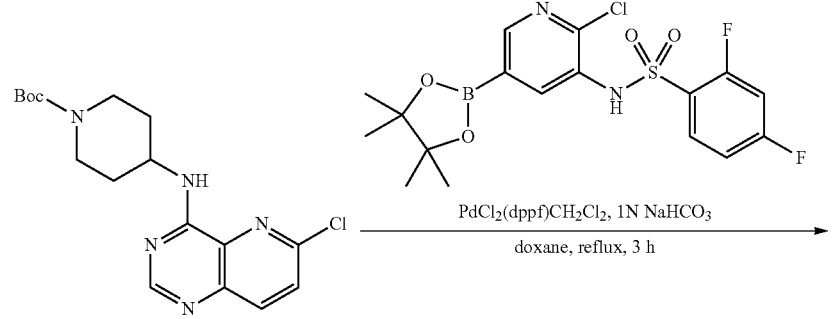

-continued
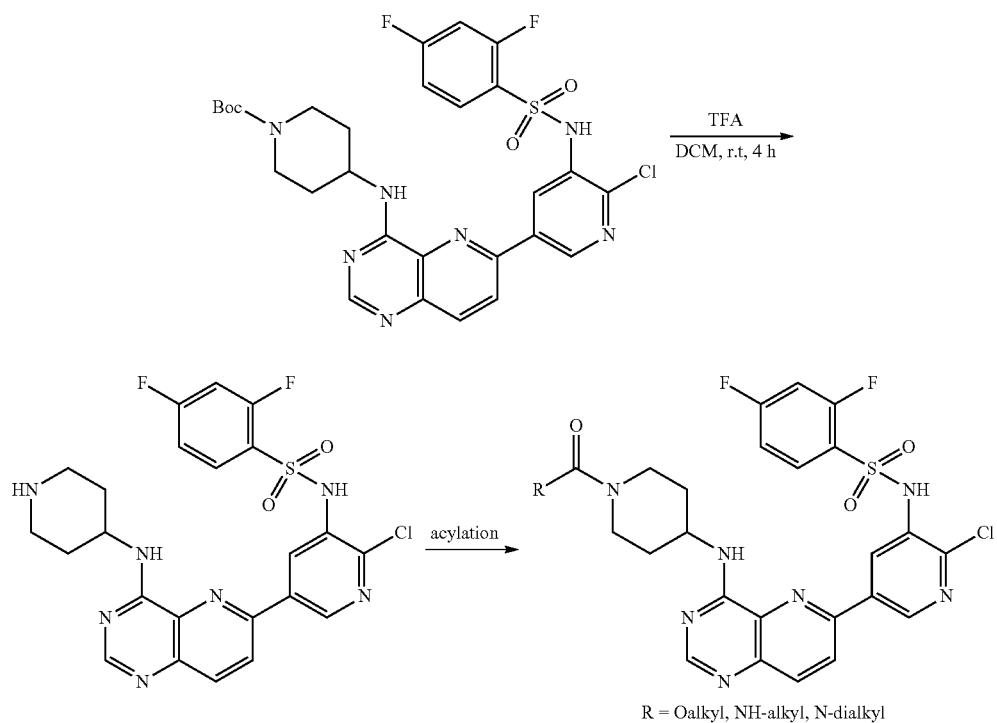
R = Oalkyl, NH-alkyl, N-dialkyl
Scheme 4
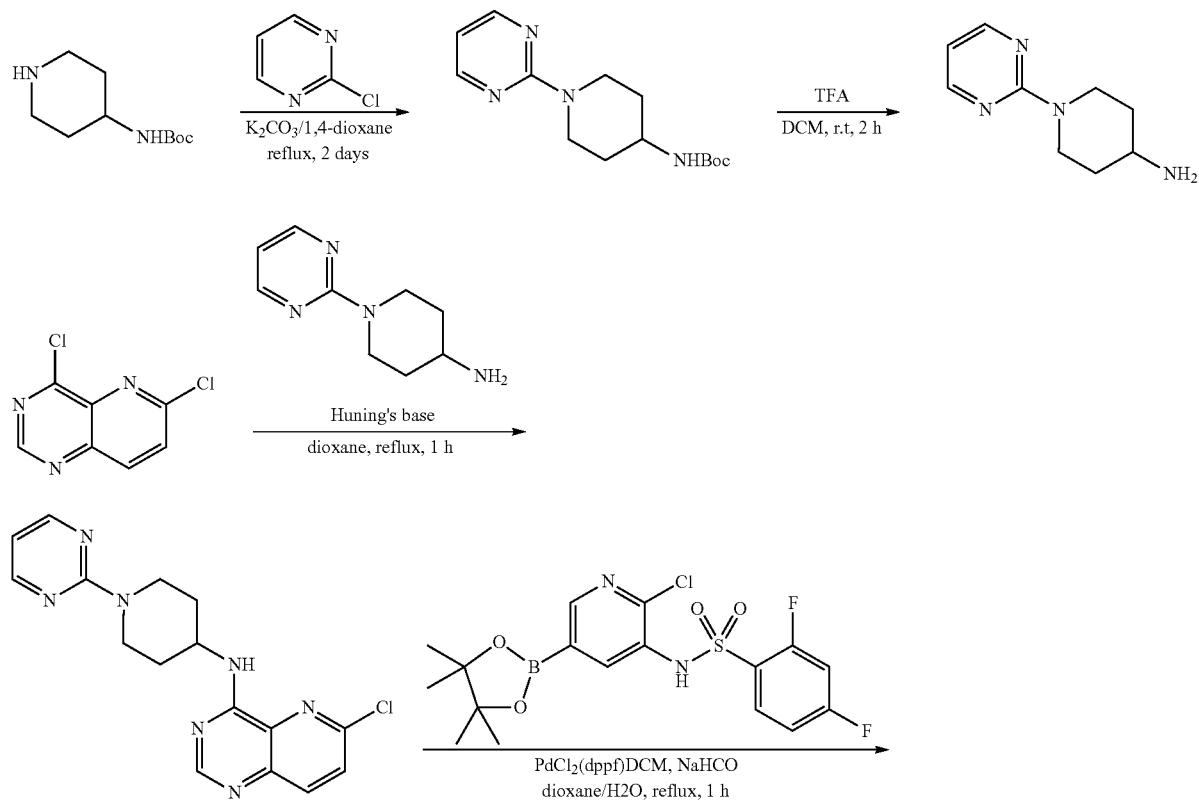

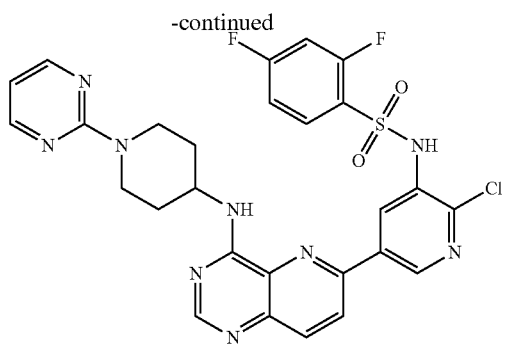

Intermediate 1

4,6-dichloropyrido[3,2-d]pyrimidine

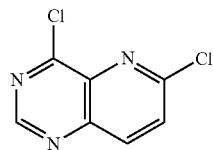 [SMILES: Clc1ccc2ncnc(Cl)c2n1]

Step A: 3-amino-6-chloropicolinamide

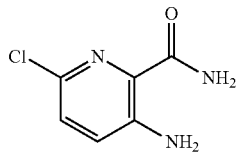 [SMILES: NC(=O)c1nc(Cl)ccc1N]

SnCl$_2$ (27.5 g, 122 mmol) was added to a suspension of 6-chloro-3-nitropicolinonitrile (5.60 g, 30.5 mmol) in EtOH (40 mL) at room temperature. The reaction mixture was heated at 90° C. for 2 h. After cooled to room temperature, the solvent was removed under reduced pressure, EtOAc was poured into the residue. The mixture was neutralized with aq. Na$_2$HCO$_3$ and aq. NaOH until pH ~9, filtered through a Celite pad. The filtrate was extracted with EtOAc, dried over Na$_2$SO$_4$, and concentrated in vacuo to give 3-amino-6-chloropicolinamide (5.00 g, 96%) as a yellow solid which was used for the next step without further purification. $^1$H-NMR (DMSO-d6, Varian 400 MHz) δ 7.01 (2H, brs), 7.22 (1H, d, J=8.8 Hz), 7.30 (1H, d, J=8.8 Hz), 7.42 (1H, brs), 7.71 (1H, brs). m/z=171.98 [M+1]$^+$.

Step B: 6-chloropyrido[3,2-d]pyrimidin-4(3H)-one

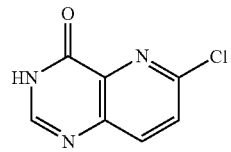

A suspension of 3-amino-6-chloropicolinamide (2.56 g, 14.9 mmol) in triethylorthoformate (45 mL, 271 mmol) was refluxed for 6 h. The reaction mixture was cooled to room temperature, diluted with hexane, and then filtered. The filter cake was washed with hexane and dried under vacuum to give 6-chloropyrido[3,2-d]pyrimidin-4(3H)-one (2.55 g, 94%) as a pale yellow solid. $^1$H-NMR (DMSO-d6, Varian 400 MHz) δ 7.88 (1H, d, J=8.4 Hz), 8.14 (1H, d, J=8.4 Hz), 8.20 (1H, s), 12.65 (1H, brs). m/z=182.06 [M+1]$^+$.

Step C: 4,6-dichloropyrido[3,2-d]pyrimidine

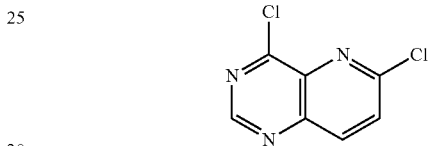

Huning's base (1.18 mL, 6.77 mmol) was added to a solution of 6-chloropyrido[3,2-d]pyrimidin-4(3H)-one (820 mg, 4.52 mmol) in POCl$_3$ (8.42 mL, 90.0 mmol) at room temperature, and the reaction mixture was heated at 110° C. for 5 h. After cooled to room temperature, the excess POCl$_3$ was removed by evaporation. Toluene was added to the residue, and the azeotrope was removed under reduced pressure. DCM was poured into the residue, and the suspension was treated carefully with aq. NaHCO$_3$ at 0° C. to pH 7~9. The insoluble solid was filtered off, and the filtrate was extracted with DCM. The combined organic layers were dried over Na$_2$SO$_4$, filtered, and concentrated in vacuo. The residue was purified by column chromatography (DCM:EtOAc=10:1) to give 4,6-dichloropyrido[3,2-d]pyrimidine (780 mg, 86%) as a pale yellow solid. $^1$H-NMR (CDCl$_3$, Varian 400 MHz) δ 7.86 (1H, d, J=8.8 Hz), 8.34 (1H, d, J=8.8 Hz), 9.14 (1H, s). m/z=199.01 [M+1]$^+$.

Intermediate 2

N-(2-chloro-5-(4,4,5,5-tetramethyl-1,3,2-dioxaborolan-2-yl)pyridine-3-yl)-2,4-difluorobenzenesulfonamide

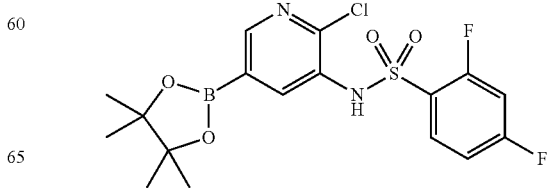

Step A: 5-bromo-2-chloropyridin-3-amine

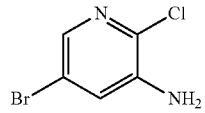

To a solution of 5-bromo-2-chloro-3-nitropyridine (10.0 g, 42.1 mmol) in EtOH (70 ml) and H$_2$O (14 ml) was added iron (11.7 g, 211 mmol) and NH$_4$Cl (6.76 g, 126 mmol) at room temperature. The mixture was refluxed for 1 hour, and then cooled to room temperature, filtered through a Celite pad and washed with EtOH. The filtrate was concentrated in vacuo. The residue was treated with saturated aq. NaHCO$_3$, and extracted with EtOAc. The combined organic layers were washed with brine, dried over anhydrous Na$_2$SO$_4$, filtered, and concentrated in vacuo. The residue was purified by column chromatography (Hexane:EtOAc=3:1) to give 5-bromo-2-chloropyridin-3-amine (7.93 g, 91%) as a white solid. $^1$H-NMR (CDCl$_3$, Varian 400 MHz) δ 5.89 (2H, s), 7.30 (1H, d, J=2.0 Hz), 7.66 (1H, d, J=2.4 Hz).

Step B: N-(5-bromo-2-chloropyridine-3-yl)-N-(2,4-difluorophenylsulfonyl)-2,4-difluorobenzenesulfonamide

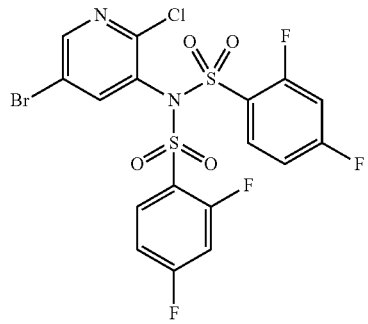 [SMILES: O=S(=O)(c1ccc(F)cc1F)N(c1cc(Br)cnc1Cl)S(=O)(=O)c1ccc(F)cc1F]

To a solution of 5-bromo-2-chloropyridin-3-amine (7.93 g, 38.2 mmol) in pyridine (76 mL) was drop wise added 2,4-difluorobenzene-1-sulfonyl chloride (20.3 g, 96.0 mmol) at 0° C. The mixture was stirred for 1 h at room temperature. The resulting solid was filtered, and washed with water, and dried under vacuum oven to give the N-(5-bromo-2-chloropyridin-3-yl)-N-(2,4-difluorophenylsulfonyl)-2,4-difluorobenzene-sulfonamide (19.6 g, 90%) as a white solid, which was used for the next step without further purification.

Step C: N-(5-bromo-2-chloropyridin-3-yl)-2,4-difluorobenzenesulfonamide

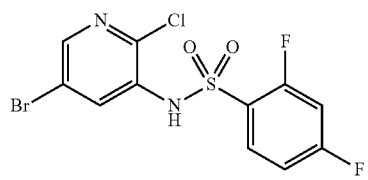 [SMILES: O=S(=O)(Nc1cc(Br)cnc1Cl)c1ccc(F)cc1F]

A solution of N-(5-bromo-2-chloropyridin-3-yl)-N-(2,4-difluorophenylsulfonyl)-2,4-difluorobenzenesulfonamide (19.3 g, 34.4 mmol) in dioxane (340 ml) was heated at 80° C. And then 2 N aq. KOH (86.0 ml, 172 mmol) was added to the mixture. After stirring for 30 min, the reaction mixture was cooled to room temperature, and then quenched with 1 N aq. HCl until pH 3. The resulting solid was collected by filtration and washed with water to give the N-(5-bromo-2-chloropyridin-3-yl)-2,4-difluorobenzenesulfonamide (8.36 g, 63.4%) as a white solid. $^1$H-NMR (CDCl$_3$, Varian 400 MHz) δ 7.25 (1H, t, J=8.4 Hz), 7.58 (1H, t, J=9.2 Hz), 7.77-7.83 (1H, m), 8.03 (1H, d, J=2.0 Hz), 8.44 (1H, d, J=2.0 Hz), 11.04 (1H, brs).

Step D: N-(2-chloro-5-(4,4,5,5-tetramethyl-1,3,2-dioxaborolan-2-yl)pyridine-3-yl)-2,4-difluorobenzenesulfonamide

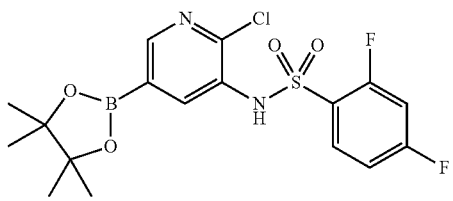 [SMILES: CC1(C)OB(c2cnc(Cl)c(NS(=O)(=O)c3ccc(F)cc3F)c2)OC1(C)C]

A mixture of N-(5-bromo-2-chloropyridin-3-yl)-2,4-difluorobenzenesulfonamide (7.54 g, 19.7 mmol), potassium acetate (7.72 g, 79.0 mmol), bis(pinacolato)diboron (5.99 g, 23.6 mmol) and PdCl$_2$(dppf)-CH$_2$Cl$_2$Adduct (0.80 g, 0.98 mmol) in dioxane (40 mL) was refluxed for 3 h. After cooled to room temperature, the reaction mixture was filtered through a Celite pad and washed with CH$_2$Cl$_2$ The filtrate was diluted with water and extracted with CH$_2$Cl$_2$. The combined organic layers were washed with brine, dried over anhydrous Na$_2$SO$_4$, filtered and concentrated in vacuo. The residue was purified by column chromatography (Hexane:EtOAc=5:1) to give N-(2-chloro-5-(4,4,5,5-tetramethyl-1,3,2-dioxaborolan-2-yl)pyridin-3-yl)-2,4-difluorobenzenesulfonamide (6.50 g, 77%) as a brown oil. $^1$H-NMR (CDCl$_3$, Varian 400 MHz) δ 1.30 (12H, s), 6.88-6.95 (2H, m), 7.79-7.85 (1H, m), 8.20 (1H, d, J=1.6 Hz), 8.40 (1H, d, J=1.6 Hz). NH peak was not observed.

EXAMPLES

Example 1

N-(5-(4-(tetrahydro-2H-pyran-4-yloxy)pyrido[3,2-d]pyrimidin-6-yl)pyridin-3-yl)benzenesulfonamide

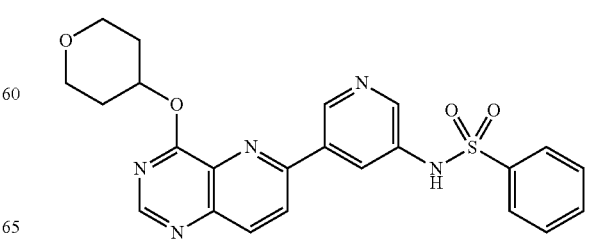

To a solution of 6-chloro-4-(tetrahydro-2H-pyran-4-yloxy)pyrido[3,2-d]pyrimidine (Intermediate 1) (60.0 mg, 0.226 mmol) in 1,4-dioxane (1.20 mL) was added N-(5-(4,4,5,5-tetramethyl-1,3,2-dioxaborolan-2-yl)pyridin-3-yl)benzenesulfonamide (Intermediate 2) (122 mg, 0.339 mmol), PdCl2(dppf)2CH2Cl2 (18.0 mg, 0.0230 mmol), and 1N aq. NaHCO3 (0.452 mL, 0.452 mmol) at room temperature. The reaction mixture was subjected to microwave irradiation for 30 min at 120° C., and cooled to room temperature. The reaction mixture was filtered through a Celite pad and washed with EtOAc. The filtrate was diluted with water and extracted with EtOAc. The combined organic layers were washed with brine, dried over anhydrous Na2SO4, filtered and concentrated in vacuo. The residue was purified by column chromatography on SiO2 (Hex:EtOAc=3:1) to give N-(5-(4-(tetrahydro-2H-pyran-4-yloxy)pyrido[3,2-d]pyrimidin-6-yl)pyridin-3-yl)benzenesulfonamide (20.0 mg, 19%) as a yellow solid. 1H-NMR (CDCl3, Varian 400 MHz) δ 2.02-2.11 (2H, m), 2.23-2.27 (2H, m), 3.68-3.74 (2H, m), 4.10-4.15 (2H, m), 5.64-5.69 (1H, m), 7.07 (1H, brs), 7.47-7.51 (2H, m), 7.56-7.60 (1H, m), 7.85-7.88 (2H, m), 8.21 (1H, d, J=8.8 Hz), 8.36 (1H, d, J=8.8 Hz), 8.38 (1H, s), 8.43 (1H, t, J=2.2 Hz), 8.83 (1H, s), 9.16 (1H, s); m/z=464.2 [M+1]+.

Example 2

N-(2-chloro-5-(4-(tetrahydro-2H-pyran-4-yloxy)pyrido[3,2-d]pyrimidin-6-yl)pyridin-3-yl)-2,4-difluorobenzenesulfonamide

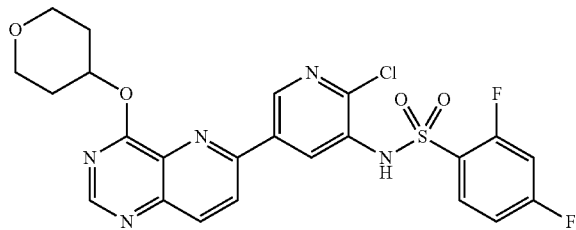 [SMILES: O=S(=O)(Nc1cc(-c2ccc3ncnc(OC4CCOCC4)c3n2)cnc1Cl)c1ccc(F)cc1F]

A mixture of N-(2-chloro-5-(4,4,5,5-tetramethyl-1,3,2-dioxaborolan-2-yl)pyridin-3-yl)-2,4-difluorobenzenesulfonamide (0.02 g, 0.075 mmol) (Intermediate 3), 6-chloro-4-(tetrahydro-2H-pyran-4-yloxy)pyrido[3,2-d]pyrimidine (Intermediate 1) (0.032 g, 0.075 mmol), sodium bicarbonate (0.151 ml, 0.151 mmol) and PdCl2(dppf)-CH2Cl2Adduct (6.15 mg, 7.53 μmol) in dioxane (0.376 ml) was refluxed for 3 hours. The reaction mixture was cooled to room temperature, filtered through a Celite pad and washed with CH2Cl2. The filtrate was concentrated in vacuo. The residue was purified by column chromatography on SiO2 (Hex:EtOAc=2:1) to give N-(2-chloro-5-(4-(tetrahydro-2H-pyran-4-yloxy)pyrido[3,2-d]pyrimidin-6-yl)pyridin-3-yl)-2,4-difluorobenzenesulfonamide (0.02 g, 50%) as a yellow solid.

1H-NMR (CDCl3, Varian 400 MHz) δ 2.06-2.12 (2H, m), 2.23-2.30 (2H, m), 3.66-3.76 (2H, m), 4.02-4.17 (2H, m), 5.66-5.72 (1H, m), 6.73-7.01 (2H, m), 7.53 (1H, brs), 7.92-7.98 (1H, m), 8.20 (1H, d, J=8.8 Hz), 8.37 (1H, d, J=8.8 Hz), 8.80 (1H, d, J=2.4 Hz), 8.84 (1H, s), 8.92 (1H, d, J=2.4 Hz). m/z=534.3 [M+1]+.

Example 3

N-(5-(4-(tetrahydro-2H-pyran-4-yloxy)pyrido[3,2-d]pyrimidin-6-yl)pyridin-3-yl)-2,4-difluorobenzenesulfonamide

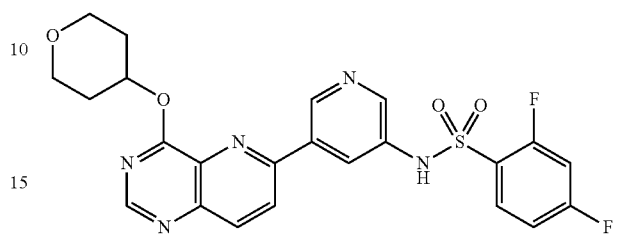

A mixture of N-(5-(4,4,5,5-tetramethyl-1,3,2-dioxaborolan-2-yl)pyridin-3-yl)-2,4-difluoro benzenesulfonamide (0.110 g, 0.278 mmol) (Intermediate 4), 6-chloro-4-(tetrahydro-2H-pyran-4-yloxy)pyrido[3,2-d]pyrimidine (Intermediate 1) (0.081 g, 0.305 mmol), 1 N aq. sodium bicarbonate (0.555 ml, 0.555 mmol) and PdCl2(dppf)-CH2Cl2Adduct (23.0 mg, 2.80 μmol) in dioxane (2.78 ml) was subjected to microwave irradiation for 1 hour at 110° C. The reaction mixture was cooled to room temperature, filtered through a Celite pad and washed with CH2Cl2. The filtrate was concentrated in vacuo. The residue was purified by column chromatography on SiO2 (Hex:EtOAc=2:1) to give N-(5-(4-(tetrahydro-2H-pyran-4-yloxy)pyrido[3,2-d]pyrimidin-6-yl)pyridin-3-yl)-2,4-difluorobenzenesulfonamide (0.15 g, 18%) as a yellow solid. 1H-NMR (DMSO-d6, Varian 400 MHz) δ 1.78-1.98 (2H, m), 2.12-2.26 (2H, m), 3.55-3.72 (2H, m), 3.90-4.05 (2H, m), 5.58-5.72 (1H, m), 7.20-7.42 (1H, m), 7.48-7.62 (2H, m), 7.90-8.05 (1H, m), 8.36-8.52 (2H, m), 8.58 (1H, d, J=8.2 Hz), 8.86 (1H, s), 9.13 (1H, s), 11.29 (1H, br s). m/z=500.1 [M+1]+.

Example 4

N-(2-chloro-5-(4-(tetrahydro-2H-pyran-4-yloxy)pyrido[3,2-d]pyrimidin-6-yl)pyridin-3-yl)benzenesulfonamide

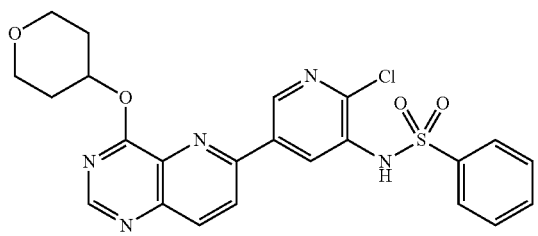 [SMILES: O=S(=O)(Nc1cc(-c2ccc3ncnc(OC4CCOCC4)c3n2)cnc1Cl)c1ccccc1]

A mixture of N-(2-chloro-5-(4,4,5,5-tetramethyl-1,3,2-dioxaborolan-2-yl)pyridin-3-yl)benzene sulfonamide (0.114 g, 0.290 mmol) (Intermediate 5), 6-chloro-4-(tetrahydro-2H-pyran-4-yloxy)pyrido[3,2-d]pyrimidine (Intermediate 1) (0.070 g, 0.263 mmol), 1 N aq. sodium bicarbonate (0.527 ml, 0.527 mmol) and PdCl2(dppf)-CH2Cl2Adduct (22.0 mg, 2.60 μmol) in dioxane (1.5 ml) was subjected to microwave irradiation for 1 hour at 110° C. The reaction mixture was cooled to room temperature, filtered through a Celite pad and washed with CH2Cl2. The filtrate was concentrated in vacuo.

The residue was purified by column chromatography on SiO2 (Hex:EtOAc=2:1) to give N-(2-chloro-5-(4-(tetrahydro-2H-pyran-4-yloxy)pyrido[3,2-d]pyrimidin-6-yl)pyridin-3-yl)benzenesulfonamide (0.030 g, 23%) as a yellow solid. 1H-NMR (DMSO-d6, Varian 400 MHz) δ 1.75-1.98 (2H, m), 2.12-2.26 (2H, m), 3.55-3.72 (2H, m), 3.90-4.05 (2H, m), 5.58-5.72 (1H, m), 7.50-7.70 (3H, m), 7.85 (1H, d, J=7.6 Hz), 8.45 (1H, d, J=8.4 Hz), 8.58-8.72 (2H, m), 8.87 (1H, s), 9.04 (1H, br s), 10.55 (1H, s). m/z=498.09 [M+1]+.

Example 5

N-(2-chloro-5-(4-(1-methylpiperidin-4-yloxy)pyrido[3,2-d]pyrimidin-6-yl)pyridin-3-yl)-2,4-difluorobenzenesulfonamide

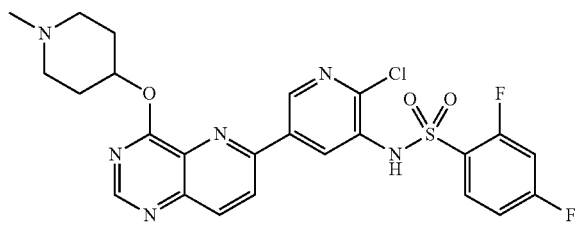 [SMILES: CN1CCC(Oc2ncnc3ccc(-c4cnc(Cl)c(NS(=O)(=O)c5ccc(F)cc5F)c4)nc23)CC1]

A mixture of 6-chloro-4-(1-methylpiperidin-4-yloxy)pyrido[3,2-d]pyrimidine (Intermediate 6) (0.03 g, 0.108 mmol), N-(2-chloro-5-(4,4,5,5-tetramethyl-1,3,2-dioxaborolan-2-yl)pyridin-3-yl)-2,4-difluorobenzenesulfonamide (Intermediate 3) (0.046 g, 0.108 mmol), PdCl2(dppf)-CH2Cl2Adduct (8.79 mg, 10.76 μmol) and sodium bicarbonate (0.215 ml, 0.215 mmol) in dioxane (0.538 ml) was refluxed for 3 hours. After cooling to room temperature, the reaction mixture was filtered through a Celite pad and washed with CH2Cl2. The filtrate was concentrated in vacuo. The residue was purified by prep TLC (EtOAc:MeOH=10:1) to give N-(2-chloro-5-(4-(1-methylpiperidin-4-yloxy)pyrido[3,2-d]pyrimidin-6-yl)pyridin-3-yl)-2,4-difluorobenzene-sulfonamide (0.02 g, 34%) as a yellow solid. 1H-NMR (CDCl3, Varian 400 MHz) δ 2.10-2.22 (2H, m), 2.37 (2H, s), 2.62 (3H, s), 2.88-2.95 (2H, m), 3.13-3.17 (2H, m), 5.64 (1H, brs), 6.86-6.94 (2H, m), 7.86-7.92 (1H, m), 8.21 (1H, d, J=9.2 Hz), 8.34 (1H, d, J=8.8 Hz), 8.79 (1H, d, J=2.0 Hz), 8.82 (1H, s), 8.91 (1H, brs). m/z=547.4 [M+1]+.

Example 6

N-(5-(4-(1-methylpiperidin-4-yloxy)pyrido[3,2-d]pyrimidin-6-yl)pyridin-3-yl)benzene-sulfonamide

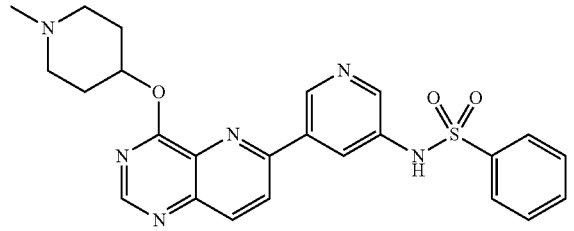 [SMILES: CN1CCC(Oc2ncnc3ccc(-c4cncc(NS(=O)(=O)c5ccccc5)c4)nc23)CC1]

A mixture of 6-chloro-4-(1-methylpiperidin-4-yloxy)pyrido[3,2-d]pyrimidine (Intermediate 6) (0.074 g, 0.265 mmol), N-(5-(4,4,5,5-tetramethyl-1,3,2-dioxaborolan-2-yl)pyridin-3-yl)benzene sulfonamide (Intermediate 2) (0.143 g, 0.398 mmol), PdCl2(dppf)-CH2Cl2Adduct (43.4 mg, 53.0 μmol) and 1N aq. sodium bicarbonate (0.531 ml, 0.531 mmol) in dioxane (1.06 ml) was refluxed for 3 hours. After cooling to room temperature, the reaction mixture was filtered through a Celite pad and washed with CH2Cl2. The filtrate was concentrated in vacuo. The residue was purified by prep TLC (EtOAc only) to give N-(5-(4-(1-methylpiperidin-4-yloxy)pyrido[3,2-d]pyrimidin-6-yl)pyridin-3-yl)-benzenesulfonamide (0.018 g, 14%) as a yellow solid. 1H-NMR (DMSO-d6, Varian 400 MHz) δ 1.88-1.99 (2H, m), 2.12-2.21 (2H, m), 2.26 (3H, s), 2.28-2.36 (2H, m), 2.77-2.85 (2H, m), 5.43 (1H, s), 6.54 (1H, brs), 7.47-7.60 (4H, m), 7.83-7.89 (2H, m), 8.31-8.39 (2H, m), 8.49 (1H, d, J=8.8 Hz), 8.84 (1H, s), 8.91 (1H, s). m/z=477.2 [M+1]+.

Example 7 tert-butyl 4-(6-(5-(phenylsulfonamido)pyridin-3-yl)pyrido[3,2-d]pyrimidin-4-yloxy)-piperidine-1-carboxylate

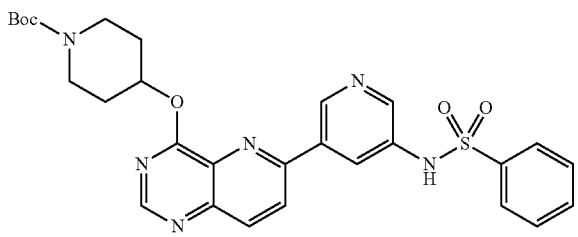 [SMILES: CC(C)(C)OC(=O)N1CCC(Oc2ncnc3ccc(-c4cncc(NS(=O)(=O)c5ccccc5)c4)nc23)CC1]

A mixture of tert-butyl 4-(6-chloropyrido[3,2-d]pyrimidin-4-yloxy)piperidine-1-carboxylate (0.3 g, 0.822 mmol), N-(5-(4,4,5,5-tetramethyl-1,3,2-dioxaborolan-2-yl)pyridin-3-yl)benzene-sulfonamide (Intermediate 2) (0.355 g, 0.987 mmol), PdCl2(dppf)-CH2Cl2Adduct (0.067 g, 0.082 mmol) and 1N aq. sodium bicarbonate (1.64 ml, 1.64 mmol) in dioxane (4.11 ml) was subjected to microwave irradiation for 30 min at 120° C., and cooled to room temperature. The reaction mixture was filtered through a Celite pad and washed with EtOAc. The filtrate was diluted water and extracted with EtOAc. The combined organic layers were washed with brine, dried over anhydrous Na2SO4, filtered and concentrated in vacuo. The residue was purified by column chromatography on SiO2 (Hex:EtOAc=1:1) to give tert-butyl 4-(6-(5-(phenylsulfonamido)-pyridine-3-yl)pyrido[3,2-d]pyrimidin-4-yloxy)piperidine-1-carboxylate (0.15 g, 32%) as a yellow solid. 1H-NMR (CDCl3, Varian 400 MHz) δ 1.49 (9H, s), 1.95-2.05 (2H, m), 2.14-2.18 (2H, m), 3.36-3.43 (2H, m), 3.89-3.95 (2H, m), 5.63-5.37 (1H, m), 7.46-7.52 (2H, m), 7.56-7.60 (1H, m), 7.85 (1H, d, J=7.2 Hz), 8.21 (1H, d, J=8.8 Hz), 8.34 (1H, s), 8.37 (1H, d, J=2.4 Hz), 8.41 (1H, d, J=2.0 Hz), 8.83 (1H, s), 9.14 (1H, d, J=1.6 Hz).

Example 8

N-(5-(4-(piperidin-4-yloxy)pyrido[3,2-d]pyrimidin-6-yl)pyridin-3-yl)benzenesulfonamide

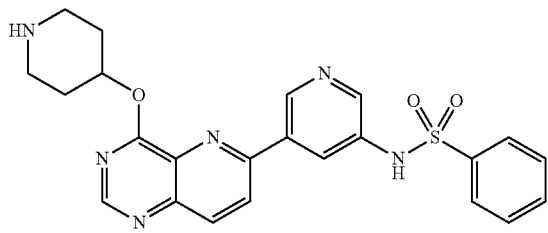 [SMILES: O=S(=O)(Nc1cncc(-c2ccc3ncnc(OC4CCNCC4)c3n2)c1)c1ccccc1]

To a solution of tert-butyl 4-(6-(5-(phenylsulfonamido)-pyridine-3-yl)pyrido[3,2-d]pyrimidin-4-yloxy)piperidine-1-carboxylate (0.15 g, 0.267 mmol) in DCM (1.333 ml) was added TFA (0.205 ml, 2.67 mmol) at room temperature. After stirring for 30 min at room temperature, the reaction mixture was evaporated in vacuo, to give N-(5-(4-(piperidin-4-yloxy)pyrido[3,2-d]pyrimidin-6-yl)pyridin-3-yl)benzenesulfonamide (0.123 g, 100%) as a yellow oil, which was used in the next step without further purification. 1H-NMR (CDCl3, Varian 400 MHz) δ 1.87-1.92 (2H, m), 2.15-2.22 (2H, m), 2.79-2.85 (2H, m), 3.20-3.24 (2H, m), 5.58-5.62 (1H, m), 7.39-7.42 (3H, m), 7.92-7.94 (2H, m), 8.18-8.20 (2H, m), 8.28 (1H, s), 8.59 (1H, d, J=1.6 Hz), 8.74 (1H, s).

Example 9

N-(5-(4-(1-acetylpiperidin-4-yloxy)pyrido[3,2-d]pyrimidin-6-yl)pyridin-3-yl)benzene-sulfonamide

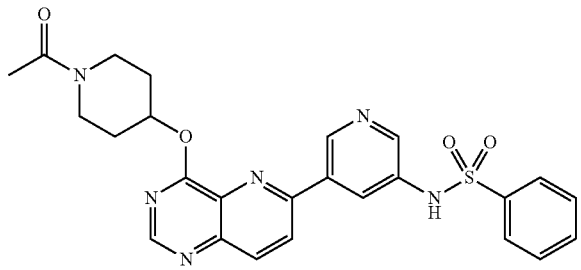 [SMILES: CC(=O)N1CCC(Oc2ncnc3ccc(-c4cncc(NS(=O)(=O)c5ccccc5)c4)nc23)CC1]

To a solution of N-(5-(4-(piperidin-4-yloxy)pyrido[3,2-d]pyrimidin-6-yl)pyridin-3-yl)benzene-sulfonamide (0.082 g, 0.177 mmol) in DCM (0.886 ml) was added TEA (0.062 ml, 0.443 mmol) at room temperature. After stirring for 2 hours at room temperature, AcCl (0.019 ml, 0.266 mmol) was added to the mixture at 0° C. After stirring overnight at room temperature, the reaction mixture was diluted with water and extracted with CH2Cl2. The combined organic layers were washed with brine, dried over anhydrous Na2SO4, filtered and concentrated in vacuo. The residue was purified by prep TLC (DCM:MeOH=20:1) to give N-(5-(4-(1-acetylpiperidin-4-yloxy)-pyrido[3,2-d]pyrimidin-6-yl)pyridin-3-yl)benzenesulfonamide (0.007 g, 7%) as a white solid. 1H-NMR (CDCl3, Varian 400 MHz) δ 2.05-2.18 (2H, m), 2.19 (3H, s), 3.53-3.59 (2H, m), 3.65-3.76 (2H, m), 3.89-3.40 (2H, m), 5.74-8.79 (1H, m), 7.44-7.48 (2H, m), 7.53-7.57 (1H, m), 7.86-7.89 (2H, m), 8.23 (1H, d, J=8.8 Hz), 8.36 (1H, d, J=8.8 Hz), 8.46 (1H, d, J=2.8 Hz), 8.53 (1H, d, J=2.4 Hz), 8.84 (1H, s), 9.12 (1H, d, J=1.6 Hz). m/z=505.1 [M+1]+.

Example 10

N-(5-(4-(pyridin-3-yloxy)pyrido[3,2-d]pyrimidin-6-yl)pyridin-3-yl)benzenesulfonamide

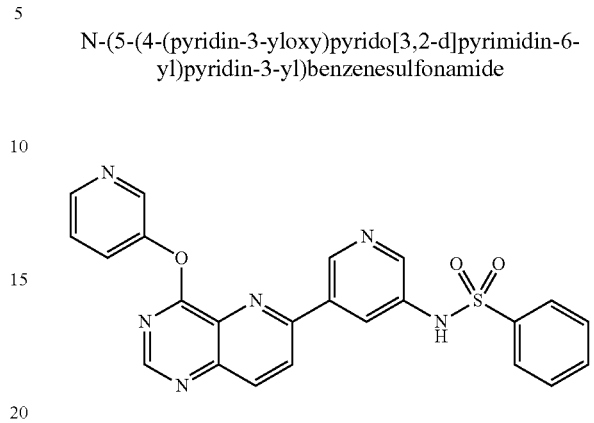

A mixture of 6-chloro-4-(pyridin-3-yloxy)pyrido[3,2-d]pyrimidine (0.090 g, 0.348 mmol) (Intermediate 8), N-(5-(4,4,5,5-tetramethyl-1,3,2-dioxaborolan-2-yl)pyridin-3-yl)benzenesulfonamide (0.150 g, 0.418 mmol) (Intermediate 2), PdCl2(dppf)-CH2Cl2Adduct (0.057 g, 0.070 mmol) and 1N aq. sodium bicarbonate (0.70 ml, 0.70 mmol) in dioxane (1.74 ml) was subjected to microwave irradiation for 30 min at 120° C., and cooled to room temperature. The reaction mixture was filtered through a Celite pad and washed with EtOAc. The filtrate was diluted water and extracted with EtOAc. The combined organic layers were washed with brine, dried over anhydrous Na2SO4, filtered and concentrated in vacuo. The residue was purified by column chromatography on SiO2 (EtOAc only) to give N-(5-(4-(pyridin-3-yloxy)pyrido[3,2-d]pyrimidin-6-yl)pyridin-3-yl)benzenesulfonamide (0.20 g, 13%) as a yellow solid. 1H-NMR (DMSO-d6, Varian 400 MHz) δ 7.45-7.49 (2H, m), 7.51-7.56 (1H, m), 7.61 (1H, dd, J=8.4 and 4.8 Hz), 7.84-7.87 (2H, m), 7.92-7.95 (1H, m), 8.38 (1H, d, J=2.8 Hz), 8.45 (1H, s), 8.49-8.51 (2H, m), 8.53 (1H, dd, J=4.8 and 1.2 Hz), 8.66 (1H, d, J=2.4 Hz), 8.73 (1H, s), 9.06 (1H, d, J=2.0 Hz). m/z=457 [M+1]+.

Example 11

N-(6-(4-(tetrahydro-2H-pyran-4-yloxy)pyrido[3,2-d]pyrimidin-6-yl)pyrazin-2-yl)benzene sulfonamide

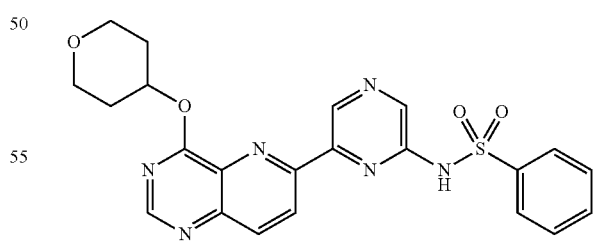

To a solution of 6-(4-(tetrahydro-2H-pyran-4-yloxy)pyrido[3,2-d]pyrimidin-6-yl)-2-(N,N-bis(boc-amino))pyrazine (Intermediate 10) (0.845 g, 1.61 mmol) in DCM (8.05 ml) was slowly added TFA (2.48 ml, 32.2 mmol) at 0° C. After stirring for 4 hours at room temperature, the reaction mixture was quenched with 1N NaOH, and extracted with DCM. The organic layers were dried over MgSO4, filtered and concentrated in vacuo to give 6-(4-(tetrahydro-2H-pyran-4-yloxy) pyrido[3,2-d]pyrimidin-6-yl)pyrazin-2-amine (0.27 g, 52%) as a yellow solid. To a solution of 6-(4-(tetrahydro-2H-pyran-4-yloxy)pyrido[3,2-d]pyrimidin-6-yl)pyrazin-2-amine (0.1 g, 0.308 mmol) in pyridine (1.542 ml) was slowly added benzenesulfonyl chloride (0.050 ml, 0.385 mmol) at 0° C. After stirring for 6 hours at room temperature, the reaction mixture was diluted with DCM and quenched with 1N aq. HCl. The combined organic layers were washed with brine, dried over anhydrous Na2SO4, filtered and concentrated in vacuo. The residue was washed with EtOAc and the resulting solid was collected by filtration to give N-(6-(4-(tetrahydro-2H-pyran-4-yloxy)pyrido[3,2-d]pyrimidin-6-yl)pyrazin-2-yl)benzenesulfonamide (0.02 g, 14%) as a yellow solid. 1H-NMR (DMSO-d6, Varian 400 MHz) δ 1.82-1.90 (2H, m), 2.14-2.17 (2H, m), 3.57-3.62 (2H, m), 3.92-4.06 (2H, m), 5.59-5.63 (1H, m), 7.63-7.65 (3H, m), 8.10 (2H, dd, J=2.0, 7.6 Hz), 8.43 (1H, s), 8.49 (1H, d, J=8.8 Hz), 8.55 (1H, d, J=8.8 Hz), 8.89 (1H, s), 9.21 (1H, s), 11.96 (1H, s). m/z=465.0 [M+1]+.

Example 12

4-bromo-2-chloro-N-(5-(4-(tetrahydro-2H-pyran-4-yloxy)pyrido[3,2-d]pyrimidin-6-yl) pyridin-3-yl) benzenesulfonamide

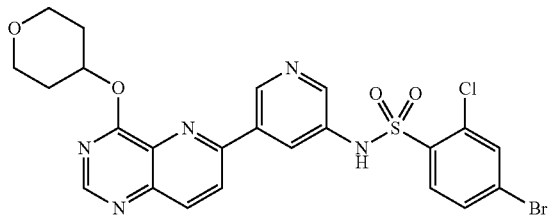 [SMILES: O=S(=O)(Nc1cncc(-c2ccc3ncnc(OC4CCOCC4)c3n2)c1)c1ccc(Br)cc1Cl]

A mixture of 4-bromo-2-chloro-N-(5-(4,4,5,5-tetramethyl-1,3,2-dioxaborolan-2-yl)pyridin-3-yl)benzenesulfonamide (Intermediate 10) (0.0740 g, 0.279 mmol), 6-chloro-4-(tetrahydro-2H-pyran-4-yloxy)pyrido[3,2-d]pyrimidine (Intermediate 1) (0.145 g, 0.306 mmol), 1N aq. sodium bicarbonate (0.557 ml, 0.557 mmol) and PdCl2(dppf)-CH2Cl2 (0.0230 g, 0.0280 mmol) in dioxane (1.40 ml) was subjected to microwave irradiation for 1 hour at 110° C., and cooled to room temperature. The reaction mixture was filtered through a Celite pad and washed with DCM. The combined organic layers were washed brine, dried over anhydrous MgSO4, filtered and concentrated in vacuo. The residue was purified by column chromatography on SiO2 (Hex:EtOAc=1:1) to give 4-bromo-2-chloro-N-(5-(4-(tetrahydro-2H-pyran-4-yloxy)pyrido[3,2-d]pyrimidin-6-yl)pyridin-3-yl)benzene-sulfonamide (0.032 g, 20%) as a yellow solid. 1H-NMR (CDCl3, Varian 400 MHz) δ 2.04-2.12 (2H, m), 2.23-2.27 (2H, m), 3.68-3.74 (2H, m), 4.10-4.15 (2H, m), 5.63-5.69 (1H, m), 7.83 (1H, t, J=2.2 Hz), 7.92 (1H, brs), 8.13-8.16 (1H, m), 8.22 (1H, d, J=8.0 Hz), 8.34-8.42 (4H, m), 8.84 (1H, s). m/z=577.9 [M+1]+.

Example 13

2-bromo-4-fluoro-N-(5-(4-(tetrahydro-2H-pyran-4-yloxy)pyrido[3,2-d]pyrimidin-6-yl) pyridine 3-yl) benzenesulfonamide

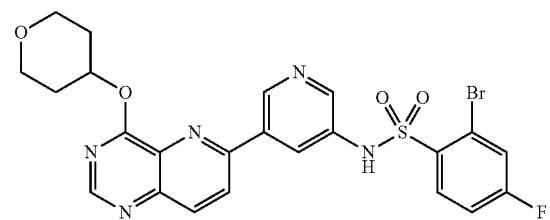

To a solution of 5-(4-(tetrahydro-2H-pyran-4-yloxy)pyrido[3,2-d]pyrimidin-6-yl)pyridin-3-amine (Intermediate 12) (0.0500 g, 0.155 mmol) in pyridine (0.773 ml) was slowly added 2-bromo-4-fluorobenzene-1-sulfonyl chloride (0.0510 g, 0.186 mmol) at 0° C. After stirred for 1 hour at room temperature, the reaction mixture was diluted with DCM and quenched with 1N. aq HCl. The combined organic layers were washed brine, dried over anhydrous MgSO4, filtered and concentrated in vacuo. The residue was recrystallized from EtOAc-Hexane to give 2-bromo-4-fluoro-N-(5-(4-(tetrahydro-2H-pyran-4-yloxy)pyrido[3,2-d]pyrimidin-6-yl)pyridin-3-yl)benzene-sulfonamide (0.0400 g, 46%) as a purple solid. 1H-NMR (CDCl3, Varian 400 MHz) δ 2.02-2.11 (2H, m), 2.24-2.28 (2H, m), 3.69-3.75 (2H, m), 4.11-4.16 (2H, m), 5.65-5.71 (1H, m), 7.08-7.13 (1H, m), 7.46-7.49 (1H, m), 8.14-8.18 (1H, m), 8.22 (1H, d, J=8.8 Hz), 8.38 (1H, d, J=8.8 Hz), 8.55 (1H, s), 8.62 (1H, s), 8.84 (1H, s), 9.16 (1H, s). m/z=562.0 [M+1]+.

Example 14

4-bromo-2-fluoro-N-(5-(4-(tetrahydro-2H-pyran-4-yloxy)pyrido[3,2-d]pyrimidin-6-yl) pyridin-3-yl) benzenesulfonamide

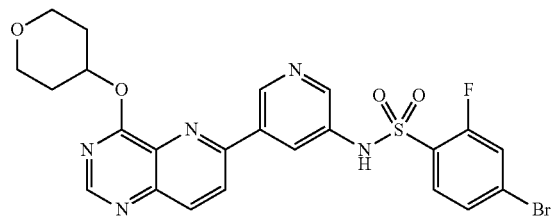 [SMILES: O=S(=O)(Nc1cncc(-c2ccc3ncnc(OC4CCOCC4)c3n2)c1)c1ccc(Br)cc1F]

To a solution of 5-(4-(tetrahydro-2H-pyran-4-yloxy)pyrido[3,2-d]pyrimidin-6-yl)pyridin-3-amine (Intermediate 12) (0.050 g, 0.155 mmol) in pyridine (0.773 ml) was slowly added 4-bromo-2-fluorobenzene-1-sulfonyl chloride (0.051 g, 0.186 mmol) at 0° C. After stirred for 1 hour at room temperature, the reaction mixture was diluted with DCM and quenched with 1 N. aq HCl. The combined organic layers were washed brine, dried over anhydrous MgSO4, filtered and concentrated in vacuo. The residue was recrystallized from EtOAc-Hexane to give 4-bromo-2-fluoro-N-(5-(4-(tetrahydro-2H-pyran-4-yloxy)pyrido[3,2-d]pyrimidin-6-yl)pyridin-3-yl)benzene-sulfonamide (0.028 g, 32%) as a purple solid. 1H-NMR (CDCl3, Varian 400 MHz) δ 2.03-2.11 (2H, m), 2.23-2.28 (2H, m), 3.70-3.75 (2H, m), 4.10-4.16 (2H, m), 5.66-5.71 (1H, m), 7.38-7.41 (2H, m), 7.79-7.83 (1H, m), 8.25 (1H, d, J=8.8 Hz), 8.40 (1H, d, J=8.8 Hz), 8.72 (1H, s), 8.85 (1H, s), 9.20 (1H, m). m/z=562.1 [M+1]+.

Example 15

4-chloro-2-fluoro-N-(5-(4-(tetrahydro-2H-pyran-4-yloxy)pyrido[3,2-d]pyrimidin-6-yl) pyridin-3-yl) benzenesulfonamide

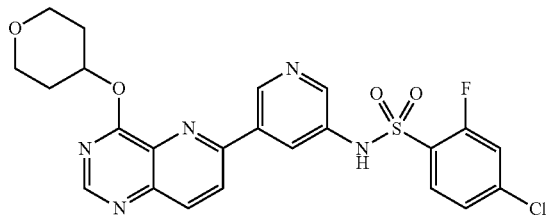 [SMILES: O=S(=O)(Nc1cncc(-c2ccc3ncnc(OC4CCOCC4)c3n2)c1)c1ccc(Cl)cc1F]

To a solution of 5-(4-(tetrahydro-2H-pyran-4-yloxy)pyrido[3,2-d]pyrimidin-6-yl)pyridin-3-amine (Intermediate 12) (0.050 g, 0.155 mmol) in pyridine (0.773 ml) was slowly added 4-chloro-2-fluorobenzene-1-sulfonyl chloride (0.043 g, 0.186 mmol) at 0° C. After stirred for 1 hour at room temperature, the reaction mixture was diluted with DCM and quenched with 1N. aq HCl. The combined organic layers were washed brine, dried over anhydrous MgSO4, filtered and concentrated in vacuo. The residue was recrystallized from EtOAc-Hexane to give 4-chloro-2-fluoro-N-(5-(4-(tetrahydro-2H-pyran-4-yloxy)pyrido[3,2-d]pyrimidin-6-yl)pyridin-3-yl)benzene-sulfonamide (0.034 g, 43%) as a purple solid. 1H-NMR (CDCl3, Varian 400 MHz) δ 2.03-2.11 (2H, m), 2.23-2.28 (2H, m), 3.70-3.75 (2H, m), 4.11-4.16 (2H, m), 5.65-5.71 (1H, m), 7.24 (1H, d, J=8.4 Hz), 7.86-7.90 (1H, m), 8.24 (1H, d, J=8.8 Hz), 8.39 (1H, d, J=8.8 Hz), 8.66 (1H, d, J=7.6 Hz), 8.85 (1H, s), 9.19 (1H, s). m/z=516.1 [M+1]+.

Example 16

2-chloro-4-fluoro-N-(5-(4-(tetrahydro-2H-pyran-4-yloxy)pyrido[3,2-d]pyrimidin-6-yl) pyridin-3-yl) benzenesulfonamide

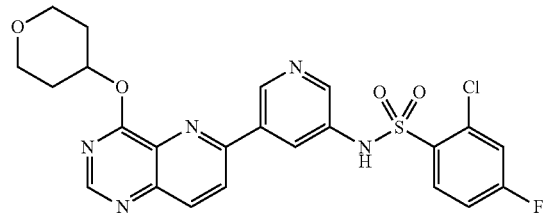 [SMILES: O=S(=O)(Nc1cncc(-c2ccc3ncnc(OC4CCOCC4)c3n2)c1)c1ccc(F)cc1Cl]

To a solution of 5-(4-(tetrahydro-2H-pyran-4-yloxy)pyrido[3,2-d]pyrimidin-6-yl)pyridin-3-amine (Intermediate 12) (0.0500 g, 0.155 mmol) in pyridine (0.773 ml) was slowly added 2-chloro-4-fluorobenzene-1-sulfonyl chloride (0.0430 g, 0.186 mmol) at 0° C. After stirred for 1 hour at room temperature, the reaction mixture was diluted with DCM and quenched with 1N. aq HCl. The combined organic layers were washed brine, dried over anhydrous MgSO4, filtered and concentrated in vacuo. The residue was recrystallized from EtOAc-Hexane to give 2-chloro-4-fluoro-N-(5-(4-(tetrahydro-2H-pyran-4-yloxy)pyrido[3,2-d]pyrimidin-6-yl)pyridin-3-yl)benzene-sulfonamide (0.0500 g, 63%) as a purple solid. 1H-NMR (CDCl3, Varian 400 MHz) δ 2.02-2.11 (2H, m), 2.23-2.28 (2H, m), 3.70-3.75 (2H, m), 4.11-4.16 (2H, m), 5.65-5.70 (1H, m), 7.04-7.09 (1H, m), 7.26-7.28 (2H, m), 8.11-8.15 (1H, m), 8.22 (1H, d, J=8.8 Hz), 8.37 (1H, d, J=8.8 Hz), 8.54 (1H, s), 8.60 (1H, s), 9.16 (1H, s). m/z=516.1 [M+1]+.

Example 17

2,4-dibromo-N-(5-(4-(tetrahydro-2H-pyran-4-yloxy) pyrido[3,2-d]pyrimidin-6-yl)pyridin-3-yl)benzene-sulfonamide

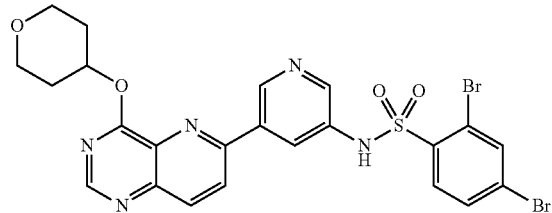 [SMILES: O=S(=O)(Nc1cncc(-c2ccc3ncnc(OC4CCOCC4)c3n2)c1)c1ccc(Br)cc1Br]

To a solution of 5-(4-(tetrahydro-2H-pyran-4-yloxy)pyrido[3,2-d]pyrimidin-6-yl)pyridin-3-amine (Intermediate 12) (0.0500 g, 0.155 mmol) in pyridine (0.773 ml) was slowly added 2,4-dibromobenzene-1-sulfonyl chloride (0.0620 g, 0.186 mmol) at 0° C. After stirred for 1 hour at room temperature, the reaction mixture was diluted with DCM and quenched with 1N. aq HCl. The combined organic layers were washed brine, dried over anhydrous MgSO4, filtered and concentrated in vacuo. The residue was recrystallized from EtOAc-Hexane to give 2,4-dibromo-N-(5-(4-(tetrahydro-2H-pyran-4-yloxy)pyrido[3,2-d]pyrimidin-6-yl)pyridin-3-yl)benzenesulfonamide (0.0550 g, 57%) as a purple solid. 1H-NMR (CDCl3, Varian 400 MHz) δ 2.03-2.11 (2H, m), 2.24-2.28 (2H, m), 3.70-3.75 (2H, m), 4.11-4.16 (2H, m), 5.65-5.71 (1H, m), 7.53 (1H, dd, J=2.0, 8.4 Hz), 7.90 (1H, d, J=1.6 Hz), 7.97 (1H, d, J=8.4 Hz), 8.21 (1H, d, J=8.8 Hz), 8.37 (1H, d, J=8.8 Hz), 8.52 (1H, s), 8.59 (1H, d, J=2.8 Hz), 8.84 (1H, s), 9.16 (1H, d, J=2.0 Hz). m/z=622.0 [M+1]+.

Example 18

2,4-dichloro-N-(5-(4-(tetrahydro-2H-pyran-4-yloxy) pyrido[3,2-d]pyrimidin-6-yl)pyridin-3-yl)benzene-sulfonamide

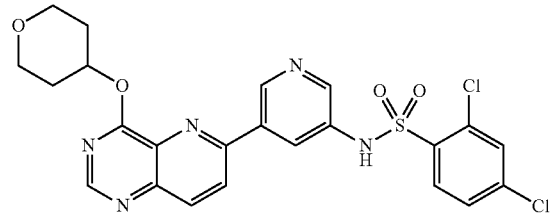 [SMILES: O=S(=O)(Nc1cncc(-c2ccc3ncnc(OC4CCOCC4)c3n2)c1)c1ccc(Cl)cc1Cl]

To a solution of 5-(4-(tetrahydro-2H-pyran-4-yloxy)pyrido[3,2-d]pyrimidin-6-yl)pyridin-3-amine (Intermediate 12) (0.0500 g, 0.155 mmol) in pyridine (0.773 ml) was slowly added 2,4-dichlorobenzene-1-sulfonyl chloride (0.0460 g, 0.186 mmol) at 0° C. After stirred for 1 hour at room temperature, the reaction mixture was diluted with DCM and quenched with 1N. aq HCl. The combined organic layers were washed brine, dried over anhydrous MgSO4, filtered and concentrated in vacuo. The residue was recrystallized from EtOAc-Hexane to give 2,4-dichloro-N-(5-(4-(tetrahydro-2H-pyran-4-yloxy)pyrido[3,2-d]pyrimidin-6-yl)pyridin-3-yl)benzenesulfonamide (0.0340, 41%) as a purple solid. 1H-NMR (CDCl3, Varian 400 MHz) δ 2.02-2.11 (2H, m), 2.24-2.29 (2H, m), 3.70-3.75 (2H, m), 4.10-4.16 (2H, m), 5.65-5.71 (1H, m), 7.33 (1H, dd, J=1.8, 8.6 Hz), 7.54 (1H, d, J=2.0 Hz), 8.05 (1H, d, J=8.8 Hz), 8.20 (1H, d, J=9.2 Hz), 8.36 (1H, d, J=8.8 Hz), 8.48-8.55 (2H, m), 8.84 (1H, s), 9.15 (1H, d, J=1.6 Hz). m/z=532.0 [M+1]+.

Example 19

N-(5-(4-(tetrahydro-2H-pyran-4-yloxy)pyrido[3,2-d]pyrimidin-6-yl)pyridin-3-yl)benzamide

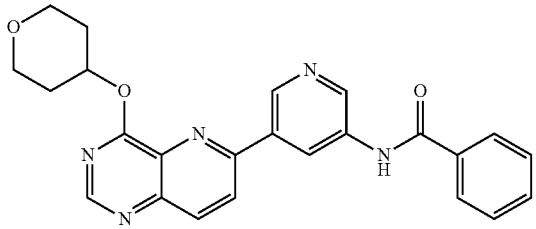 [SMILES: O=C(Nc1cncc(-c2ccc3ncnc(OC4CCOCC4)c3n2)c1)c1ccccc1]

A mixture of N-(5-(4,4,5,5-tetramethyl-1,3,2-dioxaborolan-2-l)pyridin-3-yl)benzamide (Intermediate 13) (0.07 g, 0.216 mmol), 6-chloro-4-(tetrahydro-2H-pyran-4-yloxy)pyrido[3,2-d]pyrimidine (Intermediate 1) (0.063 g, 0.238 mmol), 1N aq. sodium bicarbonate (0.432 ml, 0.432 mmol) and PdCl2(dppf)-CH2Cl2 (0.018 g, 0.022 mmol) in dioxane (1.08 ml) was subjected to microwave irradiation for 1 hour at 110° C., and cooled to room temperature. The reaction mixture was filtered through a Celite pad and washed with DCM. The filtrate was concentrated in vacuo. The residue was purified by column chromatography on SiO2 (only EtOAc) to give N-(5-(4-(tetrahydro-2H-pyran-4-yloxy)pyrido[3,2-d]pyrimidin-6-yl)pyridin-3-yl)benzamide (0.058 g, 63%) as a pink solid. 1H-NMR (CDCl3, Varian 400 MHz) δ 2.04-2.11 (2H, m), 2.23-2.27 (2H, m), 3.67-3.73 (2H, m), 4.10-4.15 (2H, m), 5.63-5.70 (1H, m), 7.53-7.56 (2H, m), 7.60-7.63 (1H, m), 7.94 (2H, d, J=7.2 Hz), 8.12 (1H, brs), 8.29 (1H, d, J=8.8 Hz), 8.36 (1H, d, J=8.8 Hz), 8.83 (1H, s), 8.91 (1H, d, J=2.8 Hz), 9.01 (1H, t, J=2.2 Hz), 9.20 (1H, d, J=2.0 Hz). m/z=428.2 [M+1]+.

Example 20

N-(2-chloro-5-(4-(tetrahydro-2H-pyran-4-yloxy)pyrido[3,2-d]pyrimidin-6-yl)pyridin-3-yl)-2,4-difluorobenzamide

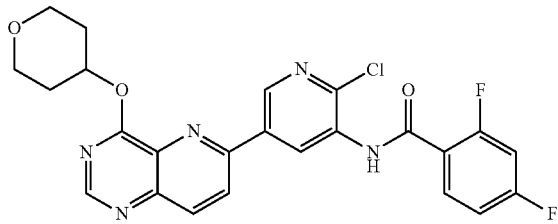 [SMILES: O=C(Nc1cc(-c2ccc3ncnc(OC4CCOCC4)c3n2)cnc1Cl)c1ccc(F)cc1F]

A mixture of N-(2-chloro-5-(4,4,5,5-tetramethyl-1,3,2-dioxaborolan-2-yl)pyridin-3-yl)-2,4-difluorobenzamide (Intermediate 14) (0.100 g, 0.253 mmol), 6-chloro-4-(tetrahydro-2H-pyran-4-yloxy)pyrido[3,2-d]pyrimidine (Intermediate 1) (0.074 g, 0.279 mmol), 1N aq. sodium bicarbonate (0.043 g, 0.507 mmol) and PdCl2(dppf)-CH2Cl2 (0.021 g, 0.025 mmol) in dioxane (1.26 ml) was subjected to microwave irradiation for 1 hour at 110° C., and cooled to room temperature. The reaction mixture was filtered through a Celite pad and washed with DCM. The combined organic layers were washed brine, dried over anhydrous MgSO4, filtered and concentrated in vacuo. The residue was purified by column chromatography on SiO2 (Hex:EtOAc=1:1) to give N-(2-chloro-5-(4-(tetrahydro-2H-pyran-4-yloxy)pyrido[3,2-d]pyrimidin-6-yl)pyridin-3-yl)-2,4-difluorobenzamide (0.020 g, 16%) as a yellow solid. 1H-NMR (CDCl3, Varian 400 MHz) δ 2.05-2.13 (2H, m), 2.23-2.27 (2H, m), 3.70-3.76 (2H, m), 4.11-4.18 (2H, m), 5.65-5.71 (1H, m), 7.00-7.05 (1H, m), 7.10-7.15 (1H, m), 8.25-8.38 (3H, m), 8.84 (1H, s), 8.03 (1H, d, J=2.4 Hz), 9.19-9.24 (1H, m), 9.71 (1H, d, J=2.4 Hz). m/z=498.0 [M+1]+.

Example 21

N-(5-(4-(cyclohexylthio)pyrido[3,2-d]pyrimidin-6-yl)pyridin-3-yl)benzenesulfonamide

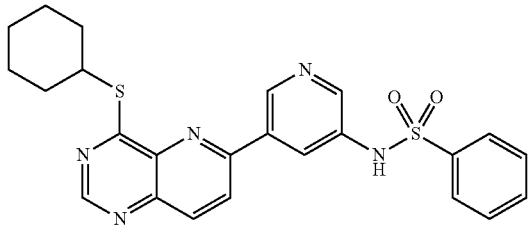 [SMILES: O=S(=O)(Nc1cncc(-c2ccc3ncnc(SC4CCCCC4)c3n2)c1)c1ccccc1]

A mixture of 6-chloro-4-(cyclohexylthio)pyrido[3,2-d]pyrimidine (Intermediate 15) (0.12 g, 0.429 mmol), N-(5-(4,4,5,5-tetramethyl-1,3,2-dioxaborolan-2-yl)pyridin-3-yl)benzenesulfonamide (Intermediate 2) (0.12 g, 0.429 mmol), 1 N aq. sodium bicarbonate (0.858 ml, 0.858 mmol) and PdCl2(dppf)-CH2Cl2 (0.035 g, 0.043 mmol) in dioxane (2.14 ml) was subjected to microwave irradiation for 1 hour at 110° C., and cooled to room temperature. The reaction mixture was filtered through a Celite pad and washed with DCM. The residue was purified by column chromatography on SiO2 (Hex:EtOAc=1:1) to give N-(5-(4-(cyclohexylthio)pyrido[3,2-d]pyrimidin-6-yl)pyridin-3-yl)benzenesulfon-amide (0.09 g, 89%) as a brown solid. 1H-NMR (CDCl3, Varian 400 MHz) δ 1.26-1.28 (1H, m), 1.34-1.43 (1H, m), 1.52-1.85 (4H, m), 1.85-1.87 (2H, m), 2.19-2.23 (2H, m), 4.12-4.19 (1H, m), 7.48-7.58 (3H, m), 7.92 (2H, d, J=8.8 Hz), 8.21 (1H, d, J=8.8 Hz), 8.32 (1H, d, J=9.2 Hz), 8.41-8.43 (2H, m), 8.99 (1H, s), 9.13 (1H, s). m/z=478.1 [M+1]+.

Example 22

N-(2-chloro-5-(4-(cyclopentyloxy)pyrido[3,2-d]pyrimidin-6-yl)pyridin-3-yl)-2,4-difluoro benzenesulfonamide

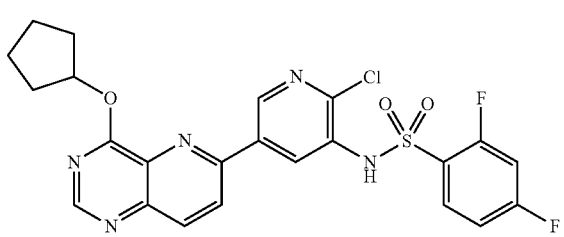 [SMILES: O=S(=O)(Nc1cc(-c2ccc3ncnc(OC4CCCC4)c3n2)cnc1Cl)c1ccc(F)cc1F]

A mixture of 6-chloro-4-(cyclopentyloxy)pyrido[3,2-d]pyrimidine (Intermediate 16) (0.04 g, 0.160 mmol), N-(2-chloro-5-(4,4,5,5-tetramethyl-1,3,2-dioxaborolan-2-yl)pyridin-3-yl)-2,4-difluorobenzenesulfonamide (Intermediate 2) (0.083 g, 0.192 mmol), 1 N aq. sodium bicarbonate (0.320 ml, 0.320 mmol) and PdCl2(dppf)-CH2Cl2 (1.31 mg, 1.60 μmol) in dioxane (0.8 ml) was subjected to microwave irradiation for 1 hour at 110° C., and cooled to room temperature. The reaction mixture was filtered through a Celite pad and washed with DCM. The residue was purified by column chromatography on SiO2 (Hex:EtOAc=1:1) to give N-(2-chloro-5-(4-(cyclopentyloxy)pyrido[3,2-d]pyrimidin-6-yl)pyridin-3-yl)-2,4-difluorobenzene sulfonamide (0.04 g, 48%) as a white solid. 1H-NMR (CDCl3, Varian 400 MHz): δ 1.70-1.80 (2H, m), 1.92-2.01 (2H, m), 2.04-2.11 (2H, m), 2.13-2.22 (2H, m), 5.79-5.83 (1H, m), 6.92-7.00 (2H, m), 7.46 (1H, s), 7.93-7.99 (1H, m), 8.17 (1H, d, J=8.8 Hz), 8.35 (1H, d, J=8.8 Hz), 8.79 (1H, s), 8.86 (1H, s), 8.90 (1H, s). m/z=517.9 [M+1]+.

Example 23

N-(2-chloro-5-(4-(tetrahydro-2H-pyran-4-ylamino)pyrido[3,2-d]pyrimidin-6-yl)-pyridin-3-yl)-2,4-difluorobenzenesulfonamide

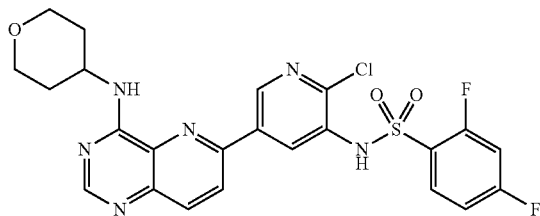 [SMILES: O=S(=O)(Nc1cc(-c2ccc3ncnc(NC4CCOCC4)c3n2)cnc1Cl)c1ccc(F)cc1F]

A mixture of 6-chloro-N-(tetrahydro-2H-pyran-4-yl)pyrido[3,2-d]pyrimidin-4-amine (0.026 g, 0.098 mmol) (Intermediate 17), N-(2-chloro-5-(4,4,5,5-tetramethyl-1,3,2-dioxaborolan-2-yl) pyridine-3-yl)-2,4-difluorobenzenesulfonamide (Intermediate 3) (0.051 g, 0.118 mmol), PdCl2(dppf)-CH2Cl2Adduct (0.802 mg, 0.982 µmol) and sodium bicarbonate (0.196 ml, 0.196 mmol) in dioxane (0.491 ml) was refluxed for 3 hours. After cooling to room temperature, the reaction mixture was filtered through Celite and washed with CH2Cl2. The filtrate was concentrated in vacuo. The residue was purified by column chromatography on SiO2 (only EtOAc) to give N-(2-chloro-5-(4-(tetrahydro-2H-pyran-4-ylamino)pyrido[3,2-d]pyrimidin-6-yl)pyridin-3-yl)-2,4-difluorobenzenesulfonamide (0.015 g, 29%) as a white solid. 1H-NMR (CDCl3, Varian 400 MHz) δ 1.68-1.83 (2H, m), 2.13-2.20 (2H, m), 3.58-3.65 (2H, m), 4.05-4.12 (2H, m), 4.41-4.50 (1H, m), 6.94-7.02 (2H, m), 7.18 (1H, d, J=8.0 Hz), 7.84-7.90 (1H, m), 8.09 (1H, d, J=8.8 Hz), 8.24 (1H, d, J=8.4 Hz), 8.65 (1H, s), 8.74 (1H, d, J=2.0 Hz), 8.84 (1H, d, J=2.4 Hz). NH peak was not observed. m/z=533.4 [M+1]+.

Example 24

N-(2-chloro-5-(4-(cyclopentylamino)pyrido[3,2-d]pyrimidin-6-yl)pyridin-3-yl)-2,4-difluoro benzenesulfonamide

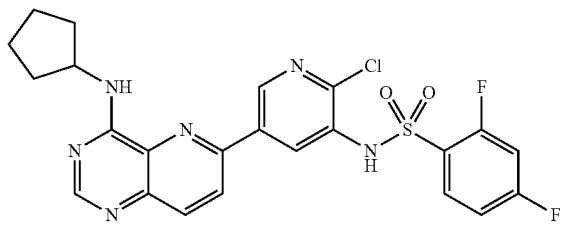 [SMILES: O=S(=O)(Nc1cc(-c2ccc3ncnc(NC4CCCC4)c3n2)cnc1Cl)c1ccc(F)cc1F]

A mixture of 6-chloro-N-(tetrahydro-2H-pyran-4-yl)pyrido[3,2-d]pyrimidin-4-amine (Intermediate 18) (0.043 g, 0.173 mmol), N-(2-chloro-5-(4,4,5,5-tetramethyl-1,3,2-dioxaborolan-2-yl)pyridine-3-yl)-2,4-difluorobenzenesulfonamide (Intermediate 3) (0.089 g, 0.207 mmol), PdCl2 (dppf)-CH2Cl2Adduct (1.41 mg, 1.73 µmol) and 1 N aq. sodium bicarbonate (0.346 ml, 0.346 mmol) in dioxane (0.864 ml) subjected to microwave irradiation for 1 hour at 110° C. After cooling to room temperature, the reaction mixture was filtered through Celite and washed with CH2Cl2. The filtrate was concentrated in vacuo. The residue was purified by column chromatography on SiO2 (Hex:EtOAc=1:1) to give N-(2-chloro-5-(4-(cyclo pentyl amino)pyrido[3,2-d]pyrimidin-6-yl)pyridin-3-yl)-2,4-difluorobenzenesulfonamide (0.046 g, 52%) as a white solid. 1H-NMR (CDCl3, Varian 400 MHz) δ 1.65-1.89 (6H, m), 2.18-2.25 (2H, m), 4.61-4.66 (1H, m), 6.93-7.01 (2H, m), 7.22 (1H, d, J=7.6 Hz), 7.85-7.90 (1H, m), 8.07 (1H, d, J=8.8 Hz), 8.21 (1H, d, J=8.8 Hz), 8.66 (1H, s), 8.74 (1H, d, J=2.0 Hz), 8.82 (1H, d, J=2.0 Hz). m/z=517.2 [M+1]+.

Example 25

N-(2-chloro-5-(4-(cyclobutylamino)pyrido[3,2-d]pyrimidin-6-yl)pyridin-3-yl)-2,4-difluoro benzenesulfonamide

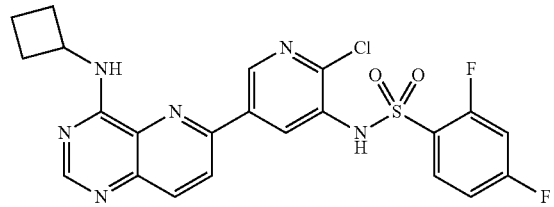 [SMILES: O=S(=O)(Nc1cc(-c2ccc3ncnc(NC4CCC4)c3n2)cnc1Cl)c1ccc(F)cc1F]

A mixture of 6-chloro-N-cyclobutylpyrido[3,2-d]pyrimidin-4-amine (Intermediate 19) (0.050 g, 0.213 mmol), N-(2-chloro-5-(4,4,5,5-tetramethyl-1,3,2-dioxaborolan-2-yl)pyridine-3-yl)-2,4-difluorobenzenesulfonamide (Intermediate 3) (0.110 g, 0.256 mmol), PdCl2(dppf)-CH2Cl2 Adduct (1.74 mg, 2.13 µmol) and 1 N aq. sodium bicarbonate (0.426 ml, 0.426 mmol) in dioxane (1.00 ml) subjected to microwave irradiation for 1 hour at 110° C. After cooling to room temperature, the reaction mixture was filtered through Celite and washed with CH2Cl2. The filtrate was concentrated in vacuo. The residue was purified by column chromatography on SiO2 (Hex:EtOAc=1:1) to give N-(2-chloro-5-(4-(cyclobutylamino)pyrido[3,2-d]pyrimidin-6-yl) pyridin-3-yl)-2,4-difluorobenzenesulfonamide (0.087 g, 81%) as a yellow solid. 1H-NMR (CDCl3, Varian 400 MHz) δ 1.84-1.95 (2H, m), 2.10-2.20 (2H, m), 2.54-2.62 (2H, m), 4.77-4.87 (1H, m), 6.94-7.02 (2H, m), 7.34 (1H, d, J=8.0 Hz), 7.86-7.92 (1H, m), 8.07 (1H, d, J=8.8 Hz), 8.21 (1H, d, J=8.8 Hz), 8.65 (1H, s), 8.73 (1H, d, J=2.4 Hz), 8.84 (1H, d, J=2.4 Hz). m/z=503.2 [M+1]+.

Example 26

N-(2-chloro-5-(4-(cyclopropylamino)pyrido[3,2-d]pyrimidin-6-yl)pyridin-3-yl)-2,4-difluoro benzenesulfonamide

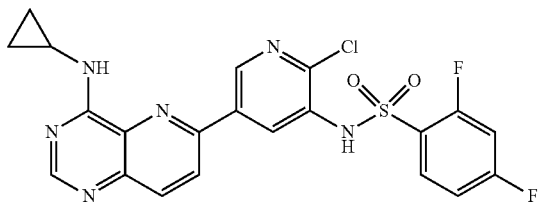 [SMILES: O=S(=O)(Nc1cc(-c2ccc3ncnc(NC4CC4)c3n2)cnc1Cl)c1ccc(F)cc1F]

A mixture of 6-chloro-N-cyclopropylpyrido[3,2-d]pyrimidin-4-amine (Intermediate 20) (0.060 g, 0.272 mmol), N-(2-chloro-5-(4,4,5,5-tetramethyl-1,3,2-dioxaborolan-2-yl)pyridine-3-yl)-2,4-difluorobenzenesulfonamide (Intermediate 3) (0.141 g, 0.326 mmol), PdCl2(dppf)-CH2Cl2 Adduct (2.221 mg, 2.72 μmol) and 1 N aq. sodium bicarbonate (0.544 ml, 0.544 mmol) in dioxane (1.40 ml) subjected to microwave irradiation for 1 hour at 110° C. After cooling to room temperature, the reaction mixture was filtered through Celite and washed with CH2Cl2. The filtrate was concentrated in vacuo. The residue was purified by column chromatography on SiO2 (Hex:EtOAc=1:1) to give N-(2-chloro-5-(4-(cyclopropylamino)pyrido[3,2-d]pyrimidin-6-yl) pyridin-3-yl)-2,4-difluorobenzenesulfonamide (0.070 g, 53%) as a yellow solid. 1H-NMR (CDCl3, Varian 400 MHz) δ 0.78-0.82 (2H, m), 1.04-1.09 (2H, m), 3.08-3.13 (1H, m), 6.95-7.02 (2H, m), 7.30 (1H, brs), 7.85-7.91 (1H, m), 8.08 (1H, d, J=8.8 Hz), 8.24 (1H, d, J=8.8 Hz), 8.67 (1H, d, J=2.0 Hz), 8.76 (1H, s), 8.81 (1H, d, J=2.0 Hz). m/z=489.2 [M+1]+.

Example 27

N-(2-chloro-5-(4-(3,5-dimethylisoxazol-4-ylamino)pyrido[3,2-d]pyrimidin-6-yl)pyridin-3-yl)-2,4-difluorobenzenesulfonamide

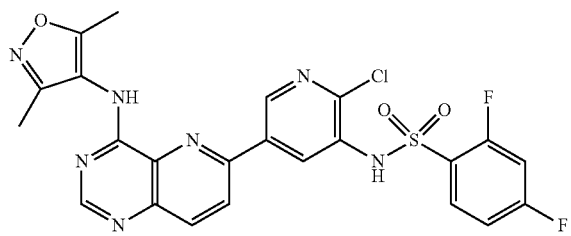 [SMILES: Cc1noc(C)c1Nc1ncnc2ccc(-c3cnc(Cl)c(NS(=O)(=O)c4ccc(F)cc4F)c3)nc12]

A mixture of N-(6-chloropyrido[3,2-d]pyrimidin-4-yl)-3,5-dimethylisoxazol-4-amine (Intermediate 21) (0.040 g, 0.145 mmol), N-(2-chloro-5-(4,4,5,5-tetramethyl-1,3,2-dioxaborolan-2-yl)pyridine-3-yl)-2,4-difluorobenzenesulfonamide (Intermediate 3) (0.069 g, 0.160 mmol), PdCl2(dppf)-CH2Cl2Adduct (0.012 g, 0.015 μmol) and 1 N aq. sodium bicarbonate (0.290 ml, 0.290 mmol) in dioxane (1.40 ml) subjected to microwave irradiation for 1 hour at 110° C. After cooling to room temperature, the reaction mixture was filtered through Celite and washed with CH2Cl2. The filtrate was concentrated in vacuo. The residue was purified by column chromatography on SiO2 (Hex:EtOAc=1:1) to give N-(2-chloro-5-(4-(3,5-dimethylisoxazol-4-ylamino)pyrido[3,2-d]pyrimidin-6-yl)pyridin-3-yl)-2,4-difluorobenzenesulfonamide (0.021 g, 27%) as a yellow solid. 1H-NMR (CDCl3, Varian 400 MHz) δ 2.30 (3H, s), 2.45 (3H, s), 6.89-7.05 (2H, m), 7.27 (1H, s), 7.79-7.92 (1H, m), 8.20 (1H, d, J=8.8 Hz), 8.26 (1H, s), 8.36 (1H, d, J=8.8 Hz), 8.73 (1H, s), 8.76 (1H, s), 8.89 (1H, s). m/z=544.1 [M+1]+.

Example 28

N-(2-chloro-5-(4-(6-methoxypyridin-3-ylamino)pyrido[3,2-d]pyrimidin-6-yl)pyridin-3-yl)-2,4-difluorobenzenesulfonamide

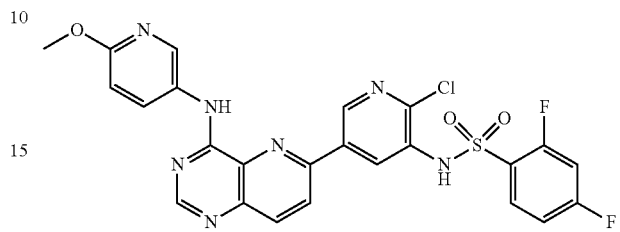

A mixture of 6-chloro-N-(6-methoxypyridin-3-yl)pyrido[3,2-d]pyrimidin-4-amine (Intermediate 22) (0.040 g, 0.139 mmol), N-(2-chloro-5-(4,4,5,5-tetramethyl-1,3,2-dioxaborolan-2-yl)pyridine-3-yl)-2,4-difluorobenzenesulfonamide (Intermediate 3) (0.066 g, 0.153 mmol), PdCl2(dppf)-CH2Cl2Adduct (0.011 g, 0.014 mmol) and 1 N aq. sodium bicarbonate (0.278 ml, 0.278 mmol) in dioxane (1.40 ml) subjected to microwave irradiation for 1 hour at 110° C. After cooling to room temperature, the reaction mixture was filtered through Celite and washed with CH2Cl2. The filtrate was concentrated in vacuo. The residue was purified by column chromatography on SiO2 (Hex:EtOAc=1:1) to give N-(2-chloro-5-(4-(6-methoxypyridin-3-ylamino)pyrido[3,2-d]pyrimidin-6-yl)pyridin-3-yl)-2,4-difluorobenzenesulfonamide (0.024 g, 31%) as a yellow solid.

1H-NMR (DMSO-d6, Varian 400 MHz) δ 3.89 (3H, s), 6.94 (3H, s), 6.89-7.05 (1H, d, J=8.4 Hz), 7.17-7.28 (1H, m), 7.50-7.65 (1H, m), 7.74-7.86 (1H, m), 8.17 (1H, dd, J=2.4, 8.8 Hz), 8.33 (1H, d, J=8.8 Hz), 8.36 (1H, d, J=8.8 Hz), 8.57 (1H, d, J=8.8 Hz), 8.62 (2H, s), 8.82 (1H, s), 9.48 (1H, s), 10.33 (1H, s), 10.98 (1H, br s). m/z=556.2 [M+1]+.

Example 29

N-(2-chloro-5-(4-(4-(trifluoromethoxy)phenylamino)pyrido[3,2-d]pyrimidin-6-yl)pyridin-3-yl)-2,4-difluorobenzenesulfonamide

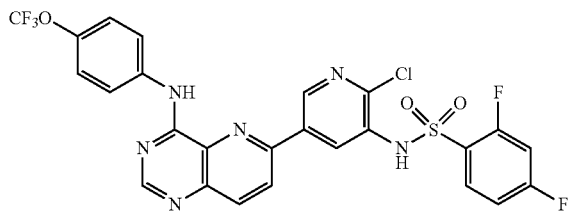

A mixture of 6-chloro-N-(4-(trifluoromethoxy)phenyl)pyrido[3,2-d]pyrimidin-4-amine (Intermediate 23) (0.050 g, 0.147 mmol), N-(2-chloro-5-(4,4,5,5-tetramethyl-1,3,2-dioxaborolan-2-yl)pyridine-3-yl)-2,4-difluorobenzenesulfonamide (Intermediate 3) (0.070 g, 0.161 mmol), PdCl2 (dppf)-CH2Cl2Adduct (5.99 mg, 7.34 μmol) and 1 N aq. sodium bicarbonate (0.294 ml, 0.294 mmol) in dioxane (1.40 ml) subjected to microwave irradiation for 1 hour at 110° C. After cooling to room temperature, the reaction mixture was filtered through Celite and washed with CH2Cl2. The filtrate was concentrated in vacuo. The residue was purified by column chromatography on SiO2 (Hex:EtOAc=1:1) to give N-(2-chloro-5-(4-(4-(trifluoromethoxy)phenylamino)pyrido

[3,2-d]pyrimidin-6-yl)pyridin-3-yl)-2,4-difluorobenzene-sulfonamide (0.049 g, 55%) as a yellow solid.

1H-NMR (CDCl3, Varian 400 MHz) δ 6.88-7.05 (2H, m), 7.34 (2H, d, J=8.8 Hz), 7.85-7.95 (1H, m), 8.05-8.10 (2H, m), 8.19 (1H, d, J=8.8 Hz), 8.34 (1H, d, J=8.4 Hz), 8.84 (1H, s), 8.85-8.90 (2H, m), 9.26 (1H, br s). 1NH was not detected. m/z=609.1 [M+1]+.

Example 30 tert-butyl 4-(6-(6-chloro-5-(2,4-difluorophenylsulfonamido)pyridin-3-yl)pyrido[3,2-d]pyrimidin-4-ylamino)piperidine-1-carboxylate

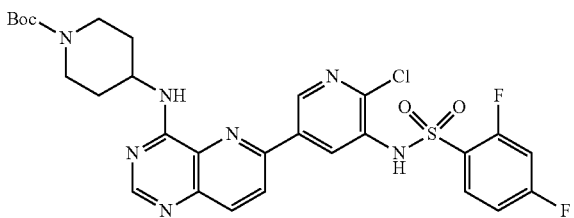 [SMILES: CC(C)(C)OC(=O)N1CCC(Nc2ncnc3ccc(-c4cnc(Cl)c(NS(=O)(=O)c5ccc(F)cc5F)c4)nc23)CC1]

A mixture of tert-butyl 4-(6-chloropyrido[3,2-d]pyrimidin-4-ylamino)piperidine-1-carboxylate (Intermediate 24) (0.050 g, 0.137 mmol), N-(2-chloro-5-(4,4,5,5-tetramethyl-1,3,2-dioxaborolan-yl)pyridine-3-yl)-2,4-difluorobenzene-sulfonamide (Intermediate 3) (0.065 g, 0.151 mmol), PdCl2(dppf)-CH2Cl2Adduct (5.61 mg, 6.87 µmol) and 1 N aq. sodium bicarbonate (0.275 ml, 0.275 mmol) in dioxane (1.40 ml) subjected to microwave irradiation for 1 hour at 110° C. After cooling to room temperature, the reaction mixture was filtered through Celite and washed with CH2Cl2. The filtrate was concentrated in vacuo. The residue was purified by prep TLC (Hex:EtOAc=1:2) to give tert-butyl 4-(6-(6-chloro-5-(2,4-difluorophenylsulfonamido)pyridin-3-yl)pyrido[3,2-d]pyrimidin-4-ylamino)piperidine-1-carboxylate (3.90 mg, 4.5%) as a yellow solid. 1H-NMR (CDCl3, Varian 400 MHz) δ 1.48 (9H, s), 1.55-1.72 (2H, m), 2.05-2.22 (2H, m), 2.92-3.12 (2H, m), 4.02-4.25 (2H, m), 4.30-4.48 (1H, m), 6.90-7.04 (2H, m), 7.14 (1H, J=8.0 Hz), 7.80-7.92 (1H, m), 8.07 (1H, d, J=8.8 Hz), 8.22 (1H, d, J=8.8 Hz), 8.69 (1H, s), 8.70 (1H, br s), 8.79 (1H, br s). m/z=632.2 [M+1]+.

Example 31

N-(2-chloro-5-(4-(piperidin-4-ylamino)pyrido[3,2-d]pyrimidin-6-yl)pyridine-3-yl)-2,4-difluorobenzene-sulfonamide

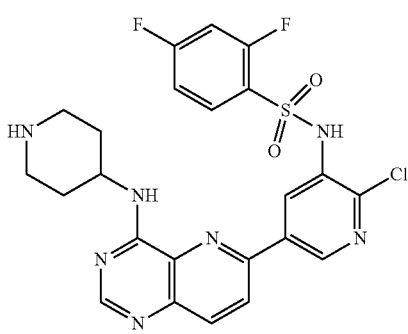 [SMILES: O=S(=O)(Nc1cc(-c2ccc3ncnc(NC4CCNCC4)c3n2)cnc1Cl)c1ccc(F)cc1F]

Step A: tert-butyl 4-(6-chloropyrido[3,2-d]pyrimidin-4-ylamino)piperidine-1-carboxylate

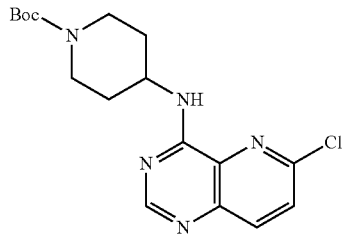 [SMILES: CC(C)(C)OC(=O)N1CCC(Nc2ncnc3ccc(Cl)nc23)CC1]

Hunig's base (6.53 mL, 37.5 mmol) was added to a suspension of 4,6-dichloropyrido[3,2-d]pyrimidine (intermediate 1, 5.00 g, 25.0 mmol) and tert-butyl-4-aminopiperidine-1-carboxylate (6.00 g, 30.0 mmol) in 1,4-dioxane (250 mL) at room temperature. The reaction mixture was refluxed for 1 h, and cooled to room temperature. The solvent was removed under reduced pressure, EtOAc and water were poured into the residue, and the separated aqueous layer was extracted with EtOAc. The combined organic layers were washed with brine, dried over Na2SO4, filtered, and concentrated in vacuo. The residue was purified by column chromatography (EtOAc) to give a pale yellow solid which was washed with MeOH afforded tert-butyl 4-(6-chloropyrido[3,2-d]pyrimidin-4-ylamino)piperidine-1-carboxylate (8.72 g, 96%) as a off white solid. 1H-NMR (CDCl3, Varian 400 MHz) δ 1.49 (9H, s), 1.50-1.62 (2H, m), 2.10-2.15 (2H, m), 2.98-3.01 (2H, m), 4.01-4.25 (2H, m), 4.25-4.40 (1H, m), 6.86 (1H, d, J=7.6 Hz), 7.62 (1H, d, J=8.8 Hz), 8.04 (1H, d, J=8.8 Hz), 8.62 (1H, s).

Step B: tert-butyl 4-(6-(6-chloro-5-(2,4-difluorophenylsulfonamido)pyridin-3-yl)pyrido[3,2-d]pyrimidin-4-ylamino)piperidine-1-carboxylate

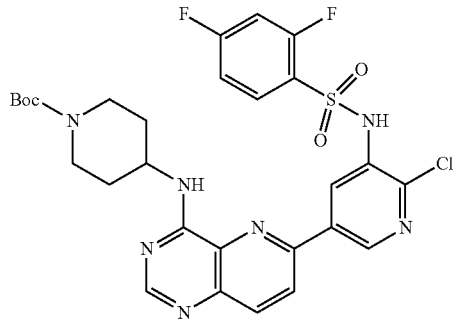 [SMILES: CC(C)(C)OC(=O)N1CCC(Nc2ncnc3ccc(-c4cnc(Cl)c(NS(=O)(=O)c5ccc(F)cc5F)c4)nc23)CC1]

A mixture of 4-(6-chloropyrido[3,2-d]pyrimidin-4-ylamino)piperidine-1-carboxylate (8.52 g, 23.4 mmol), N-(2-chloro-5-(4,4,5,5-tetramethyl-1,3,2-dioxborolan-2-yl)pyridine-3-yl)-2,4-difluorobenzenesulfoneamide (intermediate 2, 11.09 g, 25.8 mmol), PdCl2(dppf)-CH2Cl2 (955 mg, 1.17 mmol), and NaHCO3 (3.93 g, 46.8 mmol) in 1,4-dioxane/H2O (v/v=2.4/1, 170 mL) was refluxed for 3 h. The solvents were removed after cooling, EtOAc and water were poured into the residue, and the separated aqueous layer was extracted with EtOAc. The combined organic layers were washed with brine, dried over Na2SO4, filtered, and concentrated in vacuo. The residue was purified by column chromatography (EtOAc:MeOH=50:1) to give a pale yellow solid which was washed with MeOH afforded tert-butyl 4-(6-(6-chloro-5-(2,4-difluorophenylsulfonamido)pyridin-3-yl)pyrido[3,2-d]pyrimidin-4-ylamino)piperidine-1-carboxylate (13.6 g, 92%) as a white solid. $^1$H-NMR (CDCl$_3$, Varian 400 MHz) δ 1.49 (9H, s), 1.56-1.68 (2H, m), 2.13-2.24 (2H, m), 2.96-3.14 (2H, m), 4.06-4.24 (2H, m), 4.14-4.45 (1H, m), 6.92-7.02 (2H, m), 7.13 (1H, d, J=8.0 Hz), 7.82-7.90 (1H, m), 8.08 (1H, d, J=8.4 Hz), 8.22 (1H, d, J=8.4 Hz), 8.66 (1H, s), 8.73 (1H, d, J=2.0 Hz), 8.81 (1H, d, J=2.0 Hz). NH peak was not observed.

Step C: N-(2-chloro-5-(4-(piperidin-4-ylamino)pyrido[3,2-d]pyrimidin-6-yl)pyridine-3-yl)-2,4-difluorobenzenesulfonamide

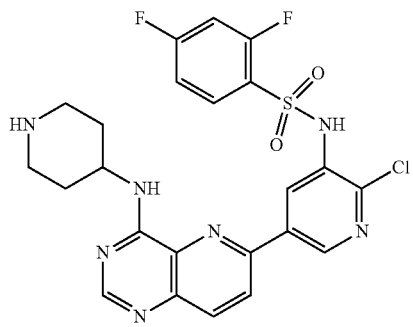 [SMILES: O=S(=O)(Nc1cc(-c2ccc3ncnc(NC4CCNCC4)c3n2)cnc1Cl)c1ccc(F)cc1F]

To a solution of tert-butyl 4-(6-(6-chloro-5-(2,4-difluorophenylsulfonamido)pyridin-3-yl)pyrido[3,2-d]pyrimidin-4-ylamino)piperidine-1-carboxylate (1.28 g, 2.03 mmol) in DCM (20 mL) was added TFA (3.10 mL, 40.5 mmol) at 0° C. The reaction mixture was stirred for 4 h at room temperature and removed the solvent in vacuo. DCM was poured into the residue, and neutralized with aq. Na$_2$HCO$_3$. The resulting solid was filtered and washed with MeOH and EtOAc to give N-(2-chloro-5-(4-(piperidin-4-ylamino)pyrido[3,2-d]pyrimidin-6-yl)pyridine-3-yl)-2,4-difluorobenzenesulfonamide (954 mg, 89%) as a pale yellow solid. $^1$H-NMR (DMSO-d6, Varian 400 MHz) δ 1.84-2.00 (2H, m), 2.12-2.24 (2H, m), 3.04-3.18 (2H, m), 3.32-3.46 (2H, m), 4.38-4.52 (1H, m), 7.07 (1H, dt, J=2.0, 8.4 Hz), 7.22 (1H, dt, J=2.4, 10.0 Hz), 7.83-7.92 (1H, m), 8.04 (1H, d, J=8.0 Hz), 8.11 (1H, d, J=8.8 Hz), 8.19 (1H, d, J=8.8 Hz), 8.26 (1H, d, J=2.4 Hz), 8.43 (2H, brs), 8.52 (1H, s), 8.59 (1H, d, J=2.4 Hz). m/z=532.2 [M+1]$^+$.

Example 32 isopropyl 4-(6-(6-chloro-5-(2,4-difluorophenylsulfonamido)pyridine-3-yl)pyrido[3,2-d]pyrimidin-4-ylamino)piperidine-1-carboxylate

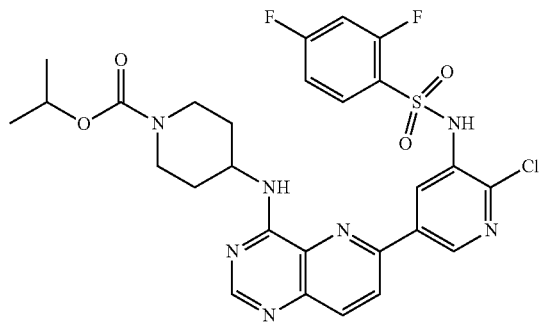 [SMILES: CC(C)OC(=O)N1CCC(Nc2ncnc3ccc(-c4cnc(Cl)c(NS(=O)(=O)c5ccc(F)cc5F)c4)nc23)CC1]

To a solution of tert-butyl 4-(6-(6-chloro-5-(2,4-difluorophenylsulfonamido)pyridin-3-yl)pyrido[3,2-d]pyrimidin-4-ylamino)piperidine-1-carboxylate (12.0 g, 19.0 mmol; prepared as in Example 1, Step B) in DCM (300 mL) was added HCl (4 M in 1,4-dioxane) at 0° C., and the reaction mixture was stirred for 4 h at room temperature. The solvent was removed by evaporation, and the obtained crude N-(2-chloro-5-(4-(piperidin-4-ylamino)pyrido[3,2-d]pyrimidin-6-yl)pyridine-3-yl)-2,4-difluorobenzenesulfonamide HCl salt was used for the next step without further purification. TEA (26.4 mL, 190 mmol) was added to a suspension of above obtained HCl salt in DCM (300 mL) at 0° C. The mixture was stirred for 1 h at room temperature and isopropyl carbonochloridate (19.0 mL, 19.0 mmol) was added to the reaction mixture at 0° C. The reaction mixture was stirred for 2 h at room temperature. DCM and water were poured into the residue, and the separated aqueous layer was extracted with DCM, the combined organic layers were washed with brine, dried over Na$_2$SO$_4$, filtered, and concentrated in vacuo. The residue was purified by column chromatography (EtOAc:MeOH=20:1) to give isopropyl 4-(6-(6-chloro-5-(2,4-difluorophenylsulfonamido)pyridine-3-yl)pyrido[3,2-d]pyrimidin-4-ylamino)piperidine-1-carboxylate (9.87 g, 84%) as a pale yellow solid. $^1$H-NMR (DMSO-d6, Varian 400 MHz) δ 1.21 (6H, d, J=6.4 Hz), 1.62-1.78 (2H, m), 1.85-1.95 (2H, m), 2.82-3.08 (2H, m), 4.02-4.17 (2H, m), 4.40-4.54 (1H, m), 4.77-4.83 (1H, m), 7.22 (1H, dt, J=2.4, 8.8 Hz), 7.53-7.61 (1H, m), 7.74-7.83 (1H, m), 8.21 (1H, d, J=8.8 Hz), 8.42 (1H, d, J=10.8 Hz), 8.46 (1H, d, J=8.8 Hz), 8.54 (1H, s), 8.66 (1H, d, J=2.4 Hz), 9.39 (1H, d, J=2.4 Hz). NH peak was not observed. m/z=618.2 [M+1]$^+$.

Example 33

4-(6-(6-chloro-5-(2,4-difluorophenylsulfonamido)pyridine-3-yl)pyrido[3,2-d]pyrimidin-4-ylamino)-N-isopropylpiperidine-1-carboxamide

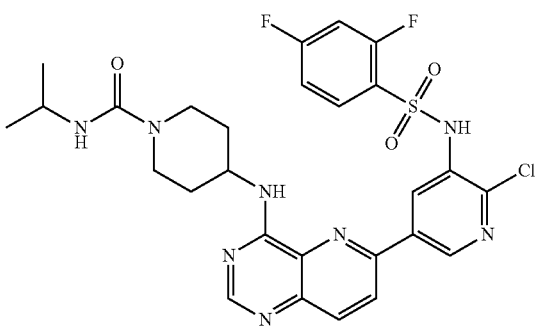 [SMILES: CC(C)NC(=O)N1CCC(Nc2ncnc3ccc(-c4cnc(Cl)c(NS(=O)(=O)c5ccc(F)cc5F)c4)nc23)CC1]

The title compound was prepared as described in Example 2 using 2-isocyanatopropane in place of isopropyl chloroformate. $^1$H-NMR (CDCl$_3$, Varian 400 MHz) δ 1.17 (6H, d, J=6.4 Hz), 1.60-1.74 (2H, m), 2.15-2.26 (2H, m), 3.04-3.16 (2H, m), 3.92-4.06 (3H, m), 4.31 (1H, d, J=7.6 Hz), 4.32-4.47 (1H, m), 6.92-7.03 (2H, m), 7.15 (1H, d, J=8.4 Hz), 7.82-7.90 (1H, m), 8.09 (1H, d, J=8.8 Hz), 8.22 (1H, J=8.8 Hz), 8.66 (1H, s), 8.73 (1H, d, J=2.0 Hz), 8.81 (1H, d, J=2.0 Hz). 1 NH peck was not observed. m/z=617.2 [M+1]$^+$.

Example 34

4-(6-(6-chloro-5-(2,4-difluorophenylsulfonamido)pyridine-3-yl)pyrido[3,2-d]pyrimidin-4-ylamino)-N,N-diethylpiperidine-1-carboxamide

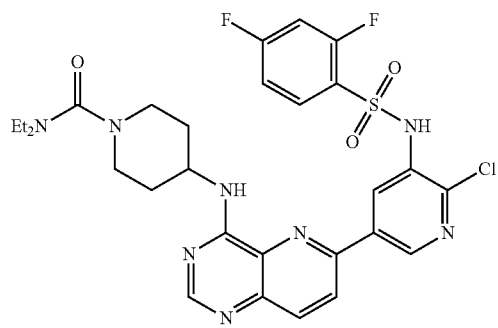

The title compound was prepared as described in Example 2 using diethylcarbamic chloride in place of isopropyl chloroformate. ¹H-NMR (DMSO-d6, Varian 400 MHz) δ 1.07 (6H, t, J=7.2 Hz), 1.71-1.86 (2H, m), 1.86-1.95 (2H, m), 2.81-2.92 (2H, m), 3.15 (4H, q, J=7.2 Hz), 3.58-3.68 (2H, m), 4.36-4.49 (1H, m), 7.18-7.26 (1H, m), 7.53-7.61 (1H, m), 7.74-7.83 (1H, m), 8.21 (1H, d, J=8.8 Hz), 8.45 (1H, brs), 8.46 (1H, d, J=8.8 Hz), 8.66 (1H, s), 9.40 (1H, s). 2 NH pecks were not observed. m/z=631.3 [M+1]⁺.

Example 35

N-(2-chloro-5-(4-(1morpholine-4-carbonyl)piperidine-4-ylamino)pyrido[3,2-d]pyrimidin-6-yl)pyridine-3-yl)-2,4-difluorobenzenesulfonamide

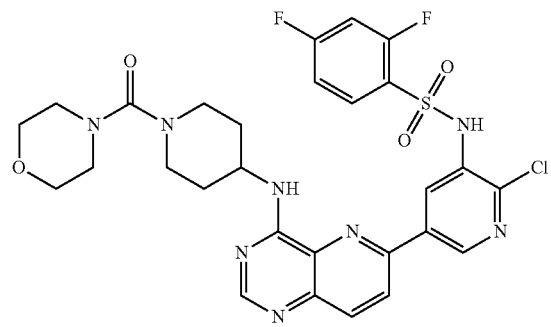 [SMILES: O=C(N1CCOCC1)N1CCC(Nc2ncnc3ccc(-c4cnc(Cl)c(NS(=O)(=O)c5ccc(F)cc5F)c4)nc23)CC1]

The title compound was prepared as described in Example 2 using morpholine-4-carbonyl chloride in place of isopropyl chloroformate. ¹H-NMR (DMSO-d6, Varian 400 MHz): δ 1.72-1.94 (4H, m), 2.92 (2H, t, J=12.4 Hz), 3.12-3.22 (4H, m), 3.56-3.68 (4H, m), 3.71 (2H, d, J=12.8 Hz), 4.38-4.50 (1H, m), 7.22 (1H, d, J=8.2 Hz), 7.59 (1H, d, J=9.0 Hz), 7.78 (1H, dd, J=8.6, 15.0 Hz), 8.21 (1H, d, J=8.8 Hz), 8.42-8.48 (2H, m), 8.53 (1H, s), 8.67 (1H, d, J=2.0 Hz), 9.39 (1H, d, J=1.6 Hz). 1 NH peak was not observed. m/z=645.3 [M+1]⁺.

Example 36

N-(2-chloro-5-(4-(1-(morpholine-4-carbonyl)piperidin-4-ylamino)pyrido[3,2-d]pyrimidin-6-yl)pyridine-3-yl)-2,4-difluorobenzenesulfonamide

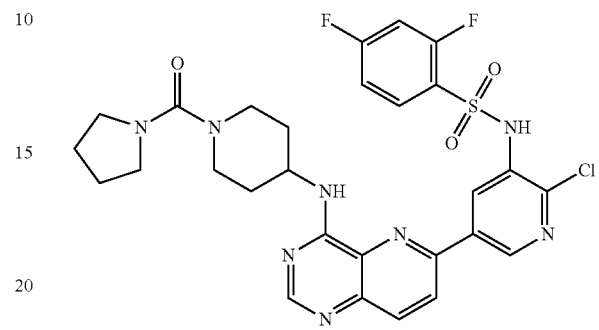

The title compound was prepared as described in Example 2 using pyrrolidine-1-carbonyl chloride in place of isopropyl chloroformate. ¹H-NMR (DMSO-d6, Varian 400 MHz): δ 1.20-1.30 (2H, m), 1.78-1.92 (2H, m), 2.85 (2H, t, J=12.0 Hz), 3.04-3.14 (4H, m), 3.18-3.30 (4H, m), 3.75 (2H, d, J=12.8 Hz), 4.38-4.48 (1H, m), 7.14 (1H, d, J=8.4 Hz), 7.40 (1H, d, J=9.4 Hz), 7.82 (1H, dd, J=7.8, 15.4 Hz), 8.14-8.28 (3H, m), 8.43 (1H, s), 8.50 (1H, s), 9.03 (1H, brs). 1 NH peak was not observed. m/z=629.2 [M+1]⁺.

Example 37

N-(5-(4-(1-(1,3,4-thiazol-2-yl)piperidin-4-ylamino)pyrido[3,2-d]pyrimidin-6-yl)-2-chloropyridin-3-yl)-2,4-difliorobenzenesulfonamide

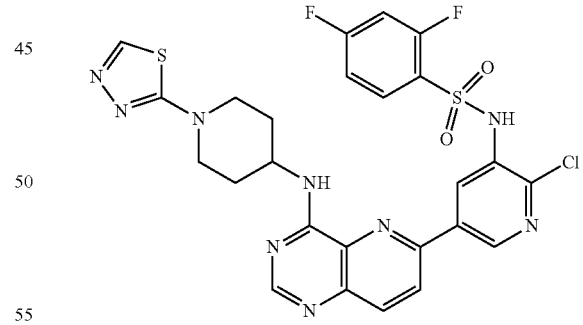

The title compound was prepared by N-alkylation of N-(2-chloro-5-(4-(piperidin-4-ylamino)pyrido[3,2-d]pyrimidin-6-yl)pyridine-3-yl)-2,4-difluorobenzenesulfonamide (prepared as in Example 1) with 2-bromo-1,3,4-thiadiazole. ¹H-NMR (CDCl₃, Varian 400 MHz) δ 1.80-1.96 (2H, m), 2.25-2.40 (2H, m), 3.42-3.56 (2H, m), 4.02-4.16 (2H, m), 4.43-4.58 (1H, m), 6.90 (2H, m), 7.12-7.30 (2H, m), 7.78-7.90 (1H, m), 8.10 (1H, d, J=8.8 Hz), 8.24 (1H, d, J=8.8 Hz), 8.48 (1H, s), 8.68 (1H, s), 8.75 (1H, s), 8.81 (1H, s). m/z=616.3 [M+1]⁺.

Example 38

N-(2-chloro-5-(4-(1-(pyrimidin-2-yl)piperidin-4-ylamino)pyrido[3,2-d]pyrimidin-6-yl)pyridine-3-yl)-2,4-difluorobenzenesulfonamide

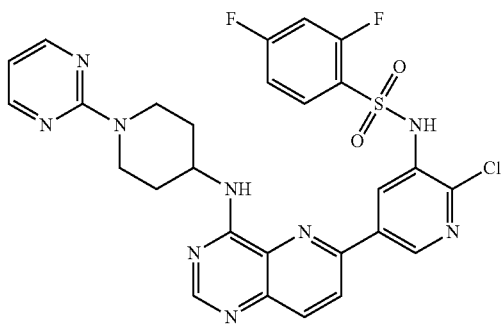

Step A: tert-butyl 1-(pyrimidine-2-yl)piperidin-4-ylcarbamate

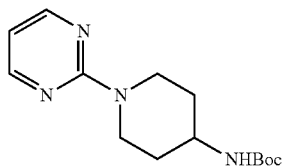 [SMILES: CC(C)(C)OC(=O)NC1CCN(c2ncccn2)CC1]

A mixture of tert-butyl piperidin-4-ylcarbamate (2.00 g, 9.99 mmol), 2-chloropyrimidine (3.43 g, 30.0 mmol), and $K_2CO_3$ (6.90 g, 49.9 mmol) in 1,4-dioxane (57 mL) was refluxed for 2 days. After cooled to room temperature, the mixture was filtered and washed with EtOAc. The filtrate was concentrated in vacuo, and the residue was purified by column chromatography (Hexane:EtOAC=3:1) to give tert-butyl 1-(pyrimidine-2-yl)piperidin-4-ylcarbamate (2.78 g, quant.) as a white solid. $^1$H-NMR (CDCl$_3$, Varian 400 MHz) δ 1.23-1.44 (2H, m), 1.45 (9H, s), 1.95-2.08 (2H, m), 2.99-3.10 (2H, m), 3.72 (1H, brs), 4.39-4.53 (1H, m), 4.59-4.69 (2H, m), 6.47 (1H, t, J=4.8 Hz), 8.29 (2H, d, J=4.8 Hz). m/z=278.87 [M+1]$^+$.

Step B: 1-(pyrimidin-2-yl)piperidin-4-amine

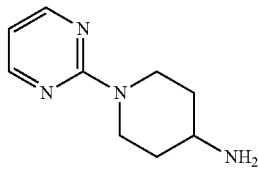 [SMILES: NC1CCN(c2ncccn2)CC1]

TFA (7.87 mL, 103 mmol) was added to a solution of tert-butyl 1-(pyrimidine-2-yl)piperidin-4-ylcarbamate (2.86 g, 10.3 mmol) in DCM (60 mL) at at 0° C. The reaction mixture was stirred for 2 h at room temperature and removed the solvent under reduced pressure. The residue was re-dissolved in DCM, and neutralized with aq. Na$_2$HCO$_3$. The solvents were removed by evaporation, the resulting residue was purified by column chromatography (DCM:MeOH:NH$_4$OH=10: 1:0.1) to give 1-(pyrimidin-2-yl)piperidin-4-amine (1.68 g, 92%) as a white solid. $^1$H-NMR (CD$_3$OD, Varian 400 MHz) δ 1.26-1.37 (2H, m), 1.75-1.99 (2H, m), 2.76-2.98 (2H, m), 2.86-3.05 (1H, m), 4.64-4.72 (2H, m), 6.53 (1H, t, J=4.8 Hz), 8.27 (2H, d, J=4.8 Hz). m/z=179.04 [M+1]$^+$.

Step C: 6-chloro-N-(1-pyrimidin-2-yl)pyrido[3,2-d]pyrimidin-4-amine

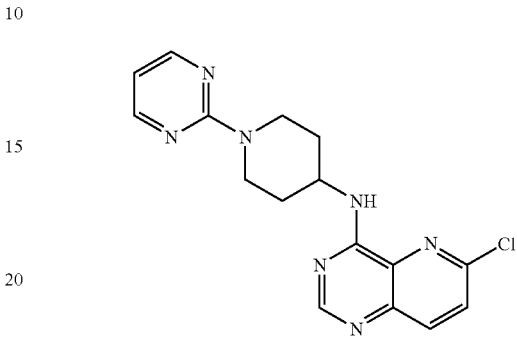

Hunig's base (1.59 mL, 9.15 mmol) was added to suspension of 4,6-dichloropyrido[3,2-d]pyrimidine (1.22 g, 6.10 mmol) and 1-(pyrimidin-2-yl)piperidin-4-amine (1.31 g, 7.32 mmol) in 1,4-dioxane (44 mL) at room temperature. The reaction mixture was refluxed for 1 h, and cooled to room temperature. The solvent was removed under reduced pressure, DCM and water were poured into the residue, and the separated aqueous layer was extracted with DCM. The combined organic layers were washed with brine, dried over Na$_2$SO$_4$, filtered, and concentrated in vacuo. The residue was purified by column chromatography (EtOAc:MeOH=50:1) to give 6-chloro-N-(1-pyrimidin-2-yl)pyrido[3,2-d]pyrimidin-4-amine (1.90 g, 91%) as a pale yellow solid. $^1$H-NMR (DMSO-d6, Varian 400 MHz) δ 1.65-1.80 (2H, m), 1.88-1.96 (2H, m), 2.95-3.06 (2H, m), 4.92-4.55 (1H, m), 4.70-4.80 (2H, m), 6.62 (1H, t, J=4.8 Hz), 7.87 (1H, d, J=8.8 Hz), 8.15 (1H, d, J=8.8 Hz), 8.29 (1H, d, J=8.4 Hz), 8.37 (2H, d, J=4.8 Hz), 8.54 (1H, s). m/z=342.08 [M+1]$^+$.

Step D: N-(2-chloro-5-(4-(1-(pyrimidin-2-yl)piperidin-4-ylamino)pyrido[3,2-d]pyrimidin-6-yl)pyridine-3-yl)-2,4-difluorobenzenesulfoneamide

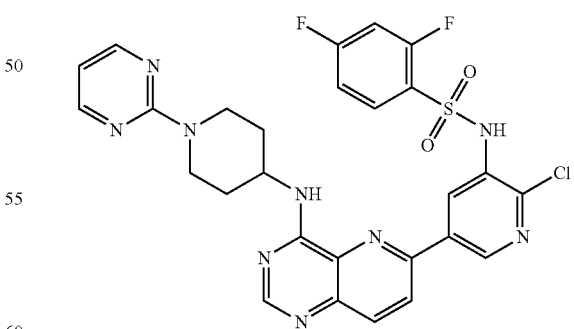

A mixture of 6-chloro-N-(1-pyrimidin-2-yl)pyrido[3,2-d]pyrimidin-4-amine (369 mg, 1.08 mmol), N-(2-chloro-5-(4,4,5,5-tetramethyl-1,3,2-dioxborolan-2-yl)pyridine-3-yl)-2,4-difluorobenzenesulfoneamide (intermediate 2, 511 mg, 1.19 mmol), PdCl$_2$(dppf)-CH$_2$Cl$_2$ (44.1 mg, 0.05 mmol), and NaHCO$_3$ (181 mg, 2.16 mmol) in 1,4-dioxane/H$_2$O (v/v=2.4/

1, 7.8 mL) was refluxed for 1 h. The solvents were removed after cooling, CHCl₃ and water were poured into the residue, and the separated aqueous layer was extracted with CHCl₃/IPA=3:1. The combined organic layers were washed with brine, dried over Na₂SO₄, filtered, and concentrated in vacuo. The residue was purified by column chromatography (EtOAc:MeOH=20:1) to give N-(2-chloro-5-(4-(1-(pyrimidin-2-yl)piperidin-4-ylamino)pyrido[3,2-d]pyrimidin-6-yl)pyridine-3-yl)-2,4-difluorobenzenesulfonamide (598 mg, 91%) as a pale yellow solid. ¹H-NMR (CDCl₃, Varian 400 MHz) δ 1.64-1.76 (2H, m), 2.22-2.33 (2H, m), 3.22-3.34 (2H, m), 4.47-4.60 (1H, m), 4.72-4.82 (2H, m), 6.50 (1H, t, J=4.8 Hz), 6.88-7.00 (2H, m), 7.17 (1H, d, J=8.0 Hz), 7.80-7.88 (1H, m), 8.08 (1H, d, J=8.8 Hz), 8.23 (1H, d, J=8.8 Hz), 8.33 (1H, d, J=4.4 Hz), 8.68 (1H, s), 8.71 (1H, d, J=2.4 Hz), 8.80 (1H, d, J=2.4 Hz). 2 NH peaks were not observed. m/z=610.2 [M+1]⁺.

Example 39

N-(2-chloro-5-(4-(1-(pyridin-2-yl)piperidin-4-ylamino)pyrido[3,2-d]pyrimidin-6-yl)pyridin-3-yl)-2,4-difluorobenzenesulfonamide

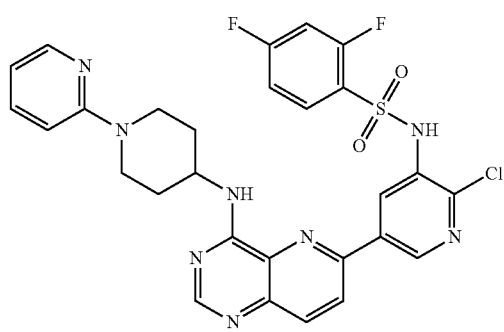 [SMILES: O=S(=O)(Nc1cc(-c2ccc3ncnc(NC4CCN(c5ccccn5)CC4)c3n2)cnc1Cl)c1ccc(F)cc1F]

Step A: tert-butyl 1-(pyridin-2-yl)piperidin-4-ylcarbamate

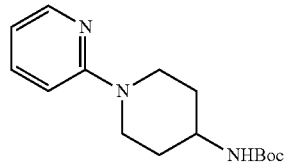 [SMILES: CC(C)(C)OC(=O)NC1CCN(c2ccccn2)CC1]

The reaction mixture of tert-butyl piperidin-4-ylcarbamate (200 mg, 0.10 mmol), 2-bromopyridine (205 mg, 1.30 mmol), Pd₂(dba)₃ (18.0 mg, 0.02 mmol), Xantphos (35.0 mg, 0.06 mmol) and Cs₂CO₃ (490 mg, 1.50 mmol) was heated at 100° C. for 1 day. Additional 2-bromopyridine (205 mg, 1.30 mmol), Pd₂(dba)₃ (18.0 mg, 0.02 mmol), Xantphos (35.0 mg, 0.06 mmol), Cs₂CO₃ (490 mg, 1.50 mmol) were added to the reaction mixture, and heated at 100° C. for 1 day. The reaction mixture was cooled to room temperature, diluted with EtOAc and water. The separated aqueous layer was extracted with EtOAc, the combined organic layers were dried over Na₂SO₄, filtered, and concentrated in vacuo. The residue was purified by column chromatography (EtOAc) to give tert-butyl 1-(pyridin-2-yl)piperidin-4-ylcarbamate (86.8 mg, 31%) as a pale yellow solid. m/z=278.06 [M+1]⁺.

Step B: N-(2-chloro-5-(4-(1-(pyridin-2-yl)piperidin-4-ylamino)pyrido[3,2-d]pyrimidin-6-yl)pyridin-3-yl)-2,4-difluorobenzenesulfonamide

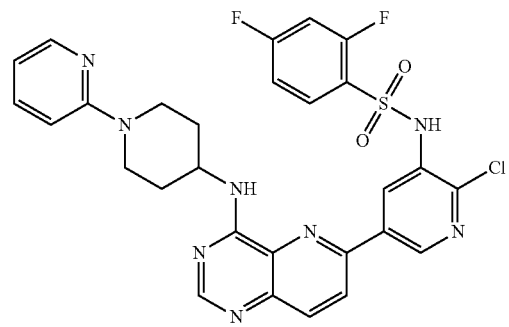 [SMILES: O=S(=O)(Nc1cc(-c2ccc3ncnc(NC4CCN(c5ccccn5)CC4)c3n2)cnc1Cl)c1ccc(F)cc1F]

The title compound was prepared as described in Example 8, Step B, C, and D. ¹H NMR (CDCl₃, Varian 400 MHz) δ 1.72-1.81 (2H, m), 2.27-2.31 (2H, m), 3.19-3.26 (2H, m), 4.31-4.34 (2H, m), 4.47-4.51 (1H, m), 6.61-6.64 (1H, m), 6.74 (1H, d, J=8.8 Hz), 6.90-6.99 (2H, m) 7.17 (1H, d, J=7.6 Hz), 7.47-7.51 (1H, m), 7.81-7.86 (1H, m), 8.08 (1H, d, J=8.8 Hz), 8.19-8.21 (1H, m), 8.22 (1H, d, J=8.8 Hz), 8.68 (1H, s), 8.72 (1H, d, J=2.0 Hz), 8.80 (1H, d, J=2.0 Hz). 1 NH peak was not observed. m/z=609.2 [M+1]⁺.

Example 40

N-(2-chloro-5-(4-(1-(pyridine-3-yl)piperidin-4-ylamino)pyrido[3,2-d]pyrimidin-3-yl)-2,4-difluorobenzenesulfonamide

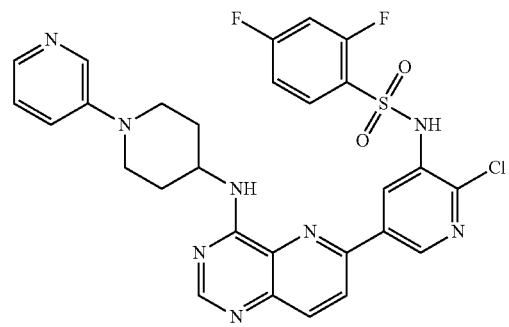

The title compound was prepared as described in Example 9 using 3-bromopyridine in place of 2-bromopyridine. ¹H-NMR (CDCl₃, Varian 400 MHz) δ 1.83-1.96 (2H, m), 2.29-2.39 (2H, m), 3.06-3.17 (2H, m), 3.51-3.80 (2H, m), 4.38-4.50 (1H, m), 6.89-7.01 (2H, m), 7.17-7.25 (2H, m), 7.79-7.88 (1H, m), 8.09 (1H, d, J=8.8 Hz), 8.11 (1H, brs), 8.23 (1H, d, J=8.8 Hz), 8.39 (1H, brs), 8.68 (1H, s), 8.75 (1H, d, J=2.0 Hz), 8.82 (1H, d, J=2.0 Hz). 2 NH pecks were not observed. m/z=609.2 [M+1]⁺.

Example 41

N-(2-chloro-5-(4-(1-(6-methylpyridin-4-ylamino)pyrido[3,2-d]pyrimidin-6-yl)pyridine-3-yl)-2,4-difluorobenzenesulfonamide

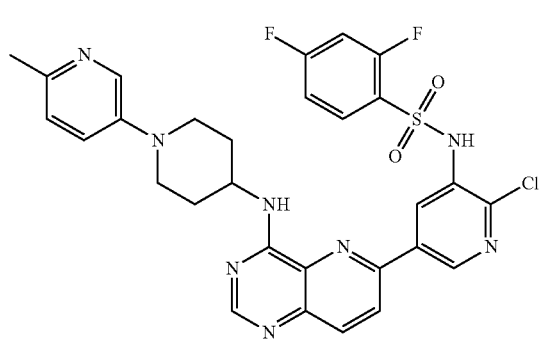 [SMILES: Cc1ccc(N2CCC(Nc3ncnc4ccc(-c5cnc(Cl)c(NS(=O)(=O)c6ccc(F)cc6F)c5)nc34)CC2)cn1]

The title compound was prepared as described in Example 9 using 5-bromo-2-methylpyridine in place of 2-bromopyridine. ¹H-NMR (CDCl₃, Varian 400 MHz) δ 1.84-1.96 (2H, m), 2.27-2.37 (2H, m), 2.47 (3H, s), 3.02-3.12 (2H, m), 3.63-3.72 (2H, m), 4.36-4.46 (1H, m), 6.89-7.02 (2H, m), 7.05 (1H, d, J=8.4 Hz), 7.17-7.25 (2H, m), 7.80-7.88 (1H, m), 8.09 (1H, d, J=8.8 Hz), 8.23 (1H, d, J=8.8 Hz), 8.26 (1H, d, J=2.8 Hz), 8.67 (1H, s), 8.75 (1H, s), 8.81 (1H, d, J=2.0 Hz). 1 NH peak was not observed. m/z=623.2 [M+1]⁺.

Example 42

N-(2-chloro-5-(4-(1-(pyrazin-2-yl)piperidin-4-ylamino)pyrido[3,2-d]pyrimidin-6-yl)pyridine-3-yl)-2,4-difluorobenzenesulfonamide

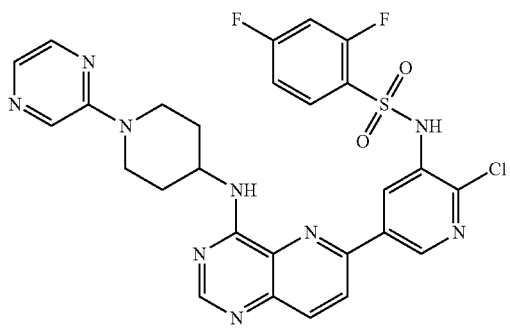 [SMILES: O=S(=O)(Nc1cc(-c2ccc3ncnc(NC4CCN(c5cnccn5)CC4)c3n2)cnc1Cl)c1ccc(F)cc1F]

The title compound was prepared as described in Example 9 using 2-bromopyrazine in place of 2-bromopyridine. ¹H-NMR (CDCl₃, Varian 400 MHz) δ 1.70-1.82 (2H, m), 2.26-2.38 (2H, m), 3.20-3.32 (2H, m), 4.31-4.42 (2H, m), 4.46-4.60 (1H, m), 6.90-7.00 (2H, m), 7.19 (1H, d, J=8.0 Hz), 7.78-7.98 (2H, m), 8.04-8.12 (2H, m), 8.19-8.28 (2H, m), 8.68 (1H, s), 8.72 (1H, s), 8.82 (1H, d, J=0.8 Hz). NH peak was not observed. m/z=610.2 [M+1]⁺.

Example 43

N-(2-chloro-5-(4-(1-(pyridazin-3-yl)piperidin-4-ylamino)pyrido[3,2-d]pyrimidin-6-yl)pyridin-3-yl)-2,4-difluorobenzenesulfonamide

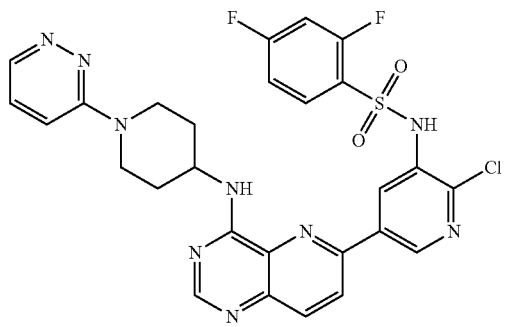 [SMILES: O=S(=O)(Nc1cc(-c2ccc3ncnc(NC4CCN(c5cccnn5)CC4)c3n2)cnc1Cl)c1ccc(F)cc1F]

Step A: tert-butyl 1-(pyridazine-3-yl)piperidin-4-ylcarbamate

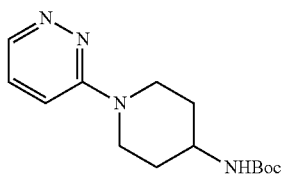 [SMILES: CC(C)(C)OC(=O)NC1CCN(c2cccnn2)CC1]

The reaction mixture of tert-butyl piperidin-4-ylcarbamate (250 mg, 1.25 mmol), 3-bromopyridazine (258 mg, 1.62 mmol), CsF (37.9 mg, 0.25 mmol), and K₂CO₃ (518 mg, 3.74 mmol) in DMSO (12.5 mL) was heated at 100° C. for 20 h. Water and DCM were poured into the mixture, and the separated aqueous layer was extracted with DCM, the combined organic layers were dried over Na₂SO₄, filtered, concentrated in vacuo. The residue was purified by column chromatography (Hexane:EtOAc=1:1) to give tert-butyl 1-(pyridazine-3-yl)piperidin-4-ylcarbamate (123 mg, 35%) as a pale yellow solid. ¹H-NMR (CDCl₃, Varian 400 MHz) δ 1.45 (9H, s), 1.92-2.12 (2H, m), 3.03-3.17 (2H, m), 3.55-3.80 (2H, m), 4.25-4.38 (2H, m), 4.52 (1H, brs), 6.92 (1H, d, J=9.2 Hz), 7.20 (1H, dd, J=4.4, 9.2 Hz), 8.56 (1H, d, J=4.4 Hz). NH peak was not observed. m/z=279.06 [M+1]⁺.

Step B: N-(2-chloro-5-(4-(1-(pyridazin-3-yl)piperidin-4-ylamino)pyrido[3,2-d]pyrimidin-6-yl)pyridin-3-yl)-2,4-difluorobenzenesulfonamide

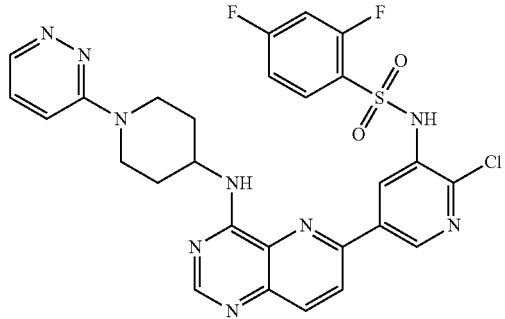 [SMILES: O=S(=O)(Nc1cc(-c2ccc3ncnc(NC4CCN(c5cccnn5)CC4)c3n2)cnc1Cl)c1ccc(F)cc1F]

The title compound was prepared as described in Example 9. ¹H NMR (CDCl₃, Varian 400 MHz) δ 1.75-1.84 (2H, m), 2.31-2.34 (2H, m), 3.31-3.37 (2H, m), 4.43-4.46 (2H, m), 4.55-4.57 (1H, m), 6.92-7.01 (3H, m), 7.18-7.25 (1H, m), 7.8-7.86 (1H, m) 8.09 (1H, d, J=8.8 Hz), 8.23 (1H, d, J=8.8 Hz), 8.59-8.6 (1H, m), 8.68 (1H, s), 8.72-8.73 (1H, m), 8.79-8.8 (1H, m). 2 NH peaks were not observed. m/z=610.2 [M+1]$^+$.

Biological Activity

Materials and Preparation of Reagents

The PI3 Kinase Activity/Inhibitor Assay Kit was purchased from Millipore. The dimethylsulfoxide was purchased from Sigma-Aldrich.

Assay Principle

The PI3 Kinase Activity/Inhibitor Assay is a competitive assay used for the fast and sensitive quantitation of activity of the four class I PI3 kinases (p110 α, β, γ, δ). The PI3 Kinase Activity/Inhibitor Assay works on the principle that PI3 Kinase phosphorylates PI(3,4)P2 (PIP2), converting it to PI(3,4,5)P3 (PIP3). The PH domain of the protein GRP-1 binds PIP3 with high affinity and specificity. The kit includes this recombinant protein that is used as the capture protein. This protein binds to the glutathione plate and captures either the PIP3 generated as part of the kinase reaction or the biotinylated-PIP3 tracer included in the kit. The captured biotinylated-PIP3 is detected using streptavidin-HRP conjugate and a colorimetric read out (OD 450). The lower the signal, the higher the PI3 Kinase activity.

Assay Protocol

PI3-Kinase included in the Kit was diluted at the ratio of 1:10 with distilled water and stored on ice. The compound was prepared by diluting the stock compound to 100× of the final concentration and then diluted again at the ratio of 1:50 to make 2× of the final concentration with distilled water.

The prepared PI3-Kinase (5 μL/well) and the compound (5 μL/well) were added to Glutathione-Coated Plate and pre-incubated at room temperature for 10 minutes. After adding 5 μL of 5× Kinase reaction buffer per well, PIP2 was diluted at the ratio of 1:20 with distilled water and 54, were added into each well. Distilled water was added up to 25 μL, and the reaction mixture was incubated at room temperature for an hour. Biotinylated-PIP3 was diluted at the ratio of 1:18 with 1×TBS solution and 25 μL of the mixture were put in each well excluding the buffer control well. GRP1-GST was diluted at the ratio of 1:1000 with 1×TBS solution and 50 μL of it was added to every well. The mixture was incubated at room temperature for an hour.

After removing the solution contained in the wells, the wells were washed 4 times with 200 μL of 1×TBST. SA-HRP was diluted at the ratio of 1:2000 with 1×TBST, then 50 μL of it was added into every well and incubated at room temperature for an hour. Again after removing the solution, they were washed 5 times by adding 200 μL of 1×TBST to each well. 100 μL of TMB solution was added to every well. The plate was developed in the dark for 5-20 minutes. As blue color appeared, the reaction was stopped by adding 100 μL of stop solution to every well, and the plate was read at 450 nm with ELISA Reader (TECAN).

Data Analysis

For the calculation of relative percentage to biotinylated-PIP3, we take the direct absorbance at 450 nm (A450) and set the positive Biotinylated-PIP3 wells as 100 percentage. All the other signals are divided by the Biotinylated-PIP3 average, and multiplied by 100 to show the relative percentage to the positive signal.

Relative % to B-PIP3=(A450 of samples include buffer, kinase & inhibitors/A450 of Biotinylated-PIP3 average)×100

IC50 values were calculated from the values read at 450 nm by using Graphpad Prism 5 software.

Biological Data for Select Compounds

Select compounds prepared as described above were assayed according to the biological procedures described herein. The results are given in the table below:

| Structure | IC50 (uM) | | |
|---|---|---|---|
| | PI3Kα | PI3Kγ | PI3Kδ |
| (structure 1) | <10 | <1 | <10 |
| (structure 2) | <10 | <1 | <10 |

-continued

| Structure | IC50 (uM) | | |
|---|---|---|---|
| | PI3Kα | PI3Kγ | PI3Kδ |
| | <1 | <1 | <1 |
| | <1 | <10 | <1 |
| | <10 | <10 | <10 |
| | <10 | <10 | <10 |

The invention claimed is:

1. A compound of formula Ia,

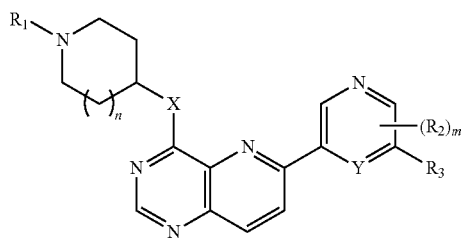

wherein X is NH;
Y is CH;
R$_1$ is H, C$_3$-C$_7$heterocycloalkyl, substituted C$_3$-C$_7$heterocycloalkyl, or COOR$_5$, SOOR$_5$, or CONR$_6$R$_7$;
R$_2$ is halogen;

R$_3$ is NHSO$_2$R$_4$;

R$_4$ is selected from the group consisting of aryl, substituted aryl, heteroaryl and substituted heteroaryl;

R$_5$ is selected from the group consisting of H, alkyl, cycloalkyl, aryl, substituted aryl, heteroaryl and substituted heteroaryl;

R$_6$ and R$_7$ are independently selected from the group consisting of H, alkyl, cycloalkyl, aryl, substituted aryl, heteroaryl and substituted heteroaryl; or R$_6$ and R$_7$ are taken together with the nitrogen atom to form C$_3$-C$_7$heterocycloalkyl or substituted C$_3$-C$_7$heterocycloalkyl;

n is 0, 1 or 2;

m is 0 or 1;

or a pharmaceutically acceptable salt, ester, or tautomer thereof.

2. The compound according to claim 1, which is selected from the following:

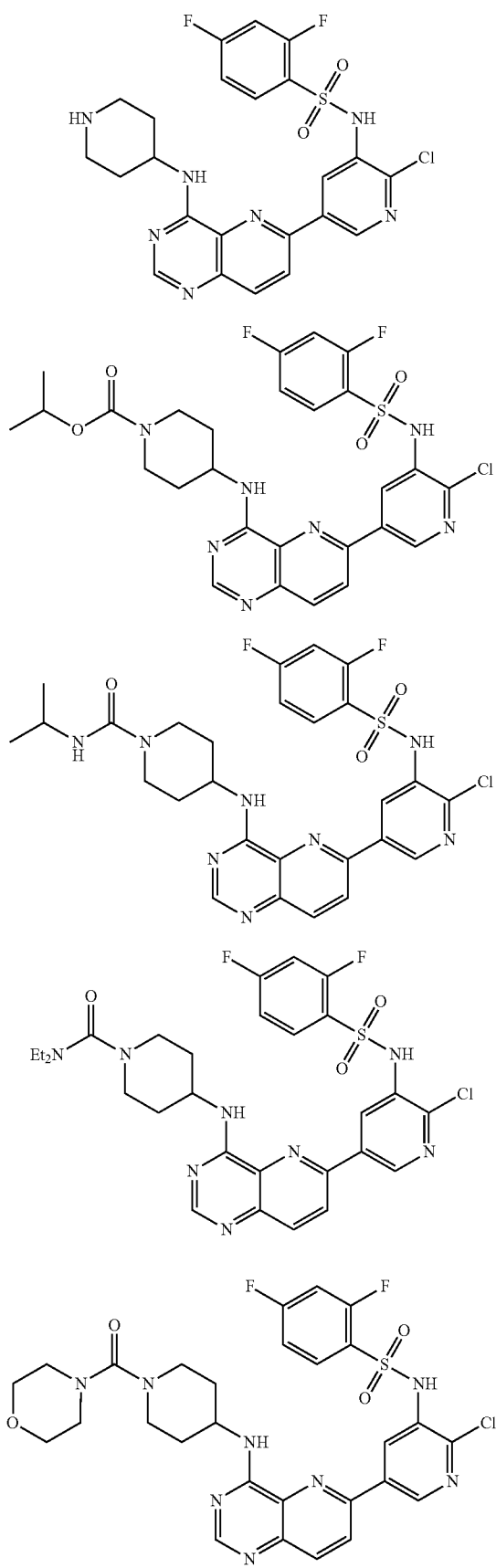
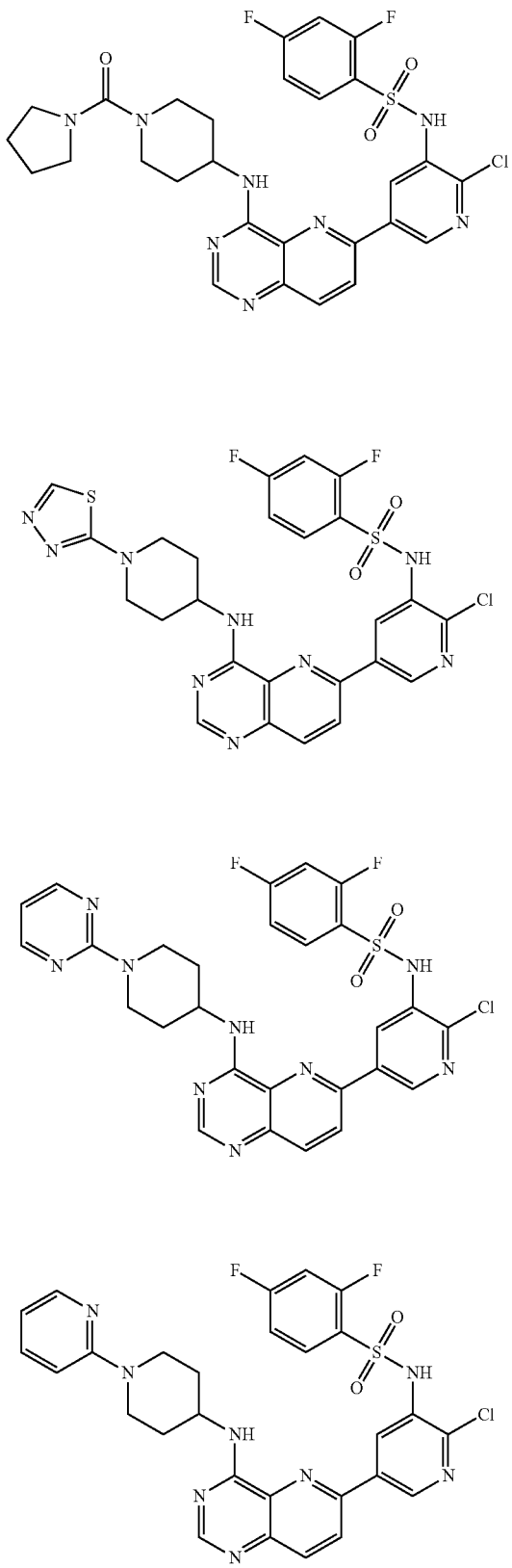

95
-continued
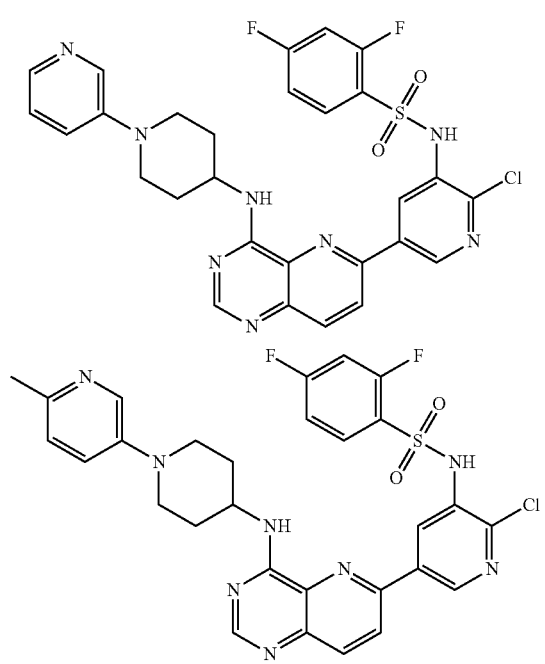
96
-continued
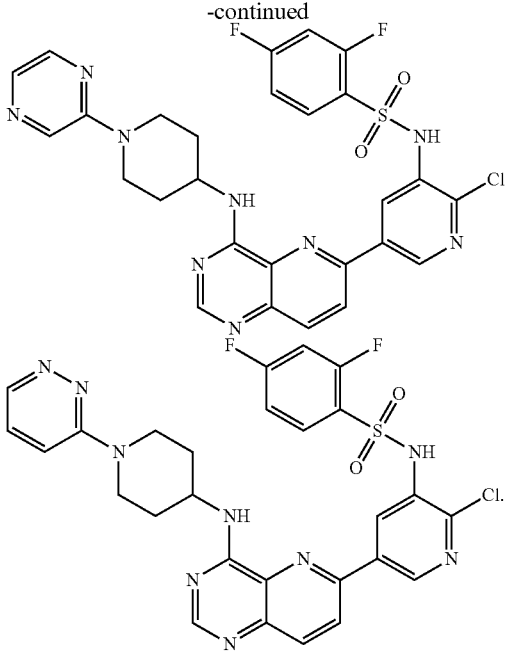
* * * * *